(12) United States Patent
Rasmussen et al.

(10) Patent No.: US 8,288,109 B2
(45) Date of Patent: Oct. 16, 2012

(54) PROCEDURE FOR STRUCTURAL CHARACTERIZATION OF A RECOMBINANT POLYCLONAL PROTEIN OR A POLYCLONAL CELL LINE

(75) Inventors: Lone Kjaer Rasmussen, Skodsborg (DK); Torben Frandsen, Frederiksberg (DK); Soren Kofoed Rasmussen, Roskilde (DK); Peter Sejer Andersen, Vanlose (DK)

(73) Assignee: Symphogen A/S, Lyngby (DK)

( * ) Notice: Subject to any disclaimer, the term of this patent is extended or adjusted under 35 U.S.C. 154(b) by 347 days.

(21) Appl. No.: 11/658,021

(22) PCT Filed: Jul. 20, 2005

(86) PCT No.: PCT/DK2005/000504
§ 371 (c)(1),
(2), (4) Date: Apr. 18, 2007

(87) PCT Pub. No.: WO2006/007853
PCT Pub. Date: Jan. 26, 2006

(65) Prior Publication Data
US 2008/0131882 A1 Jun. 5, 2008

(30) Foreign Application Priority Data

Jul. 20, 2004 (DK) .................. 2004 01133
Dec. 22, 2004 (DK) .................. 2004 01991

(51) Int. Cl.
*C40B 40/10* (2006.01)
*C40B 50/06* (2006.01)

(52) U.S. Cl. ......................................... 435/7.1; 435/6.1

(58) Field of Classification Search ................ None
See application file for complete search history.

(56) References Cited

U.S. PATENT DOCUMENTS

| | | | |
|---|---|---|---|
| 5,126,130 A | 6/1992 | Lussenhop et al. | |
| 5,538,848 A | 7/1996 | Livak et al. | |
| 5,789,208 A | 8/1998 | Sharon | |
| 5,876,925 A | 3/1999 | Siegel | |
| 6,255,455 B1 | 7/2001 | Siegel | |
| 6,312,690 B1 | 11/2001 | Edelman et al. | |
| 6,335,163 B1 | 1/2002 | Sharon | |
| 6,610,472 B1 | 8/2003 | Zhu et al. | |
| 7,749,697 B2 | 7/2010 | Oleksiewicz et al. | |
| 2002/0155114 A1 | 10/2002 | Marks et al. | |
| 2006/0275766 A1* | 12/2006 | Haurum et al. | 435/6 |
| 2007/0141048 A1 | 6/2007 | Oleksiewicz et al. | |
| 2008/0069822 A1 | 3/2008 | Jensen et al. | |
| 2009/0017017 A1 | 1/2009 | Rasmussen et al. | |
| 2009/0136498 A1 | 5/2009 | Haurum et al. | |
| 2009/0186423 A1 | 7/2009 | Frandsen et al. | |
| 2010/0040606 A1 | 2/2010 | Lantto et al. | |
| 2010/0310558 A1 | 12/2010 | Oleksiewicz et al. | |

FOREIGN PATENT DOCUMENTS

| | | |
|---|---|---|
| EP | 0 368 684 B1 | 5/1990 |
| EP | 0 383 777 B1 | 8/1990 |
| EP | 0 393 051 B1 | 10/1990 |
| EP | 0 489 771 B1 | 6/1992 |
| EP | 0 576 093 B1 | 12/1993 |
| EP | 1 106 625 A1 | 6/2001 |
| JP | 2001-502887 A | 3/2001 |
| WO | WO 85/02413 A1 | 6/1985 |
| WO | WO 89/02443 A1 | 3/1989 |
| WO | WO 89/02600 A1 | 3/1989 |
| WO | WO 90/11090 A1 | 10/1990 |
| WO | WO 91/03492 A1 | 3/1991 |
| WO | WO 95/20401 A1 | 8/1995 |
| WO | WO 97/49809 A1 | 12/1997 |
| WO | WO 98/06848 A1 | 2/1998 |
| WO | WO 01/58925 A2 | 8/2001 |
| WO | WO 01/58926 A2 | 8/2001 |
| WO | WO 01/59460 A2 | 8/2001 |
| WO | WO 01/89563 A1 | 11/2001 |
| WO | WO 02/44361 A2 | 6/2002 |
| WO | WO 02/052259 A1 | 7/2002 |
| WO | WO 02/055718 A2 | 7/2002 |
| WO | WO 03/102539 A2 | 12/2003 |
| WO | WO 2004/009618 A2 | 1/2004 |
| WO | WO 2004/035169 A2 | 4/2004 |
| WO | WO 2004/061104 A2 | 7/2004 |
| WO | WO 2005/042774 A2 | 5/2005 |
| WO | WO 2006/007850 A1 | 1/2006 |

OTHER PUBLICATIONS

Akatsuka et al. (Tissue Antigens, 1999, vol. 53, p. 122-134).*
Lubman et al. (J. Chromatogr. B, 2002, 782:183-196, IDS*
Hornbach et al. (J. Immun. Methods, 1998, vol. 218, p. 53-61).*
Wan et al. (Biotechnology Bioengineering, 1999, vol. 62, No. 4, p. 485-488, IDS reference).*
Lubman et al. (J. Chromatogr. B, 2002, 782:183-196, IDS reference).*
Lee et al. (J Chromatogr A, 1997, vol. 790, p. 215-223).*
Williams et al. (Immunology Letters, 2002, vol. 81, p. 141-148).*
Sharon et al. (Combinatorial Chemistry & High Throughput Screening, 2000, vol. 3, p. 185-186, IDS reference).*
Ostriyanina et al. (J. Chrom. A, 2002, 949(1-2):163-171).*
Newkirk et al. (J. Exp. Med. 1987, vol. 166, p. 550-564).*
Bregenholt, S., et al., "Recombinant Human Polyclonal Antibodies: A New Class of Therapeutic Antibodies Against Viral Infections," *Current Pharmaceutical Design* 12:2007-2015, Bentham Science Publishers Ltd. (Jun. 2006).
Haurum, J. and Bregenholt, S., "Recombinant polyclonal antibodies: Therapeutic antibody technologies come full circle," *IDrugs* 8:404-409, The Thomson Corporation (May 2005).
Logtenberg, T., "Antibody cocktails: next-generation biopharmaceuticals with improved potency," *TRENDS in Biotechnology* 25:390-394, Elsevier Ltd. (Sep. 2007).
Meijer, P.-J., et al., "Isolation of Human Antibody Repertoires with Preservation of the Natural Heavy and Light Chain Pairing," *J. Mol. Biol.* 358:764-772, Elsevier Ltd. (May 2006).
Poulsen, T.R., et al., "Kinetic, Affinity, and Diversity Limits of Human Polyclonal Antibody Responses against Tetanus Toxoid," *J. Immunol.* 179:3841-3850, The American Association of Immunologists, Inc. (Sep. 2007).

(Continued)

Primary Examiner — Stephanie K Mummert
(74) Attorney, Agent, or Firm — Sterne, Kessler, Goldstein & Fox P.L.L.C.

(57) ABSTRACT

The present invention provides a structural characterization platform that can be used to assess the stability of a polyclonal cell line during production, as well as batch-to-batch consistency of the final polyclonal products. The structural characterization platform is based on genetic analyses as well as protein characterization techniques that alone or in combination provide the necessary information to characterize the polyclonal cell line and final products. The collection of different homologous proteins to be analyzed with the platform techniques if for example a recombinant polyclonal antibody or a mixture of monoclonal antibodies.

29 Claims, 15 Drawing Sheets

OTHER PUBLICATIONS

Sharon, J., et al., "Recombinant Polyclonal Antibodies for Cancer Therapy," *J. Cell. Biochem.* 96:305-313, Wiley-Liss, Inc. (Oct. 2005).

Tolstrup, A.B., et al., "Development of recombinant human polyclonal antibodies for the treatment of complex human diseases," *Expert. Opin. Biol. Ther.* 6:905-912, Informa UK Ltd. (Sep. 2006).

Wiberg, F.C., et al., "Production of Target-Specific Recombinant Human Polyclonal Antibodies in Mammalian Cells," *Biotechnology and Bioengineering* 94:396-405, Wiley Periodicals, Inc. (Apr. 2006).

Haurum, J.S., "Recombinant polyclonal antibodies: the next generation of antibody therapeutics?" *Drug Discovery Today* 11:655-660, Elsevier Ltd. (Jul. 2006).

Klitgaard, J.L., et al., "Reduced Susceptibility of Recombinant Polyclonal Antibodies to Inhibitory Anti-Variable Domain Antibody Responses," *J. Immunol.* 177:3782-3790, The American Association of Immunologists, Inc. (Sep. 2006).

Aswad, D.W., et al., "Isoaspartate in peptides and proteins: formation, significance, and analysis," *J. Pharma. Biomed. Anal.* 21:1129:1136, Elsevier Science B.V. (2000).

Barbas III, C.F., et al., "Assembly of combinatorial antibody libraries on phage surfaces: The gene III site," *Proc. Natl. Acad. Sci. USA* 88:7978-7982, National Academy of Sciences (1991).

Bernhard, O.K., et al., "Mass spectrometry analysis of CD4-associating proteins using affinity chromatography and affinity tag-mediated purification of tryptic peptides," *Proteomics* 3:139-146, Wiley-VCH Verlag GmbH & Co. KGaA (2003).

Borth, N., et al., "Efficient Selection of High-Producing Subclones During Gene Amplification of Recombinant Chinese Hamster Ovary Cells by Flow Cytometry and Cell Sorting," *Biotechnol. Bioeng.* 71:266-273, John Wiley & Sons, Inc. (2001).

Bregenholt, S., and Haurum, J., "Pathogen-specific recombinant human polyclonal antibodies: biodefence applications," *Expert Opin. Biol. Ther.* 4:387-396, Ashley Publications Ltd. (Mar. 2004).

Brezinsky, S.C.G., et al., "A simple method for enriching populations of transfected CHO cells for cells of higher specific productivity," *J. Immunol. Methods* 277:141-155, Elsevier Science B.V. (2003).

Bye, J.M., et al., "Germline Variable Region Gene Segment Derivation of Human Monoclonal Anti-Rh(D) Antibodies," *J. Clin. Invest.* 90:2481-2490, The American Society for Clinical Investigation, Inc. (1992).

Chang, T.Y., and Siegel, D.L., "Genetic and Immunological Properties of Phage-Displayed Human Anti-Rh(D) Antibodies: Implications for Rh(D) Epitope Topology," *Blood* 91:3066-3078, The American Society of Hematology (1998).

Chelius, D., and Shaler, T.A., "Capture of Peptides with N-Terminal Serine and Threonine: A Sequence-Specific Chemical Method for Peptide Mixture Simplification," *Bioconjug. Chem.* 14:205-211, American Chemical Society (2003).

Chong, B.E., et al., "Chromatofocusing nonporous reversed-phase high-performance liquid chromatography/electrospray ionization time-of-flight mass spectrometry of proteins from human breast cancer whole cell lysates: a novel two-dimensional liquid chromatography/mass spectrometry method," *Rapid Commun. Mass Spectrom.* 15:291-296, John Wiley & Sons, Ltd. (2001).

Crawford, D.H., et al., "Production of Human Monoclonal Antibody to Rhesus D Antigen," *Lancet* 1:386-388, Lancet Publishing Group (1983).

Cronkhite, R., et al., "Regulation of Idiotope Expression. IV. Genetic Linkage of Two D Region-Dependent T15 Idiotopes to the Igh Allotype," *J. Immunol.* 142:568-574, The American Association of Immunologists (1989).

Endo, Y., et al., "Fractionation of Polyclonal Antibody by Isoelectric Focusing and Chromatofocusing: Separation of High-Affinity Rabbit Clonotype Anti-Thyroxine Antibody," *Anal. Biochem.* 144:41-46, Academic Press (1985).

Gallo, P., "Anion-Exchange Chromatography of Normal and Monoclonal Serum Immunoglobulins," *J. Chromatogr.* 416:53-62, Elsevier Science Publishers B.V. (1987).

George, J.N., "Initial management of adults with idiopathic (immune) thrombocytopenic purpura," *Blood Rev.* 16:37-38, Elsevier Science Ltd. (2002).

Gevaert, K., et al., "Chromatographic Isolation of Methionine-containing Peptides for Gel-free Proteome Analysis," *Mol. Cell. Proteomics* 1:896-903, The American Society for Biochemistry and Molecular Biology, Inc. (2002).

Gevaert, K., et al., "Exploring proteomes and analyzing protein processing by mass spectrometric identification of sorted N-terminal peptides," *Nature Biotechnol.* 21:566-569, Nature America Publishing (2003).

Guo, Z., et al., "Direct fluorescence analysis of genetic polymorphisms by hybridization with oligonucleotide arrays on glass supports," *Nucleic Acids Res.* 22:5456-5465, Oxford University Press (1994).

Gygi, S.P., et al., "Quantitative analysis of complex protein mixtures using isotope-coded affinity tags," *Nature Biotechnol.* 17:994-999, Nature America Publishing (1999).

Harris, R.J., et al., "Assessing Genetic Heterogeneity in Production Cell Lines: Detection by Peptide Mapping of a Low Level Tyr to Gln Sequence Variant in a Recombinant Antibody," *Bio/Technology* 11:1293-1297, Butterworth-Heinemann (1993).

Haurum, J., and Bregenholt, S., "Recombinant polyclonal antibodies: Therapeutic antibody technologies come full circle," *IDrugs* 8:404-409, The Thomson Corporation (May 2005).

Higuchi, R., et al., "Kinetic PCR Analysis: Real-time Monitoring of DNA Amplification Reactions," *Bio/Technology* 11:1026-1030, Butterworth-Heinemann (1993).

Højrup, P., "Proteolytic Peptide Mapping," *Methods Mol. Biol.* 251:227-244, Humana Press Inc. (2004).

Holland, P.M., et al., "Detection of specific polymerase chain reaction product by utilizing the 5'→3' exonuclease activity of *Thermus aquaticus* DNA polymerase," *Proc. Natl. Acad. Sci. USA* 88:7276-7280, National Academy of Sciences (1991).

Huse, K., et al., "Purification of antibodies by affinity chromatography," *J. Biochem. Biophys. Methods* 51:217-231, Elsevier Science B.V. (2002).

Issitt, P.D., and Anstee, D.J., "The Rh Blood Group System," in *Appl. Blood Group Serol.*, Montgomery Scientific Publications, Durham, NC, pp. 315-423 (1998).

Jefferis, R., "Glycosylation of Human IgG Antibodies—Relevance to Therapeutic Applications," *Biopharm.: The Technology & Business of Biopharmaceuticals* 14:19-27, Advanstar Communications Inc. (2001).

Kachman, M.T., et al., "A 2-D Liquid Separations/Mass Mapping Method for Interlysate Comparison of Ovarian Cancers," *Anal. Chem.* 74:1779-1791, American Chemical Society (2002).

Kang, X., and Frey, D.D., "High-performance cation-exchange chromatofocusing of proteins," *J. Chromatogr. A* 991:117-128, Elsevier Science B.V. (2003).

Kozbor, D., and Roder, J.C., "The production of monoclonal antibodies from human lymphocytes," *Immunol. Today* 4:72-79, Elsevier Biomedical Press (1983).

Kumpel, B.M., et al., "Clearance of red cells by monoclonal IgG3 anti-D in vivo is affected by the VF polymorphism of FcγRIIIa (CD16)," *Clin. Exp. Immunol.* 132:81-86, Blackwell Publishing Ltd. (2003).

Liu, W.-T., et al., "Characterization of Microbial Diversity by Determining Terminal Restriction Fragment Length Polymorphisms of Genes Encoding 16S rRNA," *Appl. Environ. Microbiol.* 63:4516-4522, American Society for Microbiology (1997).

Livak, K.J., et al., "Oligonucleotides with Fluorescent Dyes at Opposite Ends Provide a Quenched Probe System Useful for Detecting PCR Product and Nucleic Acid Hybridization," *PCR Methods Appl.* 4:357-362, Cold Spring Harbor Laboratory Press (1995).

Lu, D., et al., "Tailoring in Vitro Selection for a Picomolar Affinity Human Antibody Directed against Vascular Endothelial Growth Factor Receptor 2 for Enhanced Neutralizing Activity," *J. Biol. Chem.* 278:43496-43507, The American Society for Biochemistry and Molecular Biology, Inc. (2003).

Lubman, D.M., et al., "Two-dimensional liquid separations—mass mapping of proteins from human cancer cell lysates," *J. Chromatogr. B* 782:183-196, Elsevier Science B.V. (2002).

Miescher, S., et al., "Sequence and Specificity Analysis of Recombinant Human Fab Anti-Rh D Isolated by Phage Display," *Vox Sang.* 75:278-287, S. Karger AG (1998).

Miescher, S., et al., "CHO expression of a novel human recombinant IgG1 anti-RhD antibody isolated by phage display," *Br. J. Hematol.* 111:157-166, Blackwell Science Ltd. (2000).

Miescher, S., et al., "A single recombinant anti-RhD IgG prevents RhD immunization: association of RhD-positive red blood cell clearance rate with polymorphisms in the FcγRIIA and FcγIIIA genes," *Blood* 103:4028-4035, American Society of Hematology (Jun. 2004).

Mozdzanowski, J., et al., "High-Yield Deblocking of Amino Termini of Recombinant Immunoglobulins with Pyroglutamate Aminopeptidase," *Anal. Biochem.* 260:183-187, Academic Press (1998).

Nowakowski, A., et al., "Potent neutralization of botulinum neurotoxin by recombinant oligoclonal antibody," *Proc. Natl. Acad. Sci. USA* 99:11346-11350, National Academy of Sciences (2002).

Pease, A.C., et al., "Light-generated oligonucleotide arrays for rapid DNA sequence analysis," *Proc. Natl. Acad. Sci. USA* 91:5022-5026, National Academy of Sciences (1994).

Perkins, M., et al., "Determination of the Origin of Charge Heterogeneity in a Murine Monoclonal Antibody," *Pharma. Res.* 17:1110-1117, Plenum Publishing Corporation (2000).

Rasmussen, T., et al., "Quantitation of minimal residual disease in multiple myeloma using an allele-specific real-time PCR assay," *Exper. Hematol.* 28:1039-1045, Elsevier Science Inc. (2000).

Scharf, O., et al., "Immunoglobulin G3 from Polyclonal Human Immunodeficiency Virus (HIV) Immune Globulin is More Potent than Other Subclasses in Neutralizing HIV Type 1," *J. Virol.* 75:6558-6565, American Society for Microbiology (2001).

Schenerman, M.A., et al., "CMC Strategy Forum Report—Analysis and Structure Characterization of Monoclonal Antibodies," *BioProcess Int.* 2:42-52, PJB Publications (Feb. 2004).

Scott, J.K., and Smith, G.P., "Searching for Peptide Ligands with an Epitope Library," *Science* 249:386-390, American Association for the Advancement of Science (1990).

Selinger, M., "Immunoprophylaxis for rhesus disease—expensive but worth it?," *Br. J. Obstet. Gynaecol.* 98:509-512, Blackwell Scientific Publications (1991).

Sharon, J., et al., "Construction of Polyclonal Antibody Libraries Using Phage Display," *Methods Mol. Biol.* 178:101-112, Humana Press Inc. (2002).

Siegel, D.L., et al., "Section 5: Structural/genetic analysis of mAbs to blood group antigens. Coordinator's report," *Transfus. Clin. Biol.* 9:83-97, Elsevier SAS (2002).

Singh-Gasson, S., et al., "Maskless fabrication of light-directed oligonucleotide microarrays using a digital micromirror array," *Nature Biotechnol.* 17:974-978, Nature American Publishing (1999).

Sittisombut, N., "Human Immunoglobulin Isotypes and Allotypes," in *Weir's Handbook of Experimental Immunology, ed. 5*., Herzenberg L., et al., eds., Oxford: Blackwell, Stanford, CA, 25.1-25.9. (1996).

Stucki, M., et al., "Characterisation of a chromatographically produced anti-D immunoglobulin product," *J. Chromatogr. B* 700:241-248, Elsevier Science B.V. (1997).

Suárez-Álvarez, B., et al., "Characterisation of mouse monoclonal antibodies for pneumolysin: fine epitope mapping and V gene usage," *Immunol. Lett.* 88:227-239, Elsevier Science B.V. (2003).

Wan, M., et al., "Variant Antibody Identification by Peptide Mapping," *Biotechnol. Bioeng.* 62:485-488, John Wiley & Sons, Inc. (1999).

Wang, H., et al., "A protein molecular weight map of ES2 clear cell ovarian carcinoma cells using a two-dimensional liquid separations/mass mapping technique," *Electrophoresis* 23:3168-3181, Wiley-VCH Verlag GmbH & Co. KGaA (2002).

Wilhelm, J., and Pingoud, A., "Real-Time Polymerase Chain Reaction," *ChemBioChem* 4:1120-1128, Wiley-VCH Verlag GmbH & Co. KGaA (2003).

Willcox, B.E., et al., "Production of soluble αβ T-cell receptor heterodimers suitable for biophysical analysis of ligand binding," *Prot. Sci.* 8:2418-2423, Cambridge University Press (1999).

Wu, H., et al., "Cloning, isolation and characterization of human tumor in situ monoclonal antibodies," *Cancer Immunol. Immunother.* 51:79-90, Springer-Verlag (2002).

International Search Report for International Application No. PCT/DK2005/000504, European Patent Office, Netherlands, mailed on Mar. 30, 2006.

Co-pending U.S. Appl. No. 11/633,070, inventors Jensen, A., et al., filed Dec. 4, 2006.

Co-pending U.S. Appl. No. 11/632,937, inventors Rasmussen, S.K., et al., filed Jan. 19, 2007.

Co-pending U.S. Appl. No. 11/792,927, inventors Lantto, J., et al., filed Jun. 13, 2007.

Bhat, S., "Galactose to ceramide linkage is essential for the binding of a polyclonal antibody to galactosyl ceramide," *J. Neuroimmunol.* 41:105-110, Elsevier Science Publishers B.V. (1992).

Chen, L., et al., "Expression of a prototypic anti-colorectal cancer polyclonal antibody library in mammalian cells," *Immunol. Lett.* 88:135-140, Elsevier Science B.V. (Aug. 2003).

Tölö, H., et al., "Development of a Highly Purified Multicomponent Leukocyte IFN-α Product," *J. Interferon Cytokine Res.* 21:913-920, Mary Ann Liebert, Inc. (2001).

Adamczyk, M. et al., "Profiling of polyclonal antibody light chains by liquid chromatography/electrospray ionization mass spectrometry," *Rapid Commun Mass Spectrom.* 14(1): 49-51, John Wiley and Sons Ltd., England (2000).

Cheng, W.C. et al., "Fractionation of antibodies to the pneumococcal polysaccharides by affinity chromatography," *J Immunol.* 111(6): 1677-89, American Association of Immunologists, United States (Dec. 1973).

Shirwan, H. et al., "Rejection of cardiac allografts by T cells expressing a restricted repertoire of T-cell receptor V β genes," *Immunology* 90(4): 572-8, Blackwell Scientific Publications, England (Apr. 1997).

Grüntzig, V., et al., "Improved Protocol for T-RFLP by Capillary Electrophoresis," available online at http://rdp8.cme.msu.edu/html/t-rflp_jul02.html (2002).

Judah, J.D., and Nicholls, M.R., "The Separation of Intracellular Serum Albumin from Rat Liver," *Biochem. J.* 123:643-648, Portland Press (1971).

Kenny, J., and Nika, H., "N-terminal Sequence Analysis of Proteins Electroblotted to PVDF Membrane Using Routine 3.1 PVDF Method on the HP G1005A N-terminal Protein Sequencing System," available online at http://www.chem.agilent.com/Library/applications/59653463.pdf (1996).

Mhatre, R., et al., "Purification of antibody Fab fragments by cation-exchange chromatography and pH gradient elution," *J. Chromatogr. A* 707:225-231, Elsevier (1995).

Peixuan, Z., et al., Typing *Neisseria meningitidis* by Analysis of Restriction Fragment Length Polymorphisms in the Gene Encoding the Class 1 Outer Membrane Protein: Application to Assessment of Epidemics Throughout the Last 4 Decades in China, *J. Clin. Microbiol.* 33:458-462, American Society for Microbiology (1995).

Sanger, F., et al., "DNA sequencing with chain-terminating inhibitors," *Proc. Natl. Acad. Sci. U.S.A.* 74:5463-5467, National Academy of Sciences (1977).

Partial European Search Report for European Patent Application No. EP 09 15 1073, completed on Mar. 24, 2009, European Patent Office, The Hague, Netherlands.

Sharon, J., et al., "Recombinant Polyclonal Antibody Libraries," *Comb. Chemistry High Through Screening* 3:185-196, Bentham Science Publishers Ltd. (2000).

Maui, R., "БИОХИМИЯ ЧЕЛОВЕКА [Biochemistry of a human]," vol. 1, pp. 29-31 and 36, Mockba [Moscow], MIR (1993).

Co-pending U.S. Appl. No. 12/788,202, Martin B. Oleksiewicz et al., filed May 26, 2010.

Edelman, L., et al., "Obtaining a functional recombinant anti-rhesus (D) antibody using the baculovirus-insect cell expression system," *Immunology* 91:13-19, Blackwell Science Ltd., United Kingdom (1997).

Rasmussen, S,K., et al., "Manufacture of recombinant polyclonal antibodies," *Biotechnol. Lett.* 29:845-52, Springer Science+Business Media B.V., Netherlands (2007).

Sarantopoulos. S., et al., "A Method for Linking $V_L$ and $V_H$ Region Genes That Allows Bulk Transfer Between Vectors for Use in Generating Polyclonal IgG Libraries," *J. Immunol.* 152:5344-51, American Association of Immunologists, United States (1994).

Scaradavou, A., et al., "Intravenous Anti-D Treatment of Immune Thrombocytopenic Purpura: Experience in 272 Patients," *Blood* 89:2689-700, American Society of Hematology, United States (1997).

\* cited by examiner

Rhd203   Rhd191  Rhd324           Rhd306   Rhd196   Rhd319
                  |                         |
                Rhd201                    Rhd244

SEQUENCE LISTING

<160> NUMBER OF SEQ ID NOS: 45

<210> SEQ ID NO 1
<211> LENGTH: 20
<212> TYPE: DNA
<213> ORGANISM: Artificial sequence
<220> FEATURE:
<223> OTHER INFORMATION: Synthetic primer sequence

<400> SEQUENCE: 1
tctcttccgc atcgctgtct                    20

<210> SEQ ID NO 2
<211> LENGTH: 24
<212> TYPE: DNA
<213> ORGANISM: Artificial sequence
<220> FEATURE:
<223> OTHER INFORMATION: Synthetic primer sequence

<400> SEQUENCE: 2
aggaaaggac agtgggagtg gcac                                     24

<210> SEQ ID NO 3
<211> LENGTH: 20
<212> TYPE: DNA
<213> ORGANISM: Artificial sequence
<220> FEATURE:
<223> OTHER INFORMATION: Synthetic primer sequence

<400> SEQUENCE: 3
cgtagctctt ttaagaggtg                                          20

<210> SEQ ID NO 4
<211> LENGTH: 20
<212> TYPE: DNA
<213> ORGANISM: Artificial sequence
<220> FEATURE:
<223> OTHER INFORMATION: Synthetic primer sequence

<400> SEQUENCE: 4
accgatgggc ccttggtgga                                          20

<210> SEQ ID NO 5
<211> LENGTH: 8
<212> TYPE: PRT
<213> ORGANISM: Homo Sapiens

<400> SEQUENCE: 5

Gln Val Gln Leu Val Glu Ser Gly
1               5

<210> SEQ ID NO 6
<211> LENGTH: 8
<212> TYPE: PRT
<213> ORGANISM: Homo Sapiens

<400> SEQUENCE: 6

Glu Val Gln Leu Val Glu Ser Gly
1               5

<210> SEQ ID NO 7
<211> LENGTH: 7
<212> TYPE: PRT
<213> ORGANISM: Homo Sapiens

<400> SEQUENCE: 7

Glu Ile Val Leu Thr Gln Ser
1               5

<210> SEQ ID NO 8
<211> LENGTH: 7
<212> TYPE: PRT
<213> ORGANISM: Homo Sapiens

<400> SEQUENCE: 8

Asp Ile Gln Met Thr Gln Ser
1               5

<210> SEQ ID NO 9
<211> LENGTH: 7
<212> TYPE: PRT
<213> ORGANISM: Homo Sapiens

<400> SEQUENCE: 9

Asp Ile Gln Met Thr Gln Ser
1               5

```
<210> SEQ ID NO 10
<211> LENGTH: 7
<212> TYPE: PRT
<213> ORGANISM: Homo Sapiens

<400> SEQUENCE: 10

Gln Ser Ala Leu Thr Gln Pro
1               5

<210> SEQ ID NO 11
<211> LENGTH: 13
<212> TYPE: PRT
<213> ORGANISM: Artificial sequence
<220> FEATURE:
<223> OTHER INFORMATION: Synthetic peptide

<400> SEQUENCE: 11

Ala Cys Met Gly Tyr Gly Pro Arg Met Cys Gly Gly Gly
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide

<400> SEQUENCE: 12

Ala Cys Pro Gly Asp Gly Pro Arg Met Cys Gly Gly Gly
1               5                   10

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Cys Met Gly Tyr Gly Pro Arg Met Cys
1               5

<210> SEQ ID NO 14
<211> LENGTH: 13
<212> TYPE: PRT
<213> ORGANISM: Artificial sequence
<220> FEATURE:
<223> OTHER INFORMATION: Synthetic peptide

<400> SEQUENCE: 14

Ala Cys Met Pro Arg Asn Pro Leu Glu Cys Gly Gly Gly
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthetic peptide

<400> SEQUENCE: 15

Ala Cys Ala Pro Arg Asn Pro Tyr Glu Cys Gly Gly Gly
1               5                   10

<210> SEQ ID NO 16
<211> LENGTH: 13
```

```
<212> TYPE: PRT
<213> ORGANISM: Artificial sequence
<220> FEATURE:
<223> OTHER INFORMATION: Synthetic peptide

<400> SEQUENCE: 16

Ala Cys Pro Arg Asn Pro Phe Glu Met Cys Gly Gly Gly
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic peptide

<400> SEQUENCE: 17

Ala Cys Tyr Pro Arg His Pro Leu Asp Cys Gly Gly Gly
1               5                   10

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Cys Ala Pro Arg Asn Pro Tyr Glu Cys
1               5

<210> SEQ ID NO 19
<211> LENGTH: 13
<212> TYPE: PRT
<213> ORGANISM: Artificial sequence
<220> FEATURE:
<223> OTHER INFORMATION: Synthetic peptide

<400> SEQUENCE: 19

Ala Cys Thr Thr Leu Leu His Phe Leu Cys Gly Gly Gly
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Ala Cys Thr Thr Leu Leu Ser Phe Leu Cys Gly Gly Gly
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Ala Gly Thr Ser Leu Leu Ala Phe Leu Cys Gly Gly Gly
1               5                   10

<210> SEQ ID NO 22
<211> LENGTH: 13
<212> TYPE: PRT
<213> ORGANISM: Artificial sequence
```

```
<220> FEATURE:
<223> OTHER INFORMATION: Synthetic peptide

<400> SEQUENCE: 22

Ala Cys Asn Leu Leu Leu Gln Phe Leu Cys Gly Gly Gly
1               5                   10

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Cys Thr Thr Leu Leu His Phe Leu Cys
1               5

<210> SEQ ID NO 24
<211> LENGTH: 21
<212> TYPE: DNA
<213> ORGANISM: Artificial sequence
<220> FEATURE:
<223> OTHER INFORMATION: Synthetic primer sequence

<400> SEQUENCE: 24
cacggctgag tattactgtg c                                              21

<210> SEQ ID NO 25
<211> LENGTH: 17
<212> TYPE: DNA
<213> ORGANISM: Artificial sequence
<220> FEATURE:
<223> OTHER INFORMATION: Synthetic primer sequence

<400> SEQUENCE: 25
ttggtggagc cactcga                                                   17

<210> SEQ ID NO 26
<211> LENGTH: 33
<212> TYPE: DNA
<213> ORGANISM: Artificial sequence
<220> FEATURE:
<223> OTHER INFORMATION: Synthetic primer sequence

<400> SEQUENCE: 26
agaaatttgt tcggtgacta cgatcttaag tcc                                 33

<210> SEQ ID NO 27
<211> LENGTH: 28
<212> TYPE: DNA
<213> ORGANISM: Artificial sequence
<220> FEATURE:
<223> OTHER INFORMATION: Synthetic primer sequence

<400> SEQUENCE: 27
agagaattga gcacgcaacg tggataca                                       28

<210> SEQ ID NO 28
<211> LENGTH: 34
<212> TYPE: DNA
<213> ORGANISM: Artificial sequence
<220> FEATURE:
<223> OTHER INFORMATION: Synthetic primer sequence

<400> SEQUENCE: 28
agagagagta ctctatatag cagcagctgg taca                                34
```

<210> SEQ ID NO 29
<211> LENGTH: 29
<212> TYPE: DNA
<213> ORGANISM: Artificial sequence
<220> FEATURE:
<223> OTHER INFORMATION: Synthetic primer sequence

<400> SEQUENCE: 29
gatggtctcc tatagcagca gctggtacc                                    29

<210> SEQ ID NO 30
<211> LENGTH: 29
<212> TYPE: DNA
<213> ORGANISM: Artificial sequence
<220> FEATURE:
<223> OTHER INFORMATION: Synthetic primer sequence

<400> SEQUENCE: 30
gagagactct gttcggggag tcagtagat                                    29

<210> SEQ ID NO 31
<211> LENGTH: 29
<212> TYPE: DNA
<213> ORGANISM: Artificial sequence
<220> FEATURE:
<223> OTHER INFORMATION: Synthetic primer sequence

<400> SEQUENCE: 31
gggtactctg tatagcagca gctggtaca                                    29

<210> SEQ ID NO 32
<211> LENGTH: 33
<212> TYPE: DNA
<213> ORGANISM: Artificial sequence
<220> FEATURE:
<223> OTHER INFORMATION: Synthetic primer sequence

<400> SEQUENCE: 32
agagacctac aagggtatag aagcagctgg tac                               33

<210> SEQ ID NO 33
<211> LENGTH: 22
<212> TYPE: DNA
<213> ORGANISM: Artificial sequence
<220> FEATURE:
<223> OTHER INFORMATION: Synthetic primer sequence

<400> SEQUENCE: 33
ccgacgattt ttggagtggg cc                                           22

<210> SEQ ID NO 34
<211> LENGTH: 20
<212> TYPE: DNA
<213> ORGANISM: Artificial sequence
<220> FEATURE:
<223> OTHER INFORMATION: Synthetic primer sequence

<400> SEQUENCE: 34
tctcttccgc atcgctgtct                                              20

<210> SEQ ID NO 35
<211> LENGTH: 24
<212> TYPE: DNA
<213> ORGANISM: Artificial sequence
<220> FEATURE:
<223> OTHER INFORMATION: Primer sequence

```
<400> SEQUENCE: 35
aggaaaggac agtgggagtg gcac                                              24

<210> SEQ ID NO 36
<211> LENGTH: 23
<212> TYPE: DNA
<213> ORGANISM: Artificial sequence
<220> FEATURE:
<223> OTHER INFORMATION: Synthetic primer sequence

<400> SEQUENCE: 36 cgttctttt cgcaacgggt ttg                                                23

<210> SEQ ID NO 37
<211> LENGTH: 23
<212> TYPE: DNA
<213> ORGANISM: Artificial sequence
<220> FEATURE:
<223> OTHER INFORMATION: Synthetic primer sequence

<400> SEQUENCE: 37
aagaccgatg ggcccttggt gga                                               23

<210> SEQ ID NO 38
<211> LENGTH: 21
<212> TYPE: DNA
<213> ORGANISM: Artificial sequence
<220> FEATURE:
<223> OTHER INFORMATION: Synthetic primer sequence

<400> SEQUENCE: 38
aacgggtttg ccgccagaac a                                                 21

<210> SEQ ID NO 39
<211> LENGTH: 19
<212> TYPE: DNA
<213> ORGANISM: Artificial sequence
<220> FEATURE:
<223> OTHER INFORMATION: Synthetic primer sequence

<400> SEQUENCE: 39
ccgagggacc tgagcgagt                                                    19

<210> SEQ ID NO 40
<211> LENGTH: 5
<212> TYPE: PRT
<213> ORGANISM: Homo Sapiens

<400> SEQUENCE: 40

Gln Val Gln Leu Val
1               5

<210> SEQ ID NO 41
<211> LENGTH: 5
<212> TYPE: PRT
<213> ORGANISM: Homo Sapiens

<400> SEQUENCE: 41

Gln Leu Gln Leu Gln
1               5

<210> SEQ ID NO 42
<211> LENGTH: 5
<212> TYPE: PRT
<213> ORGANISM: Homo Sapiens
```

```
<400> SEQUENCE: 42

Asp Ile Gln Leu Thr
1               5

<210> SEQ ID NO 43
<211> LENGTH: 5
<212> TYPE: PRT
<213> ORGANISM: Homo Sapiens

<400> SEQUENCE: 43

Asp Ile Gln Met Thr
1               5

<210> SEQ ID NO 44
<211> LENGTH: 33
<212> TYPE: DNA
<213> ORGANISM: Artificial sequence
<220> FEATURE:
<223> OTHER INFORMATION: Synthetic primer sequence

<400> SEQUENCE: 44
tgggcgcgcc gaggtgcagc tggtggagtc tgg                                    33

<210> SEQ ID NO 45
<211> LENGTH: 30
<212> TYPE: DNA
<213> ORGANISM: Artificial sequence
<220> FEATURE:
<223> OTHER INFORMATION: Synthetic primer sequence

<400> SEQUENCE: 45
ggaggcgctc gagacggtga ccgtggtccc                                        30
```

PROCEDURE FOR STRUCTURAL CHARACTERIZATION OF A RECOMBINANT POLYCLONAL PROTEIN OR A POLYCLONAL CELL LINE

This application is a National Stage of International Application No. PCT/DK2005/000504, filed Jul. 20, 2005, which claims the benefit of Danish Application No. PA 2004 01133, filed Jul. 20, 2004, and Danish Application No. PA 2004 01991, filed Dec. 22, 2004.

FIELD OF THE INVENTION

The present invention relates to a procedure for structural characterization of a recombinant polyclonal protein or a polyclonal cell line producing such a protein, in order to verify batch-to-batch consistency of the final products as well as compositional stability during single production runs. In particular the present invention relates to a procedure for characterizing a recombinant polyclonal antibody.

BACKGROUND OF THE INVENTION

It has long been recognized that prophylactic or therapeutic administration of antibodies (so-called passive immunization) may enhance the ability of the body's immune system to eliminate infectious agents. Such therapeutic antibodies have historically been obtained from human plasma (whence the antibody composition is termed immunoglobulin or gammaglobulin). To obtain these antibodies, pools of blood are collected from immune human donors and the immunoglobulin fraction is extracted and purified. Only a fraction of the immunoglobulin will be specific for a particular antigen. The therapeutic use of immunoglobulin is complicated due to several limitations such as a limited number of donors, expensive manufacturing, risk of infectious contaminants from donors, inevitable batch-to-batch variations as well as complicated administration regimens.

Recombinant monoclonal antibodies have recently provided an alternative to immunoglobulin products. They are, however, only directed against a single target and may therefore not be as effective against targets that are complex or dynamic, such as infectious agents. There are some examples of mixing monoclonal antibodies in order to overcome this problem (e.g. Nowakowski, A. et al. 2002. Proc Natl Acad Sci USA 99, 11346-11350 and U.S. Pat. No. 5,126,130).

Recently a technology for recombinant production of highly specific polyclonal antibodies suitable for prophylactic and therapeutic administration has been developed (WO 2004/061104). The recombinant polyclonal antibody (rpAb) can be purified from a production bioreactor as a single preparation without separate handling, manufacturing, purification, or characterization of the individual members constituting the recombinant polyclonal protein. However, such a production strategy requires a procedure for verifying the identity and demonstrating consistent production of the complex mixture of antibody molecules over time.

Further, a polyclonal antibody produced industrially using recombinant technology will have to be characterized to a certain degree in order to obtain approval as an investigative or therapeutic drug from national and supranational regulatory authorities. Since the recombinant polyclonal antibody approach is a completely new concept, the issue of characterizing a sample comprising multiple different but highly homologous proteins with respect to the relative proportion of the individual proteins in the sample has never been addressed before. Thus, blood-derived immunoglobulin is generally approved based on non-clinical and clinical efficacy data and often historical safety data, as well as crude chemistry, manufacturing, and control (CMC) parameters such as purity, titre of binding, and absence of adventitious agents. Such a simplistic approach is of course not acceptable for recombinantly produced proteins. Hence, for mixtures of a few monoclonal antibodies, the regulatory guidelines state that such a mixture should be subjected to individual characterization of each constituent antibody in the mixture using comprehensive protein chemical characterization techniques coupled with biological assays. However, this is not a technically feasible approach or appropriate for a genuinely polyclonal composition, based on more than 10, 20 or even more different antibodies.

DISCLOSURE OF CONTRIBUTION

The present invention provides a structural characterization platform for demonstrating consistent production of a mixture of different homologous proteins, such as a recombinant polyclonal protein, in particular a recombinant polyclonal antibody, from a polyclonal cell line.

DESCRIPTION OF THE INVENTION

A prerequisite for industrial production of a recombinant polyclonal protein for prophylactic and therapeutic use is the maintenance of clonal diversity during expression. Therefore, it is important to be able to monitor and measure the clonal diversity of a polyclonal cell line producing a polyclonal antibody, as well as the relative representation of individual proteins in the polyclonal protein at any desired time point, and in any relevant sample, thus allowing for analysis of the stability of the expression system in a single run, as well as batch-to-batch variation of the final product.

Homologous protein compositions such as a recombinant polyclonal antibody or a recombinant polyclonal T cell receptor (TcR) are comprised of variant proteins with very similar physico-chemical properties. This is an advantage when purifying a recombinantly produced polyclonal protein, since the purification can be performed as if it was a single protein, without the loss of diversity during the process. This similarity, however, provides a challenge when characterizing the relative distribution of the individual members of a polyclonal protein, because the similarity in the physico-chemical properties makes it difficult to distinguish one individual member from the other.

Most commonly, when producing a recombinant polyclonal protein, the original composition is known, because the sequences encoding the polyclonal protein have been isolated, screened and sequenced prior to the generation of a polyclonal manufacturing cell line for the production of the recombinant polyclonal protein. For generation of such a cell line, please see WO 2004/061104, hereby incorporated by reference. The rare exception to this may be situations where an unscreened or unselected library, e.g. from a convalescent patient is used directly to generate a recombinant polyclonal antibody.

To ensure that the diversity of the output (the recombinant polyclonal protein) resembles the diversity of the input (the library of encoding sequences) after cultivation and purification, it will be necessary to obtain information with respect to the relative proportion of the individual members of the polyclonal protein and/or their encoding sequences within the polyclonal manufacturing cell line. The present invention provides a structural characterization platform, based on genetic analyses as well as protein characterization techniques, capable of providing information with respect to the diversity of both a polyclonal cell line and a polyclonal protein.

DEFINITIONS

The term "anti-idiotype antibody" refers to a full-length antibody or fragment thereof (e.g. a Fv, scFv, Fab, Fab' or F(ab)$_2$) which specifically binds to the variant part of an individual member of a polyclonal protein. Preferably, an anti-idiotype antibody of the present invention specifically binds to the variant part of an individual member of a polyclonal antibody or a polyclonal TcR. The anti-idiotype antibody specificity is preferably directed against the antigen-specific part of an individual member of a polyclonal antibody or a polyclonal T cell receptor, the so-called V-region. It may, however, also show specificity towards a defined sub-population of individual members, e.g. a specific VH gene family represented in the mixture.

The term "anti-idiotype peptide" refers to a specific peptide-ligand, which is capable of associating specifically and thus identifying an individual protein member within a mixture of homologous proteins. Preferably, an anti-idiotype peptide of the present invention binds specifically to an individual member of a polyclonal antibody or a polyclonal TcR. The anti-idiotype peptides of the present invention are preferably directed against the antigen-specific part of the sequence of an individual antibody or an individual T cell receptor. An anti-idiotype peptide may, however, also show specificity towards a defined sub-population of individual members.

The term ""bulk" N-terminal sequencing" refers to N-terminal protein sequencing of a sample comprising a number of variant homologous protein molecules, e.g. a polyclonal protein. This bulk sequencing provides sequence information of all the different proteins present within the sample at the same time. In positions where the amino acids vary among the individual members in the sample, these can be quantitated and the different amounts of individual amino acids at variable positions will provide information with respect to the protein sub-population which contain a particular variation. If the proteins to be N-terminal sequenced contain more than one sub-unit, these are preferably separated prior to sequencing to reduce complexity, e.g. if the sample is a polyclonal antibody heavy chains may be separated from light chains prior to sequencing.

The term "clonal diversity" or "polyclonality" refers to the variability or diversity of a polyclonal protein, the nucleic acid sequences encoding it, or the polyclonal cell line producing it. The variability is characterized by the differences in the amino acid sequences or nucleic acid sequences between the individual members of the polyclonal protein or the library of encoding sequences. For polyclonal cell lines the clonal diversity may be assessed by the variability of nucleic acid sequences represented within the cell line, e.g. as single-site integrations into the genome of the individual cells. It may, however, also be assessed as the variability of amino acid sequences represented on the surface of the cells within the cell line.

The term "epitope" refers to the part of an antigenic molecule to which a T-cell receptor or an antibody will bind. An antigen or antigenic molecule will generally present several or even many epitopes simultaneously.

The term "immunoglobulin" commonly is used as a collective designation of the mixture of antibodies found in blood or serum. Hence a serum-derived polyclonal antibody is often termed immunoglobulin or gamma globulin. However, immunoglobulin may also be used to designate a mixture of antibodies derived from other sources, e.g. recombinant immunoglobulin.

The term "individual clone" as used herein, denotes an isogenic population of cells expressing a particular protein, e.g. a monoclonal antibody. Such individual clones can for example be obtained by transfection of a host cell with a desired nucleic acid, and following selection for positive transfectants, a single clone may be expanded or a number of single clones may be pooled and expanded. A polyclonal cell line can be generated by mixing individual clones expressing different individual members of a polyclonal protein.

The terms "an individual member" or "a distinct member" denote a protein molecule of a protein composition comprising different, but homologous protein molecules, such as a polyclonal protein, where the individual protein molecule is homologous to the other molecules of the composition, but also contains one or more stretches of polypeptide sequence, which is characterized by differences in the amino acid sequence between the individual members of the polyclonal protein, also termed a variable region. For example in a polyclonal antibody comprised of Ab1 to Ab50, all the proteins with the sequence of Ab1 will be considered as an individual member of the polyclonal antibody and Ab1 may for example differ from Ab2 proteins in the CDR3 region. A sub-population of individual members can for example be constituted of the antibodies belonging to Ab1, Ab12 and Ab33.

The term "polyclonal antibody" describes a composition of different antibody molecules which is capable of binding to or reacting with several different specific antigenic determinants on the same or on different antigens. The variability of a polyclonal antibody is located in the so-called variable regions of the individual antibodies constituting the polyclonal antibody, in particular in the complementarity determining regions (CDR)1, CDR2 and CDR3 regions.

The terms "polyclonal manufacturing cell line", "polyclonal cell line", "polyclonal master cell bank (pMCB)", and "polyclonal working cell bank (pWBC)" are used interchangeably and refers to a population of protein-expressing cells that are transfected with a library of variant nucleic acid sequences of interest. Preferably, the individual cells, which together constitute the recombinant polyclonal manufacturing cell line, carry only one copy of a distinct nucleic acid sequence of interest, which encodes one member of the recombinant polyclonal protein of interest, and each copy is integrated into the same site of the genome of each cell. Cells which can constitute such a manufacturing cell line can for example be bacteria, fungi, eukaryotic cells, such as yeast, insect cells or mammalian cells, especially immortal mammalian cell lines such as CHO cells, COS cells, BHK cells, myeloma cells (e.g., Sp2/0 cells, NS0), NIH 3T3, YB2/0 and immortalized human cells, such as HeLa cells, HEK 293 cells, or PER.C6.

As used herein, the term "polyclonal protein" refers to a protein composition comprising different, but homologous protein molecules, preferably selected from the immunoglobulin superfamily. Even more preferred are homologous protein molecules which are antibodies or T cell receptors (TcR). Thus, each protein molecule is homologous to the other molecules of the composition, but also contains one or more stretches of variable polypeptide sequence, which is/are characterized by differences in the amino acid sequence between the individual members also termed distinct variant members of the polyclonal protein. Known examples of such polyclonal proteins include antibodies, T cell receptors and B cell receptors. A polyclonal protein may consist of a defined subset of protein molecules, which has been defined by a common feature such as the shared binding activity towards a desired target, e.g. in the case of a polyclonal antibody against the desired target antigen. A recombinant polyclonal protein is generally composed of such a defined subset of molecules, where the sequence of each member is known. Only in rare cases may a recombinant polyclonal protein resemble a serum-derived immunoglobulin in the sense that the recombinant polyclonal protein also contains a significant proportion of non-target-specific proteins.

The term "polyclonal T cell receptor (TcR)" describes a composition of different TcR molecules which is capable of binding to or reacting with several different specific antigenic determinants from the same or from different antigens. The variability of a polyclonal TcR is located in the so-called variable regions of the individual TCR molecules constituting the polyclonal TcR, in particular in the CDR1, CDR2, CDR3 and CDR4 regions. The TcR molecules of the present invention are engineered soluble dimers of the alpha-beta chains or gamma-delta chains. Such engineered TcRs are for example described in (Willcox, B. E. et al. 1999. Protein Sci 8, 2418-2423).

The term "protein" refers to any chain of amino acids, regardless of length or post-translational modification. Proteins can exist as monomers or multimers, comprising two or more assembled polypeptide chains, fragments of proteins, polypeptides, oligopeptides, or peptides.

The term "sentinel protein" describes an individual member of a polyclonal protein, which can be monitored for its presence during production of the polyclonal protein or in different batches. Consistency in the presence of a sentinel protein in a series of related samples will reflect stability in the expression of a polyclonal protein between batches or over time in a single production. Further, it will reflect maintenance of diversity during downstream processing such as purification of a recombinantly produced polyclonal protein.

The term "unique marker peptides" describes a number of peptides originating from the variable region of the individual members of a polyclonal protein. The peptides are preferably generated by protease treatment or other means of protein fragmentation, and the peptides which can be unambiguously assigned to a single individual member of the polyclonal protein are termed unique marker peptides.

DETAILED DESCRIPTION OF THE INVENTION

Figure 1:
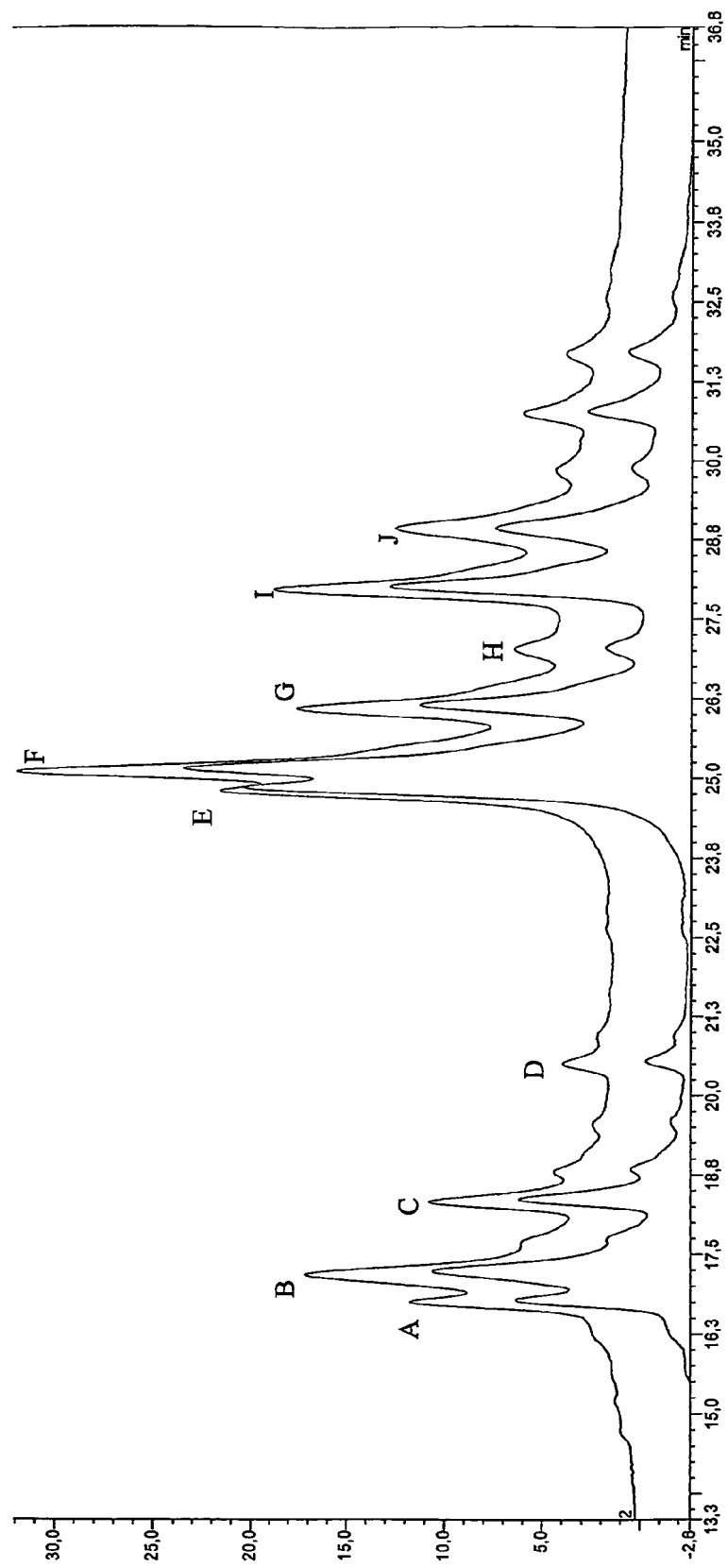
FIG. 1: Cation-exchange chromatograms of anti-RhD recombinant polyclonal antibody (anti-RhD rpAb) composition from aliquots 3948 and 3949 after 9 weeks cultivation. The lower diagram corresponds to aliquot 3949 and the upper one to aliquot 3948. The Y-axis of the top diagram has been displaced in order to separate it from the lower diagram. Peaks A-J comprise antibodies differing in net charge and individual antibodies appearing charge heterogeneous.

An aspect of the present invention is to provide a platform for structural characterization to obtain information with respect to the relative proportion of individual members in samples comprising (i) different homologous proteins having different variable regions or (ii) the cell lines producing such proteins. The characterization platform can be used to assess different aspects during a production or purification process or during long term storage of a composition comprising different homologous proteins. Preferably, the characterization platform of the present invention is used for one of the following purposes i) to determine the relative representation of the individual members or some of the individual members in relation to each other within a single sample, ii) to assess the relative proportion of one or more individual members in different samples for determination of the batch-to-batch consistency, and iii) to evaluate the actual proportion of one or more individual members. Optionally, this may be compared with the library of vectors originally used to generate the polyclonal manufacturing cell line. The characterization platform is particularly useful in monitoring the clonal diversity of a polyclonal cell line and/or the representation of individual proteins in a polyclonal protein produced by the cell line. Both the compositional stability during individual production runs and the batch-to-batch consistency can be monitored. Alternatively, the platform procedures can also be applied to purified compositions of different homologous protein mixtures, including a polyclonal protein or a mixture of monoclonal antibodies, for example to assess the long term stability of the individual members in such a composition.

One embodiment of the present invention is a procedure for characterizing samples comprising different homologous proteins having different variable regions or the cells producing such proteins, such that information is obtained with respect to the relative proportion or presence of the individual members of said proteins or their encoding sequences, said procedure comprising analyzing aliquots of said samples by one or more protein characterization techniques and/or by one or more genetic analyses of the protein-encoding sequences.

In a further embodiment of the present invention the structural characterization platform is comprised of a number of analytic techniques selected from protein characterization techniques as well as genetic analyses. Thus, the structural characterization platform can be composed of any number of the individual embodiments described in the following sections. It can be sufficient to obtain information about a sample from only one of the analytic techniques described in the embodiments. It is, however, preferable to obtain information from at least 2, 3, 4, 5, 6, 7, 8, 9, or 10 of these analytical techniques, thereby combining the individual embodiments set out below to generate the characterization platform. The combination of several analytical techniques allow for the generation of a more descriptive data set in relation to the relative or absolute composition of the polyclonal mixture. Information obtained from these techniques can be of a quantitative as well as a qualitative nature, that when compiled together provide an overall characterization of the samples analyzed.

In preferred embodiments of the present invention one analytic technique is a protein characterization technique and another analytic technique is a genetic analysis.

The genetic analyses refer to techniques such as restriction fragment length polymorphism (RFLP) analysis, terminal-RFLP (T-RFLP), microarray analysis, quantitative PCR such as real-time PCR, and nucleic acid sequencing.

The protein characterization techniques refer to techniques generally used within the field of proteomics for characterizing unknown proteins such as i) chromatographic analyses which separate proteins according to physico-chemical properties, ii) analysis of proteolytic digestions of the homologous proteins, iii) "bulk" N-terminal sequencing, and iv) analysis using specific detector molecules for the homologous proteins.

An additional concept of the present invention, which is applicable in combination with the analytical techniques described above, for the characterization of a complex pool of homologous proteins, has been developed in connection with the present invention. The concept is based on the selection of a number of sentinel proteins present in the pool of homologous proteins (e.g. a polyclonal antibody or a polyclonal TcR) or on the surface of the pool of cells producing the homologous proteins (e.g. a polyclonal manufacturing cell line). The sentinel proteins are quantitatively and qualitatively characterized to verify that this sub-population of proteins is present in a consistent manner, either in the supernatant of a polyclonal cell culture or on the cell surface during production. The sentinel proteins can for example be analyzed using detector molecules which are specific for individual members of the homologous proteins, e.g. such as anti-idiotype molecules. The sentinel protein concept can further be applied to assess the consistency between different cell culture batches. The concept of sentinel proteins can be extended to unique peptides derived from a polyclonal protein by protease treatment, such sentinel peptides preferably contain a part of the CDR if the polyclonal protein is a polyclonal antibody or TcR. Analyses performed at the genetic level can also apply the sentinel principle, based on unique nucleic acid sequences from individual members of the library encoding for the polyclonal protein. In particular the nucleic acid sequences corresponding to the CDR regions of antibodies or TcRs can be selected as sentinel nucleic acid sequences, most preferred is the CDR3 region. The sentinel proteins, peptides or nucleic acid sequences may vary for the individual analytical techniques, depending on which members of the polyclonal protein, or the nucleic acid sequences encoding it, can be distinguished with the selected analytic technique.

Genetic Analyses of the Clonal Diversity of a Polyclonal Manufacturing Cell Line In some embodiments of the present invention, the polyclonality in an expression system for producing a polyclonal protein is monitored by evaluating the quantity of cells encoding for a particular member of the polyclonal protein and/or the mRNA levels encoding for individual members of the polyclonal protein. This may be monitored at the mRNA or genomic level using for example RFLP or T-RFLP analysis, oligonucleotide microarray analysis, quantitative PCR such as real-time PCR, and nucleic acid sequencing of the variable regions of the gene sequences obtained from the manufacturing cell line. Alternatively, the same techniques can be used qualitatively to demonstrate the diversity of the polyclonal cell line. The nucleic acid sequences encoding the polyclonal protein can be monitored on samples obtained from a single polyclonal cell culture at different time points during the cultivation thereby monitoring the relative proportions of the individual encoding sequences throughout the production run to assess its compositional stability. Alternatively, the nucleic acid sequences encoding the polyclonal protein can be monitored on samples obtained from different polyclonal cell cultures at a particular time point thereby monitoring the relative proportions of the individual encoding sequences in different batches to assess batch-to-batch variation. Preferably the sample used in the genetic analyses is a cell culture fraction enriched for the cells of the culture, e.g. by precipitation. The sample is generally obtained by harvesting a fraction of the cell culture at a desired time point, followed by removal of the medium, for example by centrifugation. Samples for comparison of batch-to-batch consistency are preferably obtained from cells at the limit for in vitro cell age for production.

RFLP/T-RFLP

RFLP and T-RFLP analysis can be performed at the genomic level or the mRNA level. When a polyclonal manufacturing cell line is generated such that each cell only contains one copy of the sequence of interest, the analysis at the genomic level will provide information with respect to the relative proportion of cells within the manufacturing cell line that produce an individual member of the polyclonal protein. On the other hand analysis at the mRNA level will provide information regarding the potential expression levels of individual members of the polyclonal protein. Analysis at the mRNA level is generally performed by reverse transcribing the mRNA into cDNA prior to restriction analysis. It is, however, also possible to perform the analysis directly on the mRNA.

In the terminal-RFLP analysis the forward and/or reverse primer(s) used for the PCR or RT-PCR are labeled resulting in a terminal labeling of the PCR fragments. After digestion with appropriate restriction enzymes, fragments of different sizes are generated and can be separated by electrophoresis, preferably capillary electrophoresis, and the fragments can be detected through the label amplicon (Liu et al. 1997, Applied and Environmental Microbiology 63, 4516-4522). Suitable labels may provide signals detectable by fluorescence, radioactivity, colorimetry, X-ray diffraction or absorption, magnetism or enzymatic activity and include, for example, fluorophores, chromophores, radioactive isotopes (particularly $^{32}$P, $^{33}$P, $^{35}$S and $^{125}$I), electron-dense reagents, enzymes, and ligands having specific binding partners. Preferably, a fluorophore is used as label.

In a polyclonal manufacturing cell line with a large diversity, it may not be possible to obtain a unique restriction fragment for each individual encoding sequence. If such a situation arises, sentinel nucleic acid sequences can be selected for monitoring the clonal diversity of the polyclonal manufacturing cell line. Alternatively, the fragments which cannot be separated according to size may be sequenced in order to assess the distribution of all the individual encoding sequences.

Oligonucletide Microarray Analysis

Oligonucleotide microarrays, such as DNA chips, can be used to measure genomic DNA levels or mRNA levels in a polyclonal cell line by measuring hybridization of labeled DNA generated from the cell line, to a probe attached to a solid surface (Guo, Z. et al 1994. Nucleic Acids Res. 22, 5456-5465).

The probes can either be double-stranded cDNA sequences representative of the sequences expected to be present in the polyclonal cell line (either derived from the polyclonal cell line itself or from the DNA library used for transfecting the host cells comprising the polyclonal cell line) or sense oligonucleotides (20-90 nt in length). The probes are attached to a solid surface, such as glass, plastic or a gel matrix, and if a double stranded probe is used it is denatured prior to performing the assay. When analyzing a polyclonal cell line expressing homologous proteins, e.g. a polyclonal antibody or polyclonal TcR, it is preferred to use carefully designed oligonucleotide probes to prevent undesired cross-hybridization between the probe and labeled cDNA derived from the polyclonal cell line. Such probes are designed on the basis of alignment of the variable region encoding sequences that were used to generate the polyclonal manufacturing cell line in order to design specific probes for each individual member of the polyclonal product. For antibodies the encoding sequences will primarily differ in the CDR regions with the highest degree of variability in the CDR3 region. Regions with the greatest variability are preferably used for the design of sense oligonucleotide probes. The probes are preferably complementary in sequence to individual members comprised in the polyclonal cell line, and have as high a degree of dissimilarity to the other members as possible. One or more probes specific for each variable region can be used. For standardization purposes probes hybridizing with sequences in the constant region may be used. The probes are either spotted directly on the surface used for the hybridization or synthesized in situ on the surface (Pease et al. 1994. PNAS 91: 5022-5026, Singh-Gasson et al. 1999. Nature Biotech. 17: 974-978).

The labeled DNA to be analyzed is generated by harvesting the polyclonal cell population and preparing genomic DNA, total RNA or mRNA from the cells. When using genomic DNA the labeling is obtained either by using suitably labeled primers or labeled nucleotides in a PCR amplification of the relevant encoding sequences. When using total RNA or mRNA it is possible to obtain labeled cDNA by reverse transcription either alone or combined with a PCR step using labeled primers or nucleotides. Suitable labels may provide signals detectable by fluorescence, radioactivity, colorimetry, X-ray diffraction or absorption, magnetism or enzymatic activity and include, for example, fluorophores, chromophores, radioactive isotopes (particularly $^{32}$P, $^{33}$P, $^{35}$S and $^{125}$I), electron-dense reagents, enzymes, and ligands having specific binding partners. Preferably, a fluorophore is used as label. Where the encoding sequences to be analyzed are antibody heavy and light chains first-strand cDNA is prepared by reverse transcription by priming with anti-sense primers situated in the constant region 3' to the variable region. If no additional PCR is performed the synthesis is preferably performed with labeled nucleotides. If the reverse transcription is followed by PCR, a series of sense primers are applied which ensure that all the families of the variable regions are amplified. Alternatively, sense primers hybridizing to regions that are identical in all mRNAs (e.g. 5' untranslated region or the signal peptide-encoding sequence) can be used. The sense, and/or anti-sense primers can be fluorescently labeled or labeled nucleotides may be used in this approach.

When probes and labeled DNA have been prepared, the microarray assay is performed by hybridizing denatured labeled DNA to the immobilized oligonucleotides under conditions optimized for low noise and high specific signal. After washing, each of the hybridized probes is measured and the amount of specific message calculated.

Quantitative PCR

PCR methods have previously been adapted to provide both detection and quantification of nucleic acid sequences in a sample, see for example Higuchi, R. et al. 1993. Kinetic Biotechnology 11, 1026-1030; Holland, P. M. et al. 1991.

PNAS 88, 7276-7280; Livak, K. J. et al. 1995 PCR Methods Appl. 4, 357-362. These methods employ forward and reverse primers as in standard PCR plus one or more additional nucleic acid sequences that hybridize to the nucleic acid which shall be amplified. This additional nucleic acid sequence, termed a "probe", hybridizes to a portion of the nucleic acid to be amplified between the portions that hybridize to the two primers, and is labeled in such a way that each successive PCR cycle causes a change in the probe or its label. This change in the probe or its label causes activation or accentuation of the label to a degree that is related to the number of additional copies of the amplified nucleic acid during each PCR cycle. Such methods are generally referred to as "real-time" PCR, and provide a cycle-by-cycle detection of increasing PCR product by combining thermal cycling with label detection. In a particular version of the real-time PCR, the change in the probe or its label is caused by the exonuclease activity of the polymerase, e.g. the Taq polymerase, therefore this technique is generally referred to as Taq or TaqMan real-time PCR (e.g. Holland, P. M. et al. 1991. PNAS 88, 7276-7280).

Suitable labels may provide signals detectable by fluorescence, radioactivity, colorimetry, X-ray diffraction or absorption, magnetism or enzymatic activity and include, for example, fluorophores, chromophores, radioactive isotopes (particularly $^{32}P$, $^{33}P$, $^{35}S$ and $^{125}I$), electron-dense reagents, enzymes, and ligands having specific binding partners. Most commonly, the label for the probe is a fluorescent label which provides a fluorescent output signal. This may be achieved by providing a probe which is double-labeled with a fluorescent reporter dye at one end, typically the 5' end, and a quencher dye at the other, the 3', end (e.g. Livak, K. J. et al. 1995 PCR Methods Appl. 4, 357-362). When the probe is intact, the proximity of the quencher dye to the reporter dye suppresses the fluorescence of the reporter dye. Suitable dyes are reviewed in Wilhelm, J. and Pingoud, A., 2003. Chembiochem. 4, 1120-1128. During each PCR cycle, the 5'→3' exonuclease activity of a DNA polymerase cleaves the probe, which separates the reporter dye from the quencher dye. This separation results in increased fluorescence of the reporter dye.

During PCR, if the target of interest is present in a sample, the probe will anneal specifically between the forward and reverse PCR primer sites. The exonuclease activity of the DNA polymerase cleaves the probe between the reporter and the quencher dyes only if the probe hybridizes to the target molecule. These probes are often termed TaqMan probes. The increase in fluorescence is detected only if the target sequence is complementary to the probe and is amplified during PCR. Because of these requirements, non-specific amplification is not detected. Only amplified products that contain the sequence complementary to the probe are recognized by the presence of the fluorescent signal, thereby eliminating certain elements related to the analysis of false-positives. Additionally, one or more other enzymes may be utilized to help limit the amplification of carry-over transcription products.

This type of quantitative PCR permits the normalization of pipetting errors and volume changes, which may be done by dividing the reporter fluorescence by a passive reference, contained within each reaction, to determine the normalized reporter signal for each individual reaction. Software may be used to analyze the cycle-to-cycle increase in fluorescence intensity and compare these data to standards in order to determine starting copy numbers for absolute quantification or to compare against other unknown samples for a comparison of relative quantity.

In particular, the TaqMan real-time PCR in the present invention has been found to be suitable for the characterization of a polyclonal cell line. Thus, when applied to a cell line expressing a polyclonal antibody, the technique serves to quantify the relative proportions of the individual antibody encoding sequences, since a unique TaqMan probe can be designed for the heavy chain and/or light chain for each member represented in the polyclonal cell line. Preferably, one of the CDR regions, CDR1, CDR2 or CDR3, is selected for designing the TaqMan probe. Most preferably, the CDR3 region is selected for designing the TaqMan probe. Examples of such variable heavy chain CDR3 TaqMan probes can be found in Rasmussen, T. et al. 2000. Exp. Hematol. 28, 1039-1045, hereby incorporated by reference.

Nucleic Acid Sequencing

Nucleic acid sequencing is a well known technique, which can be utilized with the present invention to provide qualitative information with respect to the diversity of a polyclonal manufacturing cell line. The sequencing can either be performed on single cells derived from the polyclonal cell line by single-cell cloning or on an unprocessed sample of variant cells obtained from a polyclonal manufacturing cell line.

Sequencing on the single cell level will provide information with respect to the relative proportion of cells within the manufacturing cell line that produce an individual member of the polyclonal protein. In this procedure a sample from a polyclonal manufacturing cell line is obtained at a desired time point, and the cells encoding the polyclonal protein to be characterized are single-cell cloned, e.g. by using limited dilution or by a cell sorter such as a FACS Aria. The number of single cells which should be obtained from the polyclonal cell line sample depends on the variety of sequences expected to be represented within the cell line. Preferably, at least 3 times the number of individual encoding sequences forming the input during the cell line generation should be single cell sorted to give a 95% likelihood of re-finding all of them in the test sample. Thus, if a library of 25 different encoding sequences were used to generate the cell line, at least 75 single cell clones should be obtained from the sample for sequencing, given than the 25 different sequences are represented in equal amounts. This should ensure that most of the individual encoding sequences represented in the polyclonal cell line are represented among the single cells clones, if they have not been lost during the manufacturing process. The single cells are grown to confluence in separate wells and aliquots from each well are used as template in nucleic acid sequencing reactions. The sequencing may be performed at the mRNA level or the genomic level, using an RT-PCR or a PCR amplification step, respectively, prior to the sequencing. Sequence information obtained either on the mRNA or genomic level can determine the percentage of cells encoding each of the individual antibody components. Further, the sequence information obtained at the mRNA level can be used to assess the expression level of each of the individual antibodies in the polyclonal composition. In addition to the sequencing it is possible to perform a TaqMan real time PCR on the mRNA level to obtain information with respect to the potential expression level of the single cell clone. The RFLP or T-RFLP analyses previously described can likewise be performed on the single cell level.

Sequencing on an unprocessed sample of variant cells obtained from a polyclonal manufacturing cell line can also provide information with respect to the potential expression level of an individual member of the polyclonal protein produced from the cell line, based on the relative mRNA level of the encoding sequences of the individual members of polyclonal protein. In this procedure a sample from a polyclonal manufacturing cell line is obtained at a desired time point.

RT-PCR is performed directly on the lysed cells within the sample. The primer set applied for the RT-PCR reaction is designed in such a way that it will be expected to amplify all the encoding sequences with the same efficiency if the sense and anti-sense primers hybridize to regions that are identical in all mRNAs (e.g. a sense primer in the 5' untranslated region or in the signal peptide encoding sequence and an anti-sense primer in the constant region sequence can be used). The amplified PCR fragments are cloned into a sequencing vector and transfected into a host cell, preferably *E. coli*. Plasmid DNA from single colonies representing an individual encoding sequence from the polyclonal manufacturing cell line is sequenced, the proportion of the individual encoding sequences obtained will reflect the mRNA level of each individual encoding sequence in the polyclonal cell line as well as the potential expression level of the individual protein members.

In a further embodiment of the present invention, the genetic analyses described above are applied as separate analyses. Preferably, one or more of the analyses are performed on aliquots from the same sample, in order to obtain as much information on the clonal diversity of the cell line as possible. The genetic analyses can alternatively be combined in a multidimensional manner, for example micro array analyses can be performed on the RFLP or T-RFLP fragments after this analysis, or the RFLP fragments can be sequenced subsequent to the RFLP analysis. In particular it is an advantage to perform sequencing on RFLP fragments which represent more than one individual component, and which cannot be separated due to their identical restriction fragment size.

Protein Characterizing Techniques for Assessing Polyclonality

In embodiments of the present invention, the polyclonality of a pool of homologous proteins or the expression system for producing the homologous proteins is monitored by one or more protein characterization techniques. Protein characterization techniques refer to any technique that alone or in combination with other techniques is capable of providing information with respect to the presence and relative proportion of the individual members of a mixture of monoclonal proteins or a recombinant polyclonal protein in solution or on the surface of a cell present in a polyclonal cell line. Depending on the complexity of the recombinant polyclonal protein one or more of the following techniques may be used: i) chromatographic separation techniques, ii) analysis of proteolytic digests of the polyclonal protein for identification of unique marker peptide representing individual members of the polyclonal protein, iii) "bulk" N-terminal sequencing, and iv) analysis using specific detector molecules, e.g. for characterization of sentinel protein members of the polyclonal protein.

The sample containing the different homologous proteins can be a mixture of purified monoclonal proteins, or a polyclonal protein. The polyclonal protein can for example be derived from a cell culture supernatant obtained from a polyclonal cell culture, e.g. in the form of a "raw" supernatant which only has been separated from cells e.g. by centrifugation, or supernatants which have been purified, e.g. by protein A affinity purification, immunoprecipitation or gel filtration. These pre-purification steps are, however, not a part of the characterization of the recombinant polyclonal protein since they do not provide any separation of the different homologous proteins in the composition. Preferably, the sample subjected to the characterization process of the present invention has been subjected to at least one purification step. Most preferred are samples which comprise 90%, 95% or 99% pure homologous proteins.

The different homologous proteins constituting the polyclonal protein can be monitored on samples obtained from a single polyclonal cell culture at different time points during the cultivation thereby monitoring the relative proportions of the individual polyclonal protein members throughout the production run to assess its compositional stability. Alternatively, different homologous proteins constituting the polyclonal protein can be monitored on samples obtained from different polyclonal cell cultures at a particular time point thereby monitoring the relative proportions of the individual encoding sequences in different batches to assess batch-to-batch consistency.

Chromatographic Separation Techniques

Chromatographic separation of the individual members of the polyclonal protein may be based on differences in physico-chemical properties such as i) net charge (exemplified by ion-exchange chromatography (IEX)), ii) hydrophobicity (exemplified by reverse-phase chromatography (RP-HPLC), and hydrophobic interaction chromatography based on salt concentration (HIC)), iii) isoelectric points (pI values) (exemplified by chromatofocusing) or iv) affinity (exemplified by affinity chromatography using anti-idiotype peptides/antibodies, or protein-L chromatography for the separation of Kappa and Lambda antibody light chains). A fifth well known chromatographic technique, is based on the following physico-chemical property: Size. This is, however, not a particularly suitable technique for characterization of homologous proteins such as a polyclonal antibody or polyclonal TcR, since all the members are of essentially the same size. Separation by size can be omitted completely from the characterization platform. Some of these abovementioned chromatographic techniques have been employed in separation of immunoglobulin classess such as IgA, IgG and IgM (Gallo, P. et al. 1987. J. Chromatogr. 416, 53-62) or sub-classess such as, IgG1, IgG2, IgG3 (Scharf, O et al. 2001. J. Virol. 75, 6558-6565) from for human serum. However, separation with respect to the diversity of the individual antibodies in a serum-derived immunoglobulin or a recombinant polyclonal antibody has not previously been performed.

a) Ion-Exchange Chromatography

In embodiments of the present invention ion-exchange chromatography is used to separate individual members of a recombinant polyclonal protein or a sub-population of individual members of a polyclonal protein. The separation by ion-exchange chromatography is based on the net charge of the individual proteins in the composition to be separated. Depending on the pI-values of the recombinant polyclonal protein, the pH values and salt concentrations of the chosen column buffer, the individual members of the recombinant polyclonal protein can be separated, at least to some extent, using either anion or cation-exchange chromatography. For example, all the individual members of a recombinant polyclonal protein will normally bind to a negatively charged cation-exchange media as long as the pH is well below the lowest pI-value of the individual members of the recombinant polyclonal protein composition. The individual members of the bound recombinant polyclonal protein can subsequently be eluted from the column dependent of the net charge of the individual proteins using typically an increasing gradient of a salt (e.g. sodium chloride) or an increasing pH value. Several fractions will be obtained during the elution. A single fraction preferably contains an individual member of the polyclonal protein, but may also contain 2, 3, 4, 5, 6, 7, 8, 9, 10, 15, 20 or more distinct members of the polyclonal protein. The general principles of cation and anion-exchange are well known in the art, and columns for ion-exchange chromatography are commercially available.

b) Chromatofocusing

In further embodiments of the present invention chromatofocusing is used to separate individual members of a recombinant polyclonal protein or a sub-population of individual members of a polyclonal protein. The separation by chromatofocusing is based on differences in the pI values of individual proteins and is performed using a column buffer with a pH value above the pI value of the recombinant polyclonal protein. A recombinant polyclonal protein where the individual members have relatively low pI values will bind to a positively charged weak anion-exchange media. The individual members of the bound recombinant polyclonal protein can subsequently be eluted from the column dependent on the pI values of the individual members by generating a decreasing pH gradient within the column using a polybuffer designed to cover the pH range of the pI values of the individual members. Several fractions will be obtained during the elution. A single fraction preferably contains an individual member of the polyclonal protein, but may also contain 2, 3, 4, 5, 6, 7, 8, 9, 10, 15, 20 or more distinct members of the polyclonal protein. The general principles of chromatofocusing anion-exchangers are well known in the art, and anion columns are commercially available. Chromatofocusing with cation-exchangers is also known in the art (Kang, X. and Frey, D. D., 2003. J. Chromatogr. 991, 117-128, hereby incorporated by reference).

c) Hydrophobic Interaction Chromatography

In further embodiments of the present invention hydrophobic interaction chromatography is used to separate individual members of a recombinant polyclonal protein or a sub-population of individual members of a polyclonal protein. The separation by hydrophobic interaction chromatography is based on differences in hydrophobicity of the individual proteins in the composition to be separated. The recombinantly produced polyclonal protein is bound to a chromatography media modified with a hydrophobic ligand in a buffer that favors hydrophobic interactions. This is typically achieved in a buffer containing a low percentage of organic solvent (RP-HPLC) or in a buffer containing a fairly high concentration of a chosen salt (HIC). The individual members of the bound recombinant polyclonal protein will subsequently be eluted from the column dependent of the hydrophobicity of the individual members typically using an increasing gradient of organic solvent (RP-HPLC) or decreasing gradient of a chosen salt (HIC). Several fractions will be obtained during the elution. A single fraction preferably contains an individual member of the polyclonal protein, but may also contain 2, 3, 4, 5, 6, 7, 8, 9, 10, 15, 20 or more distinct members of the polyclonal protein. The general principles of hydrophobic interaction chromatography are well known in the art, and columns for RP-HPLC as well as HIC are commercially available.

d) Affinity Chromatography

In further embodiments of the present invention affinity chromatography is used to separate individual members of a polyclonal protein or a sub-population of individual members of a polyclonal protein. The separation by affinity chromatography is based on differences in affinity towards a specific detector molecule, ligand or protein. The detector molecule, ligand or protein or a plurality of these (these different options are just termed ligand in the following) are immobilized on a chromatographic medium and the recombinant polyclonal protein is applied to the affinity column under conditions that favors interaction between the individual members and the immobilized ligand. Proteins showing no affinity towards the immobilized ligand are collected in the column flow through and proteins showing affinity towards the immobilized ligand are subsequently eluted from the column under conditions that disfavors binding (e.g. low pH, high salt concentration or high ligand concentration). Several fractions can be obtained during the elution. A single fraction preferably contains an individual member of the polyclonal protein, but may also contain 2, 3, 4, 5, 6, 7, 8, 9, 10, 15, 20 or more distinct members of the polyclonal protein. The ligands which can be used to characterize a recombinant polyclonal protein are for example target-antigens, anti-idiotype molecules, or protein L for the separation of antibodies with Kappa or Lambda light chains.

Affinity chromatography with target-antigens will be particular relevant where a recombinant polyclonal protein comprises affinities towards more than one epitope. The target may for example be a cancer cell or a virus or a combination of targets, which contain many epitopes. These epitopes can be synthesized synthetically and immobilized on a chromatographic medium. The assay can be designed with one epitope per column or several different epitopes per column, thereby allowing for characterization of the recombinant polyclonal protein mixture with respect to the distribution of individual members towards the particular epitopes. Alternatively, the complete antigens or target molecules can be immobilized on a chromatographic medium.

Affinity chromatography with anti-idiotype molecules (e.g. anti-idiotype peptides or anti-idiotype antibodies) which specifically bind to individual members of a polyclonal protein or a sub-population of such individual members can be performed to obtain information with respect to the relative proportion of selected members of the recombinant polyclonal protein (also termed sentinel proteins), or a sub-population of individual members. Ideally, each individual anti-idiotype molecule only binds specifically to one individual member, but not to other members of the recombinant polyclonal protein, although an anti-idiotype molecule which binds a defined sub-set of members also is applicable in the present invention. Preferably, anti-idiotype molecules are generated towards all the individual members, such that the complete polyclonal composition can be characterized. Where the recombinant polyclonal protein is a polyclonal antibody or TcR, the anti-idiotype molecules are directed against the antigen-specific part of the sequence of an antibody or a T cell receptor. The anti-idiotype molecules can be immobilized to the chromatographic medium individually, such that one column contains one anti-idiotype molecule, whereby information about a particular protein member or sub-population of proteins is obtained. The flow-through can then be applied to a second column with a second immobilized anti-idiotype molecule and so forth. Alternatively, several different anti-idiotype molecules are immobilized on the same chromatographic medium applied to the same column. Elution is then performed under conditions that allow for the individual proteins to be eluted in different fractions, e.g. by adding increasing amounts of free idiotype molecules to the column, or using a pH or salt gradient. With this approach, it will be possible to obtain information on the proportions of several members of the polyclonal protein with a one dimensional analysis.

Where the recombinant polyclonal protein is a polyclonal antibody, this may be composed of individual members which either contain a Kappa light chain or a Lambda light chain. In such a polyclonal antibody, the antibodies with a Lambda light chain may be separated from the antibodies with a Kappa light chain by using the lack of affinity towards Protein L for Lambda light chain antibodies. Thus, a subset of antibody members containing the Lambda light chain can be separated from a subset of antibody members containing the Kappa light chain using Protein L affinity chromatography. The Kappa and Lambda antibody subsets can subsequently be characterized further using alternative chromatographic techniques for individual antibody quantification e.g. as described above.

Multidimensional Chromatography

Depending on the complexity of the variant homologous proteins in the sample to be analyzed, e.g. a recombinant polyclonal protein, it may be desirable to combine two or more of the chromatographic techniques described above in a) to d) in a two-dimensional, three-dimensional or multidimensional format. It is preferred to use liquid chromatography in all the dimensions instead of two-dimensional gel electrophoresis. This does, however, not exclude the use of gel electrophoresis or precipitation techniques in one or more dimensions for the characterization of a recombinant polyclonal protein.

Liquid two-dimensional chromatography has been described in for example Lubman, D. M. et al. 2002. J. Chromatogr. B Analyt. Technol. Biomed. Life Sci. 782, 183-196; WO 01/58925 and WO 01/58926. The method has been used to compare protein expression of healthy cells and cancer cells, thereby generating a differential display at the protein-level. Further, three-dimensional chromatography, where the third dimension is separation by size, has been described in WO 03/102539 for the separation of proteins in for example cell extracts, thereby likewise generating a differential display.

In further embodiments of the present invention multidimensional chromatography is used for the characterization of different homologous proteins within a sample. In particular samples of homologous proteins having different variable regions, such as antibodies and T cell receptors are characterized with multidimensional chromatography. Preferably, the additional dimension is performed on the fractions obtained during elution in the preceding dimension. However, the flow-through can also be used for further dimensional analysis. This may in particular become relevant when the preceding dimension is affinity chromatography.

In one embodiment of the present invention multidimensional chromatography is used in the separation of individual antibody molecules with respect to their diversity, either from a polyclonal antibody (serum-derived immunoglobulin or recombinant) or a mixture of monoclonal antibodies. Preferably the multidimensional chromatography is liquid chromatography.

In another embodiment of the present invention multidimensional chromatography is used in the separation of individual T cell receptor molecules with respect to their diversity, either from a polyclonal T cell receptor or a mixture of monoclonal T cell receptors. Preferably the multidimensional chromatography is liquid chromatography.

Generally, it is attempted to use chromatographic techniques based on different physico-chemical properties in the different dimensions in a multidimensional chromatography, e.g. separation by charge in the first dimension and separation by hydrophobicity in the second dimension and affinity in the third dimension. However, some chromatographic techniques can provide additional separation when used in a subsequent dimension, even if they exploit similar physico-chemical properties of the protein. For example additional separation can be obtained when chromatofocusing is followed by ion-exchange chromatography or affinity chromatography with different ligands succeed each other.

Table 1 lists up to five dimensions, in which chromatographic techniques can be employed as a part of the characterization platform of the present invention. This should, however, not be considered as a mandatory number of dimensions. If a sufficient separation, to characterize the recombinant polyclonal protein, has been obtained after one, two, three or four dimensions, the remaining dimensions can be omitted. Hence, if sufficient separation is obtained with ion-exchange chromatography (IEX), it is not necessary to perform chromatofocusing, RP-HPLC, and so forth. If on the other hand five dimensions prove insufficient, additional dimensions can be added. Further, Table 1 should not be considered as an exhaustive list of possible combinations of chromatographic techniques, or as an exhaustive list of the techniques themselves.

TABLE 1

| $1^{st}$ dimension | $2^{nd}$ dimension | $3^{rd}$ dimension | $4^{th}$ dimension | $5^{th}$ dimension |
|---|---|---|---|---|
| IEX | Chromatofocusing | RP-HPLC/HIC | Protein L affinity | Anti-idiotype affinity |
| IEX | RP-HPLC/HIC | Protein L affinity | Anti-idiotype affinity | |
| IEX | RP-HPLC/HIC | Anti-idiotype affinity | Protein L affinity | |
| IEX | Protein L affinity | Anti-idiotype affinity | RP-HPLC/HIC | |
| IEX | Protein L affinity | RP-HPLC/HIC | Anti-idiotype affinity | |
| IEX | Anti-idiotype affinity | Protein L affinity | RP-HPLC/HIC | |
| IEX | Anti-idiotype affinity | RP-HPLC/HIC | | |
| Chromatofocusing | IEX | RP-HPLC/HIC | Protein L affinity | Anti-idiotype affinity |
| Chromatofocusing | RP-HPLC/HIC | Protein L affinity | Anti-idiotype affinity | |
| Chromatofocusing | RP-HPLC/HIC | Anti-idiotype affinity | | |
| Chromatofocusing | Protein L affinity | RP-HPLC/HIC | Anti-idiotype affinity | |
| Chromatofocusing | Protein L affinity | Anti-idiotype affinity | RP-HPLC/HIC | |
| Chromatofocusing | Anti-idiotype affinity | Protein-L affinity | RP-HPLC/HIC | |

TABLE 1-continued

| 1st dimension | 2nd dimension | 3rd dimension | 4th dimension | 5th dimension |
|---|---|---|---|---|
| HIC | IEX/chromatofocusing | Protein-L affinity | Anti-idiotype affinity | |
| HIC | Protein L affinity | IEX/chromatofocusing | Anti-idiotype affinity | |
| HIC | Protein L affinity | Anti-idiotype affinity | IEX/chromatofocusing | |
| HIC | Anti-idiotype affinity | IEX/chromatofocusing | RP-HPLC/HIC | |
| Protein L affinity | RP-HPLC/HIC | IEX/chromatofocusing | Anti-idiotype affinity | |
| Protein L affinity | IEX/chromatofocusing | RP-HPLC/HIC | Anti-idiotype affinity | |
| Protein L affinity | Anti-idiotype affinity | IEX/chromatofocusing | RP-HPLC/HIC | |
| Protein L affinity | Anti-idiotype affinity | RP-HPLC/HIC | IEX/chromatofocusing | |
| Anti-idiotype affinity | IEX/chromatofocusing | RP-HPLC/HIC | Protein L affinity | |
| Anti-idiotype affinity | RP-HPLC/HIC | IEX/chromatofocusing | Protein L affinity | |
| Anti-idiotype affinity | Protein L affinity | IEX/chromatofocusing | RP-HPLC/HIC | |
| Anti-idiotype affinity | Protein L affinity | RP-HPLC/HIC | IEX/chromatofocusing | |

In preferred embodiments of the present invention, the multidimensional liquid chromatography (LC) is a two-dimensional LC technique selected from the first two dimensions shown in Table 1.

In further preferred embodiments of the present invention, the multidimensional LC is a three-dimensional LC technique selected from the first three dimensions shown in Table 1.

As an alternative to multidimensional LC techniques, immunoprecipitation combined with a suitable electrophoresis technique, such as gel electrophoresis or capillary electrophoresis, and subsequent quantification of the antigens can be used to characterize a recombinant polyclonal protein. This technique will be particularly useful to characterize a recombinant polyclonal antibody targeted against complex antigens. A recombinant polyclonal antibody targeted against e.g. a complex virus antigen can be immunoprecipitated using a labeled antigen mixture and protein A beads. The antigens could subsequently be separated using isoelectric focusing or 2D PAGE followed by quantification of the individual antigens, reflecting the amount of antibodies in a recombinant polyclonal antibody targeted against the specific antigens.

Elimination of N-Terminal Charge Heterogeneity in Recombinant Proteins

In the protein characterization techniques described in the above, heterogeneity of the individual protein in a pool of homologous proteins may complicate the characterization even further, since a single protein may result in several peaks in for example an IEX profile. Heterogeneity is a common phenomenon in antibodies and other recombinant proteins, and is due to enzymatic or non-enzymatic post translational modifications. These modifications may cause size or charge heterogeneity. Common post-translational modifications include N-glycosylation, methionine oxidation, proteolytic fragmentation, and deamidation. Heterogeneity can also originate from modifications at the genetic level, such as mutations introduced during transfection (Harris, J. R, et al. 1993. Biotechnology 11, 1293-7) and crossover events between variable genes of heavy and light chains during transcription (Wan, M. et al. 1999. Biotechnol Bioeng. 62, 485-8). These modifications are epigenetic and thus not predictable from the genetic structure of the construct alone.

Some of these post-translational modifications which may result in heterogeneity may be dealt with prior to characterization. Charge variation arising from enzymatic removal of C-terminal lysine can be solved by the use of specific carboxypeptidase inhibitors or treating the antibody with carboxypeptidase to simplify the overall pattern (Perkins, M. et al. 2000. Pharm Res. 17, 1110-7). Size variation arising from differences in the glycosylation patterns, may also be dealt with by enzymatic deglycosylation using for example PNGase F, Endo H, O-Glycosidase or Neuraminidase.

Chemical degradation of proteins, such as deamidation has been shown to be a significant problem during production and storage and result in charge heterogeneity. Deamidation of Asn to Asp and formation of isoAsp (isoaspartyl peptide bonds) take place under mild conditions (Aswad, D. W. et al. 2000. J Pharm Biomed Anal. 21, 1129-36). These rearrangements occur most readily at Asn-Gly, Asn-Ser, and Asp-Gly sequences where the local polypeptide chain flexibility is high.

Figure 16:
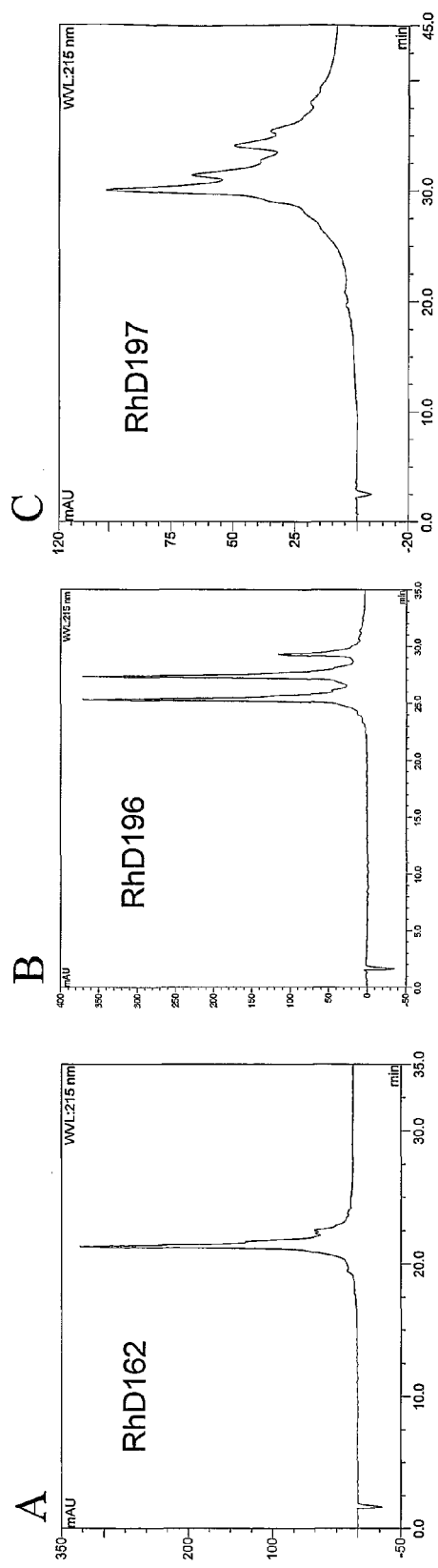
FIG. 16: IEX profiles of three representative monoclonal anti-RhD antibodies showing three different charge patterns. (A) homogeneous, (B) "3 peaks" pattern, (C) complex pattern.

Another cause of charge heterogeneity may result from the N-terminal blockage by pyroglutamic acid (PyroGlu) resulting from cyclization of N-terminal glutamine residues (deamidation). Such post-translational modifications have been described for IgG as well as other proteins. Partially cyclization of the N-terminal of an antibody, especially if both HC and LC are involved, will result in charge heterogeneity giving a complex IEX pattern. Potential IEX patterns due to the formation of an N-terminal PyroGlu on one or more of the VH and VL chains of an antibody are shown in FIG. 16. If a sample comprising different homologous proteins having different variable regions, such as a recombinant polyclonal antibody, is to be characterized by techniques based on the net-charge, it is obvious that such an analysis will be complicated even if just a few of the sample components have IEX patterns as shown in FIGS. 16B and C, since this will mask the clonal diversity in an IEX profile of for example a polyclonal antibody composition. This problem cannot be solved by the use of the specific enzyme, pyroglutamate aminopeptidase, first of all because the deblocking has to be performed on reduced and alkylated antibodies in order to obtain high yields of the deblocked antibodies (Mozdzanowski, J. et al. 1998 Anal Biochem. 260, 183-7) not compatible with a subsequent IEX analysis, and second because it will not be possible to obtain a 100% cleavage for all the antibodies.

A further aspect of the present invention therefore relates to the elimination of charge heterogeneity caused by cyclization of N-terminal glutamine residues. This aspect of the invention is particular useful if combined with any of the previously described characterization tools, which are based on the physico-chemical property net charge, e.g. IEX chromatography and chromatofocusing. The formation of N-terminal PyroGlu residues is eliminated by ensuring that no polypeptide chain contains a N-terminal glutamine, e.g. by changing said N-terminal glutamine residue to another amino acid. If the protein is a heteromeric protein composed different subunits, preferably all N-terminal Gln residues are exchanged for other residues. For antibodies Gln residues at the N-terminal of the heavy chain and/or the light chain are exchanged. This is done by site-directed mutagenesis of nucleic acid sequences which encode polypeptides with an N-terminal glutamine. Preferably, the N-terminal glutamine residues are replaced by glutamic acid residues, since this is the uncharged derivative of glutamine. In a recombinant polyclonal protein, the individual sequences encoding for the members must be changed and re-inserted into an expression vector to generate a new cell line expressing the changed protein. This cell line can then be included into the collection of cells producing the polyclonal protein.

Analysis of Proteolytic Digestions of the Variable Region of Homologous Proteins A protein sample comprising different homologous proteins having different variable regions can, as described in the above, be characterized based on the physico-chemical properties of the intact proteins using a range of chromatographic techniques. The information obtained from these previously described analyses can additionally be supplemented with information obtained from analysis of proteolytic digestions of the homologous proteins. Preferably, the proteolytic digestion is performed on an aliquot of the same sample as the chromatographic analyses of the intact proteins were performed on.

In further embodiments of the present invention, identification of unique marker peptides originating from the variable region of the individual members of a composition of homologous proteins is used to characterize the protein composition for the presence of the individual members in a qualitative manner. These unique marker peptides are generated by proteolytic digestion of the protein composition (sample) comprising the different homologous proteins.

In order to perform peptide mapping of the variable regions of a mixture of homologous proteins, it is important that the part or parts of the variable regions which differentiate the individual members within the mixture from the other members are kept intact after the proteolytic digestion. Hence, one or more proteases should be selected such that at least one unique sequence, also termed a marker peptide, can be obtained for each individual member of a recombinant polyclonal protein. Where the mixture of homologous proteins is a recombinant polyclonal antibody or recombinant polyclonal TcR, the sequences which differentiate the individual members from each other are normally characterized by the CDR regions. The choice of protease, proteases or chemical compounds used to generate the unique marker peptides is based on an analysis of the protein sequences constituting the sample of homologous protein. Generally, the proteases or a chemical compounds should cleave at defined sites in the protein with high specificity. Such cleavage-specific proteases are well known in the art and can for example be trypsin, endo Glu-C, lysyl endopeptidase, endo Arg-C, endo Asp-N or endo Asn-C. These are merely examples and should not be considered as limiting to this embodiment.

When a polyclonal protein sample is digested with one or more selected proteases, a pool of peptides originating both from the constant and the variable regions from all the individual members will be generated. A proportion of the unique marker peptides will show differences in their physico-chemical properties compared to the main population of peptides originating from the constant regions. The unique marker peptides can therefore be isolated using one of the chromatographic techniques described in the above. Preferably, ion-exchange chromatography or RP-HPLC specifically designed for peptide separation is used to separate the unique peptides from the major fraction of constant region peptides. Multidimensional chromatographic techniques as previously described can likewise be applied to separate the unique marker peptides. Following separation in one or more dimensions, mass spectrometry (MS) can be used for identification of the different peptides. MS techniques known by the skilled person within the field of proteomics can be used for the identification of the peptides. Preferred MS techniques are matrix-assisted UV laser desorption/ionization (MALDI) time-of-flight (TOF) mass spectrometry, and electrospray ionization time-of-flight (ESI-TOF) mass spectrometry.

Alternatively, proteolytic digestion can be performed on intact proteins separated by one dimensional or multidimensional chromatography as described in a) to d) and in the "Multidimensional liquid chromatography" section above, followed by proteolytic cleavage of the separated protein fractions. These digests can then be analyzed by MS (Kachman, M. T. et al. 2002. Anal. Chem. 74, 1779-1791). This approach can be an advantage for characterization of very complex polyclonal proteins, since it can be applied selectively to a proportion of the fractions obtained by one dimensional or multidimensional analysis of the intact proteins in order to characterize these further.

Proteolytic digestion can furthermore be performed in order to isolate N-terminal marker peptides, if these contain unique variable regions. The N-terminal peptides can be isolated as essentially described in Gevaert, K. et al., 2003. Nat. Biotechnol. 21, 566-569, hereby incorporated by reference. Briefly, the free amino groups in the recombinant polyclonal protein are blocked, e.g. by acetylation, and the protein mixture is subsequently digested with a suitable protease. The digestion generates a free N-terminal amino group on internal peptides which are subsequently blocked with a compound allowing separation of internal peptides from N-terminal peptides. Such compounds can be i) 2,4,6-trinitrobenzenesulfonic acid (TNBS) as described by Gevaert which allow for isolation by hydrophobic interactions ii) biotin, followed by subsequent removal after binding to immobilized streptavidin, or iii) pre-activated matrices (e.g. NHS-activated, CNBr-activated, ECH Sepharose material, or UltraLink bis-acrylamide support with Azlactone groups) followed by centrifugation whereby the bound internal peptides are separated from the acetylated N-terminal peptides, which are present in the supernatant. Isolated acetylated N-terminal peptides can subsequently be analyzed by one dimensional or multidimensional liquid chromatography combined with MS analysis as described in the above. Alternatively, the N-terminals of the intact proteins are blocked with a compound that allow for their specific separation and the internal peptides generated after cleavage are acetylated or blocked with a second compound.

Additionally, identification of unique marker peptides following proteolytic digestion can be performed using characteristic amino acid side chain functionality. One or a combination of different affinity techniques that captures peptides containing specific amino acid residues with and without relevant amino acid side chain modification can be used. Peptides containing e.g. cysteine, methionine, tryptophan, histidine, and tyrosine can be purified using column material or beads immobilized with specific affinity tags that captures peptides containing these amino acid residues (Bernhard, O. K. et al. 2003. Proteomics 3, 139-146; Chelius, D. and Shaler, T. A., 2003. Bioconjug. Chem. 14, 205-211; Gevaert, K. et al. 2002. Mol. Cell Proteomics 1, 896-903; Gygi, S. P. et al., 1999. Nat. Biotechnol 17, 994-999). Unique variable region peptides containing a cysteine and a tyrosine can for example be captured on a streptavidin column following biotinylation of the cysteine residue and subsequently after elution of the cysteine containing peptides these can be applied to either a column or beads that specifically binds tyrosine residues. This peptide capture based on affinity to specific amino acid residues can be performed as an additional dimension to the previously described chromatographic techniques like RP-HPLC and ion-exchange chromatography. First, the chromatographic techniques are applied to a proteolytic digest of the recombinant polyclonal protein in one or more dimensions, then the amino acid-specific capture is performed on one or more fractions in a final dimension followed by analysis by MS. The isolation of peptides based on side chain functionality can further be performed in combination with the N-terminal peptide isolation technique.

Where the recombinant polyclonal protein to be analyzed by proteolytic digestion followed by peptide isolation is a multimeric protein, separation of the subunits is preferably performed prior to the proteolysis in order to simplify the "fingerprinting" of the proteolytic digest. This can for example be performed by reduction and alkylation of the free cysteine residues followed by gelfiltration to separate the subunits, e.g. separation of heavy chains from light chain or alpha chains from beta chains if the polyclonal protein is an antibody or TcR, respectively. Alternatively, proteolytic digestion can be performed under native conditions. Particularly for antibodies this can be a suitable alternative, since the quaternary structure of an antibody leads to a high resistance to proteolytic cleavage within the constant regions. Thus, proteolytic cleavage of an intact non-reduced polyclonal antibody is likely to generate peptides primarily from the variable regions.

The proteolytic digestion techniques described above can also be applied according to the sentinel concept, by selecting sentinel peptides which can be characterized within a proteolytic digest.

"Bulk" N-Terminal Sequencing

As described, N-terminal sequences can be isolated and used for fingerprinting a proteolytic digest of a polyclonal protein. Alternatively, the N-terminal sequence can be sequenced directly from the intact protein, thereby omitting the proteolytic step. "Bulk" N-terminal sequence analysis of a protein sample comprising different homologous proteins having different variable regions can be used to compare purified batch products of for example a recombinant polyclonal protein. Where the polyclonal protein is a recombinant polyclonal antibody or TcR the "bulk" N-terminal sequencing is preferably performed on pools of separated heavy and light chains or separated alpha and beta chains, respectively. In a pool of for example homologous heavy chains some amino acid positions may be completely conserved whereas other positions may vary, this can be assessed by alignment of the amino acid sequences. Thus, several different amino acids may be obtained during particular rounds of sequencing. For example, position four may be represented by five different amino acids in a polyclonal sample, as predetermined by alignment of the homologous sequences. During the "bulk" N-terminal sequence analysis these varying amino acids can be quantitated and the different amounts of individual amino acids representing e.g. position four in a recombinant polyclonal antibody can be used to compare the relative composition of different samples.

Characterization of Complex Homologous Protein Mixtures with Specific Detector Molecules The characterization platform of the present invention further employ specific detector molecules, where each specific detector molecule is capable of identifying an individual protein member within a complex mixture of homologous proteins, thereby assisting in monitoring the presence of the particular member in a sample. Specific detector molecules can for example be specific ligands such as small organic molecules, peptides or proteins with specificity for an individual member of a polyclonal protein. In particular, ligand-peptides or proteins such as anti-idiotype peptides or anti-idiotype antibodies are preferred embodiments of the present invention. A detector molecule which binds a defined sub-set of the complex mixture of homologous proteins is also applicable in the present invention.

Specific detector molecules can be used to characterize complex mixtures of homologous proteins by, i) allowing for determination of concentrations or relative proportion of one or more individual proteins in a sample comprising a complex mixture of homologous proteins, ii) acting as an additional dimension in chromatographic analyses, iii) allowing for determination of concentrations of individual proteins in samples obtained during fermentation of a complex mixture of homologous proteins, and iv) allowing for determination of individual protein producing cells in a polyclonal cell line, such as a working cell bank or a bioreactor cell sample, expressing a mixture of homologous proteins. Step iv) can either be performed on a polyclonal cell line or on single cells distributed into single tubes from a polyclonal cell line followed by a subsequent cultivation period.

For generation of specific peptide-ligands capable of identifying individual protein members within a complex mixture of homologous proteins, vast libraries of filamentous phage expression vectors that display foreign oligomeric peptides on the virion surface can be screened by affinity, followed by purification of the phages which display a foreign peptide that binds to an antibody, TcR or another desired individual protein member (Scott and Smith 1990. Science 249, 386-90). EP 1 106 625 in particular describes the generation of peptides capable of binding to anti-RhD antibodies for immunization purposes. The displayed peptide libraries are approximately between 5 and 50 amino acids long, and preferably between 7 and 20 amino acids long, even more preferred between 8 and 15 amino acids long and most preferred between 9 and 12 amino acids long. When the relevant peptides have been identified, they can be synthesized.

The generation of anti-idiotype antibodies is generally known in the art. Briefly, mice are immunized with the antibody towards which anti-idiotype antibodies are desired. Monoclonal antibodies are generated from immunized mice, which are screened for production of an anti-idiotype antibody with the desired specificity using for example hybridoma technology or phage display. Anti-idiotype peptides or anti-idiotype antibodies should be characterized with respect to specificity and potential cross-reactivity. This analysis will verify whether an anti-idiotype peptide or anti-idiotype antibody recognize a specific member or alternatively recognize a subset of closely related members within a polyclonal protein (for antibodies, related members may for example be a specific VH gene family).

The anti-idiotype peptides/antibodies can be applied in immunodetection assays such as ELISA, FLISA, or RIA for a direct quantification of the individual member proteins (e.g. a specific antibody or specific TcR). Alternatively, the anti-idiotype peptides/antibodies can be applied in affinity chromatography, either alone or as a first or additional dimension following other chromatographic separations as previously described. Immunoprecipitation is an additional procedure where the detector molecules can be used to separate and characterize individual members of a polyclonal protein. Further, anti-idiotype peptide or anti-idiotype antibody can be used for isolation and/or determination of individual protein producing cells in a polyclonal cell line. The techniques described by Borth, N. et al. 2000-2001. Biotechnol Bioeng. 71, 266-273 and Brezinsky, S. C. et al. 2003. J. Immunol. Methods 277, 141-155, are both applicable for isolating individual protein producing cells from a cell culture.

Potentially, it is possible to generate specific detector molecules for each and every individual member in a polyclonal protein to obtain a complete characterization. However, in order to monitor the expression stability or batch-to-batch consistency, it is in accordance with the present invention enough to identify a number of individual members, so-called sentinel proteins, within a recombinant polyclonal protein for quantitatively and/or qualitatively characterization to ensure that this collection of individual protein members is consistently expressed and purified in different batches of the recombinantly produced polyclonal protein. This approach can in particular be used to simplify the characterization of a complex pool of protein molecules. The concept of sentinel proteins as representatives of a recombinant polyclonal protein does not only apply to the specific detector molecule, virtually any of the previously described characterization techniques or combinations of these can apply the concept of sentinel proteins or peptides. Further, the sentinel proteins can vary from technique to technique. Some specific members of the polyclonal protein may separate particularly well based on the difference in their physico-chemical properties, whereas anti-idiotype peptides with high affinity are particular useful for the separation of proteins with identical physico-chemical properties.

In embodiments of the present invention, one or more specific detector molecules are used to monitor the relative proportion of one or more sentinel proteins in samples comprising different homologous proteins having different variable regions. Consistency in the proportion of one or more sentinel proteins in a series of related samples will reflect the compositional stability in the expression of a polyclonal protein between batches as well as over time in a single production run. Further, it can assess the compositional stability during long term storage of a recombinant polyclonal protein or a mixture of monoclonal proteins.

In preferred embodiments of the present invention, sentinel proteins of a recombinant polyclonal protein are characterized by one or more of the following techniques, i) anti-idiotype peptide/antibody affinity chromatography, ii) immunodetection with anti-idiotype peptides/antibodies, iii) multidimensional chromatographic isolation of intact members with respect to their characteristic physico-chemical properties, and iv) proteolytic peptide mapping using chromatography and MS.

Complexity of a Mixture of Different Homologous Proteins to be Characterized

A sample to be characterized by the platform of the present invention comprises a defined subset of different homologous proteins having different variable regions proteins, for example a polyclonal protein or antibodies with different CDR regions. (e.g. a polyclonal antibody or a mixture of monoclonal antibodies) or T cell receptors with different CDR regions (e.g. a polyclonal TcR or a mixture of monoclonal TcR5). It is of preference that the different homologous proteins having different variable regions are recombinant proteins. In addition, it is preferred that the individual members of a polyclonal protein or mixture of monoclonal proteins have been defined by a common feature such as the shared binding activity towards a desired target, e.g. in the case of antibodies or TcRs against the desired target antigen. Typically, a polyclonal protein composition to be analyzed by the characterization platform of the present invention comprise at least 3, 4, 5, 10, 20, 50, 100, 1000, $10^4$, $10^5$ or $10^6$ distinct variant members. Usually, no single variant member constitutes more than 75% of the total number of individual members in the polyclonal protein composition. Preferably, no individual member exceeds more that 50%, even more preferred 25% and most preferred 10% of the total number of individual members in the final polyclonal composition.

In the case of antibodies the complexity of the antigen(s) targeted will influence the number of distinct variant members in the polyclonal protein composition to be characterized utilizing the platform of the present invention. With small or not very complex targets, for example a small target protein, a polyclonal protein composition that comprises between 3 to 100 distinct variant members will be established for characterization, and it is preferred that the number of variants does not exceed 90, or even 80 or 70. In many instances, the number of distinct variants will not exceed 60 or 50, and it is preferred that the number of variants are in the range between 5 and 40, such as between 5 and 30. Whereas for more complex targets, for example viruses with complex or interchangeable surface proteins, or encompassing several virus subtypes, a polyclonal protein composition that comprises between 20 to 500 distinct variant members will be established for characterization. For very complex targets, where the antigen comprises many different molecules, a polyclonal protein composition comprising between 50 to 10,000 distinct variant members may need to be characterized according to the present invention.

In one embodiment of the present invention the sample comprising the different homologous proteins having different variable regions is a polyclonal antibody. The polyclonal antibody can be composed of one or more different antibody isotypes, such as the human isotypes IgG1, IgG2, IgG3, IgG4, IgA1, and IgA2, or the murine isotypes IgG1, IgG2a, IgG2b, IgG3, and IgA.

In one embodiment of the present invention the sample comprising the different homologous proteins having different variable regions is a polyclonal TcR.

EXAMPLES

In the following examples various anti-RhD recombinant polyclonal antibody (anti-RhD rpAb) compositions comprised of different individual anti-RhD antibody members or the cell lines producing the anti-RhD rpAb have been used to illustrate the structural characterization platform of the present invention. The individual anti-RhD-specific antibodies and the cell lines producing them correspond to those described in the present assignee's Danish patent application PA 2004 01133 filed Jul. 20, 2004. Briefly, a combinatorial phage display library of heavy chain variable regions and kappa/lambda light chains was generated from rhesus D-negative donors immunized with RhD-positive erythrocytes. The library was panned for anti-RhD-specific antibody producing clones. Variable heavy and light chains gene pairs from antigen-specific phages were transferred to a mammalian expression vector: The mammalian vectors were transfected individually into CHO Flp-In cell line (Invitrogen, CA), in a site-specific manner using the Flp-FRT recombination system. Nucleic acid (nuc.) as well as protein (a.a.) sequences for the complete light chains (LC) as well as the variable region of the heavy chains (VH) are identified by the sequence identity numbers (seq id) shown in table 2. These numbers correspond to the SEQ ID NOs in the present assignee's International patent application PCT/DK2005/000501 titled "ANTI-RHESUS D RECOMBINANT POLYCLONAL ANTIBODY AND METHODS OF MANUFACTURE" and filed on 18 Jul. 2005. The seq id's of Table 2 must be distinguished from the SEQ ID NOs of the present application, since these are not identical. The constant region of the heavy chains corresponds to human IgG1.

TABLE 2

List of individual anti-RhD antibodies/cell clones used in the following examples.

| Synonym | Clone/Ab Name | VH nuc. seq id | LC nuc. seq id | VH a.a. Seq id | LC a.a. seq id |
|---|---|---|---|---|---|
| RhD157 | RhD157.119D11 | 35 | 91 | 147 | 203 |
| RhD158 | RhD158.119B06 | 36 | 92 | 148 | 204 |
| RhD159 | RhD159.119B09 | 37 | 93 | 149 | 205 |
| RhD160 | RhD160.119C07 | 38 | 94 | 150 | 206 |
| RhD161 | RhD161.119E09 | 39 | 95 | 151 | 207 |
| RhD162 | RhD162.119G12 | 40 | 96 | 152 | 208 |
| RhD163 | RhD163.119A02 | 41 | 97 | 153 | 209 |
| RhD189 | RhD189.181E07 | 42 | 98 | 154 | 210 |
| RhD190 | RhD190.119F05 | 43 | 99 | 155 | 211 |
| RhD191 | RhD191.119E08 | 44 | 100 | 156 | 212 |
| RhD192 | RhD192.119G06 | 45 | 101 | 157 | 213 |
| RhD196 | RhD196.126H11 | 49 | 105 | 161 | 217 |
| RhD197 | RhD197.127A08 | 50 | 106 | 162 | 218 |
| RhD198 | RHd198.127F10 | 51 | 107 | 163 | 219 |
| RhD199 | RhD199.164E03 | 52 | 108 | 164 | 220 |
| RhD201 | RhD201.164H12 | 54 | 110 | 166 | 222 |
| RhD202 | RhD202.158E07 | 55 | 111 | 167 | 223 |
| RhD203 | RhD203.179F07 | 56 | 112 | 168 | 224 |
| RhD204 | RhD204.128A03 | 57 | 113 | 169 | 225 |
| RhD207 | RhD207.127A11 | 60 | 116 | 172 | 228 |
| RhD240 | RhD240.125A09 | 63 | 119 | 175 | 231 |
| RhD241 | RhD241.119B05 | 64 | 120 | 176 | 232 |
| RhD244 | RhD244.158B10 | 67 | 123 | 179 | 235 |
| RhD245 | RhD245.164E06 | 68 | 124 | 180 | 236 |
| RhD293 | RhD293.109A09 | 71 | 127 | 183 | 239 |
| RhD301 | RhD301.160A04 | 79 | 135 | 191 | 247 |
| RhD305 | RhD305.181E06 | 83 | 139 | 195 | 251 |
| RhD306 | RhD306.223E11 | 84 | 140 | 196 | 252 |
| RhD307 | RhD307.230E11 | 85 | 141 | 197 | 253 |
| RhD317 | RhD317.144A02 | 86 | 142 | 198 | 254 |
| RhD319 | RhD319.187A11 | 87 | 143 | 199 | 255 |
| RhD321 | RhD321.187G08 | 88 | 144 | 200 | 256 |
| RhD324 | RhD324.231F07 | 90 | 146 | 202 | 258 |

Example 1

The present example illustrates the generation of a polyclonal manufacturing cell line, and characterization of the batch-to-batch variation on the protein level using a chromatographic technique in one dimension and at the genetic level using RFLP analysis.

Establishment of a Manufacturing Cell Line for Anti-Rhesus D Recombinant Polyclonal Antibody Production Ten cell lines each expressing a distinct recombinant anti-Rhesus D antibody from a specific site on their genome (RhD157.119D11, RhD158.119B06, RhD159.119B09, RhD161.119E09, RhD163.119A02, RhD190.119F05, RhD191.119E08, RhD192.119G06, RhD197.127A08 and RhD204.128A03) were selected and mixed to constitute the recombinant polyclonal manufacturing cell line. RhD197 and RhD204 were Lambda clones whereas the remaining were Kappa clones.

After the cell cultures expressing the individual anti-Rhesus antibodies were fully adapted to serum free suspension culture in shaker flasks they were mixed in equal cell number, thereby generating a polyclonal CHO-Flp-In (019) cell line. The mixed cell culture was centrifuged and frozen down in aliquots of $10 \times 10^6$ cells/tube.

Two tubes (3948 FCW065 and 3949 FCW065) were thawed and cultured individually for 11 weeks in 1000 ml shaker flasks containing 100 ml Excell302 serum-free medium with neomycin.

The supernatant was harvested and filtered prior to purification of the anti-RhD rpAb.

Clonal Diversity

The clonal diversity was assayed both at the protein level as well as at the mRNA level. The supernatant sample used to analyze the antibody composition was taken after 9 weeks of cultivation, whereas the cell sample used to analyze the mRNA composition was taken at the harvest after 11 weeks of cultivation.

Antibody Composition:

The anti-RhD rpAb expressed from the polyclonal CHO-Flp-In (019) cell line is an IgG1 isotype antibody. Anti-RhD rpAb was purified from both aliquots (3948 and 3949) using a column immobilized with Protein A. The individual antibodies interacted with immobilized Protein A at pH 7.4, whereas contaminating proteins were washed from the column. The bound antibodies were subsequently eluted from the column at low pH value (pH 2.7). The fractions containing antibodies, determined by absorbance measurements at 280 nm, were pooled and dialyzed against 5 mM sodium acetate pH 5.

The anti-RhD rpAb compositions obtained from aliquot 3948 and 3949 (FCW065) after 9 weeks of cultivation were analyzed using cation-exchange chromatography. The Protein A purified anti-RhD rpAb was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm. The chromatogram (FIG. 1) was subsequently integrated and the areas of the individual peaks A-J were used to quantitate antibody components (Table 3). The total area of the peaks was set to 100%. The chromatograms from the two aliquots showed an identical peak distribution, as well as similar concentrations of the components in each peak. From these results it can be concluded that aliquots of the same polyclonal cell line grown under identical conditions will produce anti-RhD rpAb with a similar distribution of individual antibody members.

The individual members of the anti-RhD rpAb were assigned to one or more particular peaks (summarized in Table 3). This assignment is based on chromatograms obtained for individual antibodies, analyzed under identical conditions. An individual chromatogram was not obtained for the RhD158 Ab, thus this clone was not assigned to any of the peaks. However, it is considered likely that peak D constitute RhD158, this antibody may also be represented in some of the other peaks due to heterogeneity. In particular the antibody product from clone RhD197 shows a high degree of heterogeneity in the IEX profile. The RhD190 Ab should have been visible at a retention time of 15.3 min. However, it was not detectable, indicating that this clone was lost or alternatively produced in amounts below the limit of detection in the recombinant polyclonal manufacturing cell line. The loss of clone RhD190 corresponds to a 10% reduction of diversity which is considered acceptable with respect to diversity of the final anti-RhD rpAb composition.

TABLE 3

| Peak | Quantity 3948 (% area) | Quantity 3949 (% area) | Ab name | Comment |
|---|---|---|---|---|
| A | 5.1 | 5.1 | RhD157 | This Ab is also present in peak B |
| B | 12.0 | 10.2 | RhD157 RhD159 RhD192 | This peak represent at least three different Ab's |
| C | 5.2 | 5.3 | RhD191 | |
| D | 1.2 | 0.8 | (RhD158) | Not actually assigned to this peak, but it is likely to be. RhD158 may also be represented in other peaks. |
| E | 10.9 | 14.4 | RhD204 | |
| F | 24.3 | 23.0 | RhD197 | This clone split into several peaks, due to heterogeneity. |
| G | 13.6 | 12.5 | RhD197 | |
| H | 3.3 | 4.0 | RhD197 | |
| I | 14.0 | 13.7 | RhD161 | |
| J | 10.5 | 10.5 | RhD163 RhD190 | This Ab was not detected | mRNA Composition:

The clonal diversity within the polyclonal CHO-Flp-In (019) cell line after 11 weeks of cultivation was estimated by RT-PCR-RFLP analysis. Briefly, cell suspensions corresponding to 200 cells were subjected to a freeze-thaw procedure and these lysates were used as template in a RT-PCR using One-STEP RT-PCR kit (Qiagen) with primers amplifying the light chain. The primer sequences were:

```
Forward primer:   5'-TCTCTTCCGCATCGCTGTCT       (SEQ ID NO 1)

Reverse primer:   5'-AGGAAAGGACAGTGGGAGTGGCAC   (SEQ ID NO 2)
```

Figure 2:
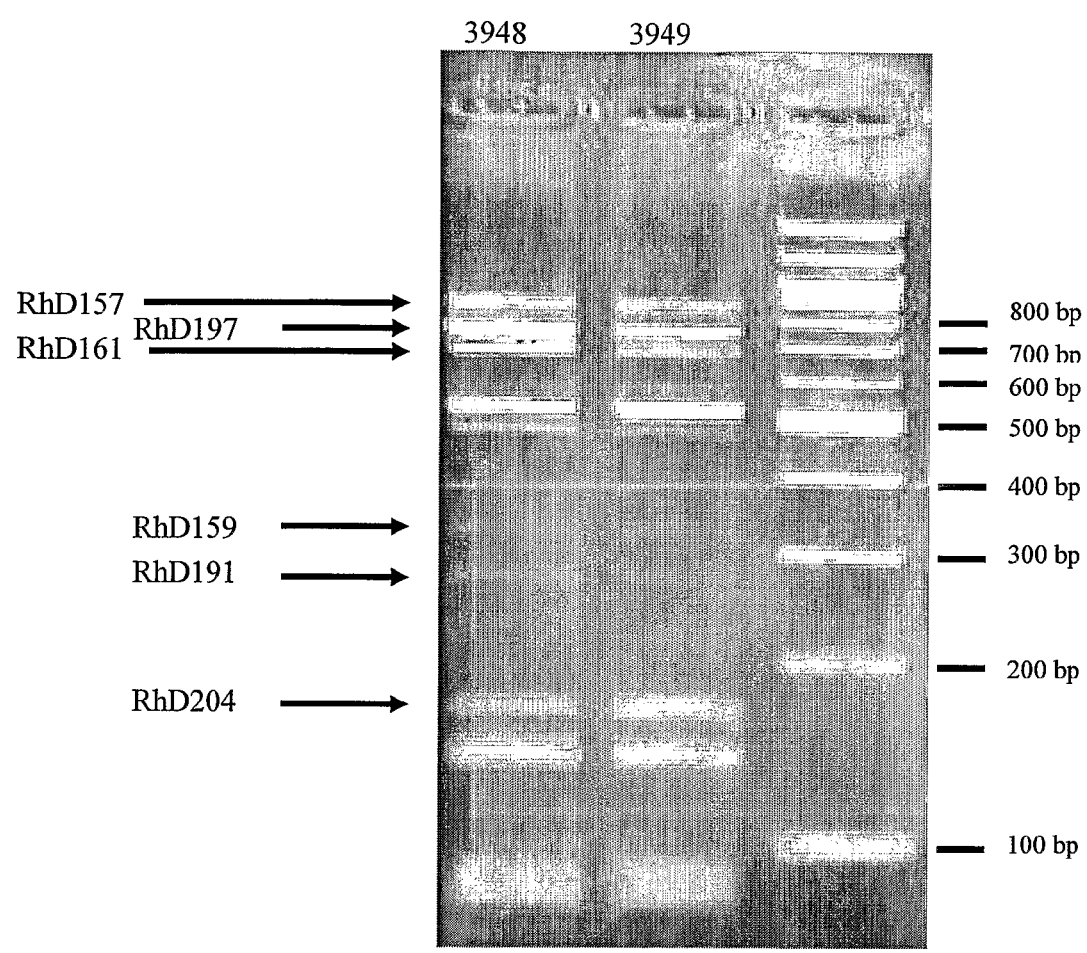
FIG. 2: Gel picture showing HinfI RFLP analysis on RT-PCR product derived from the polyclonal cell line aliquots 3948+ and 3949+(FCW065) producing anti-RhD rpAb after 11 weeks of cultivation. Bands which can be assigned to specific clones are identified.

The RT-PCR products were digested with HinfI and analyzed by agarose gel electrophoresis, visualizing the restriction product with ethidium bromide staining (FIG. 2).

The expected size of the restriction fragments obtained by HinfI digestion of the RT-PCR amplified light chains are shown for each individual clone in Table 4. Six unique fragment sizes on the gel, which could be assigned to individual members of the polyclonal anti-Rhesus D antibody encoding genes, are indicated in bold. Not all unique fragments could be identified on the gel, these are indicated in italic. This, however, does not necessarily preclude that these clones are actually represented in the culture, since the fragments may either not have been separated sufficiently from other fragments to be identifiable, or alternatively that the concentration has been too weak compared to the stronger appearing bands. This may be more pronounced for shorter fragments, since they bind a smaller number of ethidium bromide molecules and therefore are less visible.

TABLE 4

| | RhD # | | | | | | | | | |
|---|---|---|---|---|---|---|---|---|---|---|
| | 157 | 158 | 159 | 161 | 163 | 190 | 191 | 192 | 197 | 204 |
| HinfI fragment size | 825 | 671 | 505 | 696 | 505 | 502 | *475* | 671 | 743 | *521* |
| | 138 | 138 | 320 | 138 | *166* | *191* | 268 | *149* | 138 | 167 |
| | 76 | 126 | 138 | 126 | *154* | 138 | 138 | 138 | 85 | 138 |
| | | 76 | 77 | 76 | 138 | 126 | 85 | 76 | 76 | 88 |
| | | 22 | | | 76 | 76 | 76 | | | |

The two aliquots (3948 and 3949) of the same polyclonal cell line, showed a similar expression pattern in the gel, although the intensity of the bands were not completely identical. This indicates that aliquots of the same polyclonal cell line grown under identical conditions will produce anti-RhD rpAb with a similar clonal diversity.

Summary

Ten cell lines each expressing a monoclonal anti-RhD antibody were mixed in order to generate an anti-RhD rpAb manufacturing cell line, which after 9 weeks of cultivation still maintained 90% of the initial diversity. After 11 weeks of cultivation mRNA from six different clones could be unambiguously identified and several other clones are likely to be represented in the band at approximately 500 bp.

The fact that two aliquots of the polyclonal CHO-Flp-In (019) cell lines showed similar results with respect to clonal diversity, illustrates that reproducible results can be obtained between different batches.

Example 2

The present example illustrates the characterization of a polyclonal cell culture with eight members over time. The clonal diversity of the culture was assessed at the genetic level using RFLP analysis and at the protein level using a chromatographic technique in one dimension.

RFLP Analysis to Estimate Clone Diversity in Polyclonal Cell Cultures

The distribution of the individual clones in a polyclonal cell culture expressing eight different anti-Rhesus D antibodies was estimated by terminal RFLP (T-RFLP) analysis of RT-PCR products derived from the polyclonal cell line. In the T-RFLP procedure the forward and/or reverse primer(s) are fluorescently labeled and therefore a proportion of the restriction fragments generated from the amplicons will contain the label. The labeled fragments can subsequently be separated by capillary electrophoresis and detected by fluorescence.

The analysis can be performed both on the light chain and the variable region of the heavy chain encoding sequences, depending on the primers applied.

Briefly, a cell suspension corresponding to 200 cells was washed one time in PBS and subjected to a freeze-thaw procedure generating lysates used as template in a RT-PCR amplification using a One-Step RT-PCR kit (Qiagen) and suitable primers.

The RT-PCR was carried out on a standard thermal cycler with the following conditions:

| | |
|---|---|
| Reverse transcription | 55° C. for 30 min |
| Denature | 95° C. for 15 min |
| Start cycle loop (35 cycles) | |
| Denature | 95° C. for 30 sec |
| Anneal | 60° C. for 30 sec |
| Elongate | 72° C. for 5 min |
| End cycle loop | |
| Elongate | 72° C. for 15 min |
| Finish | 8° C. forever |

For analysis of the light chain the following primers were used for the RT-PCR amplification. The reverse primer was 6-carboxyflorescein (FAM) labeled and the primer sequences were as follows:

```
                                              (SEQ ID NO 1)
VL Forward primer:  5'-TCTCTTCCGCATCGCTGTCT (SEQ ID NO 2)
CL Reverse primer:  5'-FAM-AGGAAAGGACAGTGGGAGTGGCAC
```

Twenty µl of the RT-PCR product was digested with 1 U of NheI, 1 U of PstI and 1 U of HinfI (all from New England Biolabs) in NEB1 for 2 hours.

The labeled fragments were detected by fluorescence capillary electrophoresis on an ABI3700 (Applied Biosystems) at Statens Serum Institute, Copenhagen, DK.

The expected fragments for each of the anti-RhD antibody producing cell clones are shown in Table 5 and the FAM labeled fragments are indicated in bold.

TABLE 5

| | RhD # | | | | | | | |
|---|---|---|---|---|---|---|---|---|
| | 191 | 196 | 201 | 203 | 244 | 306 | 319 | 324 |
| NheI/PstI/HinfI fragment size | 475 | 696 | 516 | 422 | 690 | 682 | 761 | 513 |
| | 210 | 138 | 166 | 318 | 138 | 138 | 138 | 166 |
| | 138 | 76 | 138 | 138 | 76 | 76 | 76 | 138 |
| | 76 | 67 | 76 | 76 | 67 | 67 | 67 | 76 |
| | 67 | 59 | 76 | 67 | 41 | 59 | | 76 |
| | 58 | | 67 | 18 | 18 | 17 | | 67 |
| | 18 | | | | | | | |

Figure 3:
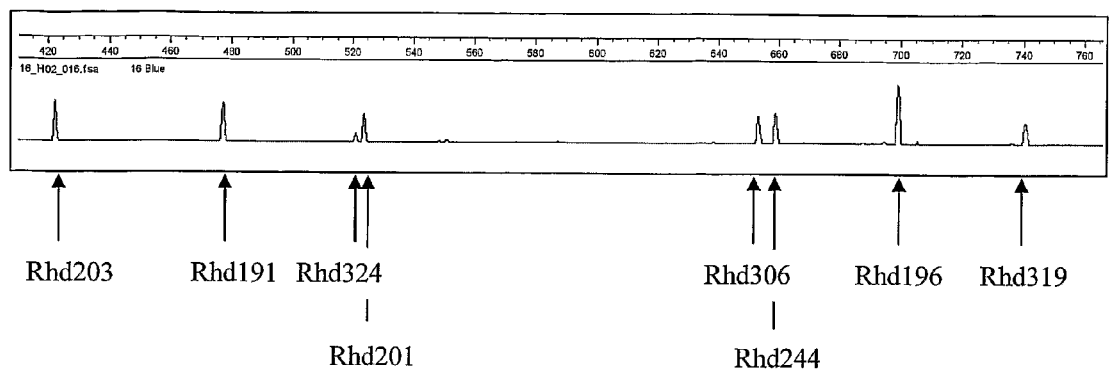
FIG. 3: T-RFLP patterns of anti-Rhesus D antibody light chains from a polyclonal cell culture expressing anti-RhD rpAb with eight different anti-Rhesus D antibodies. The eight different anti-Rhesus D clones have been assigned to the peaks indicated by arrows.

The T-RFLP pattern is shown in FIG. 3 and all eight anti-Rhesus D antibody producing clones have been assigned to specific peaks. Under the assumption that there was no template/primer competition during the RT-PCR, the relative peak area will correspond to the relative amount of mRNA transcribed from each antibody light chain gene represented in the polyclonal cell line.

For analysis of the heavy chain variable region within the same polyclonal cell line the RT-PCR amplification was carried out with VH-specific primers. The primer sequences were as follows:

```
                                              (SEQ ID NO 3)
VH Forward primer:  5'-FAM CGTAGCTCTTTTAAGAGGTG SEQ ID NO 4)
VH Reverse primer:  5'-HEX-ACCGATGGGCCCTTGGTGGA
```

Twenty µl of the RT-PCR product was digested with 1 U of RsaI and 1 U of NdeI (all from New England Biolabs) in NEB2 for 2 hours.

The labeled fragments were detected by fluorescence capillary electrophoresis on an ABI3700. The analysis was performed by Statens Serum Institute, Copenhagen, DK.

The expected T-RFLP patterns are shown in Table 6, where the FAM labeled fragments are shown in bold and the HEX (6-Carboxy-2',4,4',5,7,7'-hexachlorofluorescein succinimidyl ester) labeled fragments are underscored.

TABLE 6

| | RhD # | | | | | | | |
|---|---|---|---|---|---|---|---|---|
| | 191 | 196 | 201 | 203 | 244 | 306 | 319 | 324 |
| RsaI/NdeI Fragment size | 203 | 429 | 186 | 350 | 435 | 328 | 232 | 266 |
| | <u>166</u> | | 142 | <u>88</u> | | <u>79</u> | 118 | <u>157</u> |
| | 63 | | <u>79</u> | | | 22 | <u>79</u> | |
| | | | 22 | | | 9 | 9 | |
| | | | 9 | | | | | |

The polyclonal cell line was cultivated over 5 weeks and once a week samples were taken for T-RFLP analyses. The analysis was performed on the variable heavy chain, but could have been performed on the light chain as well if desired.

Figure 5:
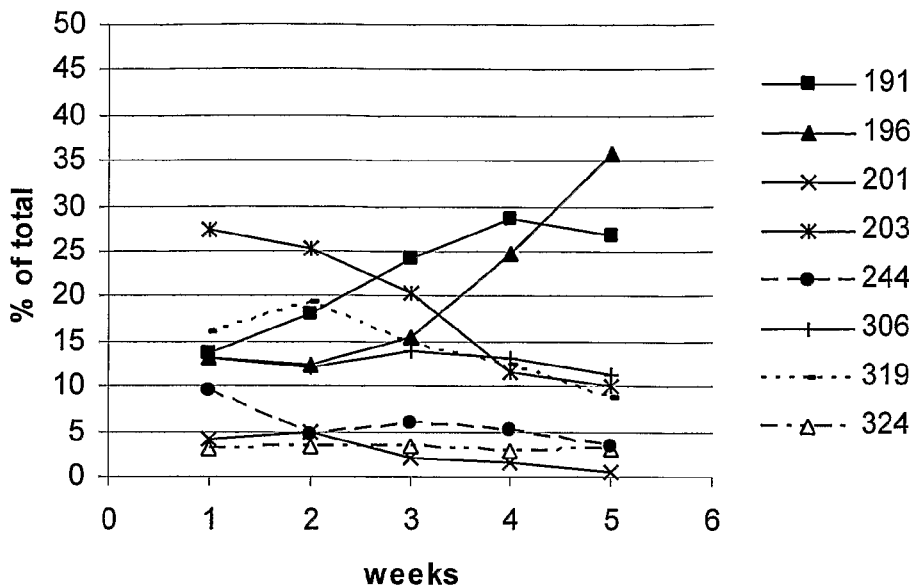
FIG. 5: cDNA distribution estimated by T-RFLP of eight different anti-Rhesus D heavy chain encoding sequences from a polyclonal cell culture which was cultivated for five weeks.

After capillary electrophoresis of the restriction fragments, the relative peak areas were integrated and used to estimate the clonal diversity of the polyclonal cell culture. The relative quantities over time are shown in FIG. 5.

Based on these results, it seems that RhD196 increase whereas RhD203 seems to decrease over time. The quantities of the other clones are quite stable during the cultivation period and all eight cDNA could be detected after five weeks of cultivation.

By performing T-RFLP on both light chain and heavy chain as well as on both mRNA and DNA it should be possible to obtain a precise fingerprint of the clonal diversity within the polyclonal cell culture, for example in cells at the limit of in vitro cell age or at any given time point during cultivation.

The technique can therefore be used to monitor the stability of the clonal diversity in a cell culture over time during antibody production. The technique can also be applied to monitor the batch-to-batch consistency for example of different ampoules frozen down from the same polyclonal working cell bank (pWCB) or in cells harvested after two or more manufacturing runs.

Figure 6:
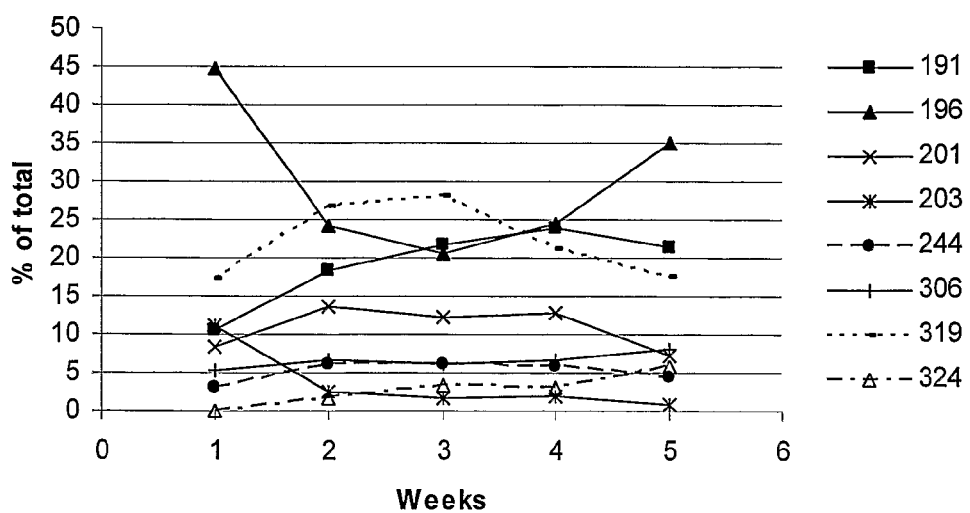
FIG. 6: Shows the relative content (%) of an anti-RhD rpAb with eight different antibodies analyzed using cation-exchange chromatography. Integrated chromatographic peaks were assigned to individual antibodies from the retention times and peak patterns obtained from single antibodies analyzed individually using cation-exchange chromatography under identical conditions.

Cation-Exchange Chromatographic Analysis to Estimate Clonal Diversity in a Polyclonal Cell Culture The anti-RhD rpAb produced from the same polyclonal cell culture as used in the T-RFLP analysis described above was analyzed using cation-exchange chromatography. The protein A purified recombinantly produced polyclonal antibody was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm and the chromatogram was subsequently integrated and the area of individual peaks was then used to quantitate antibody components. The relative quantities over time are shown in FIG. 6.

Summary

The results obtained at the genetic level by the RFLP analysis and at the protein level by cation-exchange chromatography are comparable. FIGS. 5 and 6 clearly illustrate that most of the individual clones in the polyclonal cell line as well as the individual antibodies of the polyclonal antibody expressed from the cell line follow the same trends during the 5 weeks of cultivation. Thus, analyses at the genetic as well as at protein level are good equivalents for assessing the compositional diversity of a cell line at the genetic level and of the recombinant polyclonal protein produced from the cell line.

Example 3

The present example illustrates the characterization of a polyclonal cell culture with twenty-five members over time. The clonal diversity of the culture was assessed at the genetic level using T-RFLP analysis and at the protein level using a chromatographic technique in one dimension.

T-RFLP Analysis of the Variable Part of the Heavy Chain Genes Derived from a Polyclonal Cell Culture Expressing Twenty-Five Different Anti-Rhesus D Antibodies Over a 5 Weeks Cultivation Period.

The polyclonal cell culture examined in the present example was composed of a mixture of cell cultures expressing twenty-five different anti-Rhesus D antibodies (generated as described in Example 1). The polyclonal cell culture was cultivated over 5 weeks and once a week samples were taken for T-RFLP analyses.

The RT-PCR was carried out with the VH-specific primers described in Example 2 and restriction fragmentation was carried out likewise.

Figure 4:
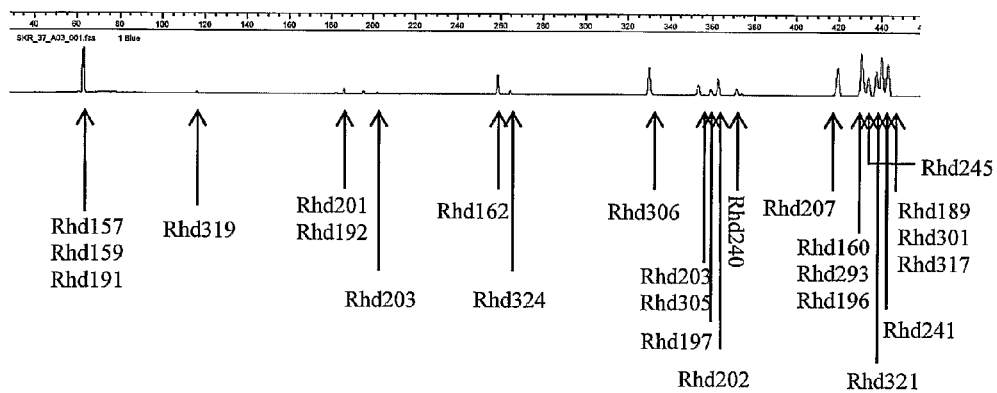
FIG. 4: T-RFLP patterns of anti-Rhesus D antibody heavy chain variable regions from a polyclonal cell culture expressing anti-RhD rpAb with twenty-five different anti-Rhesus D antibodies at a given time point. The twenty-five different anti-Rhesus D clones have been assigned to the peaks indicated by arrows.

T-RFLP of the twenty-five different anti-Rhesus D encoding sequences will, if all genotypes are present, result in seventeen different FAM labeled fragments. Some fragments will represent up to three different genotypes whereas others will represent a single genotype. The expected sizes of FAM labeled fragments are shown in Table 7 together with the relative quantities of the different FAM labeled fragments over time. Further, one example of a T-RFLP profile is shown in FIG. 4

TABLE 7

| RhD # | RsaI/NdeI FAM fragment size (bp) | Group | Week 1 Area % | Week 2 Area % | Week 3 Area % | Week 4 Area % | Week 5 Area % |
|---|---|---|---|---|---|---|---|
| Rhd157 | 63 | 1 | 9.5 | 5.0 | 5.3 | 4.8 | 4.6 |
| Rhd159 | 63 | 1 | | | | | |
| Rhd191 | 63 | 1 | | | | | |
| Rhd319 | 118 | 2 | 0.8 | 0.2 | 0.2 | 0.2 | 0.0 |
| Rhd201 | 186 | 3 | 1.5 | 0.8 | 0.9 | 1.1 | 0.7 |
| Rhd192 | 187 | 3 | | | | | |
| Rhd199 | 203 | 4 | 0.9 | 0.3 | 0.3 | 0.4 | 0.4 |
| Rhd162 | 260 | 5 | 7.4 | 3.6 | 1.7 | 1.0 | 0.0 |
| Rhd324 | 266 | 6 | 1.0 | 0.8 | 0.6 | 0.5 | 0.0 |
| Rhd306 | 328 | 7 | 10.3 | 8.0 | 7.2 | 7.9 | 7.8 |
| Rhd203 | 350 | 8 | 6.0 | 3.4 | 3.8 | 5.9 | 8.9 |
| Rhd305 | 350 | 8 | | | | | |
| Rhd197 | 356 | 9 | 5.1 | 1.8 | 1.7 | 1.8 | 1.3 |
| Rhd202 | 359 | 10 | 3.8 | 4.3 | 5.6 | 5.2 | 3.7 |
| Rhd240 | 369 | 11 | 3.3 | 1.8 | 1.3 | 0.8 | 0.0 |
| Rhd207 | 414 | 12 | 11.7 | 10.5 | 10.1 | 9.9 | 11.1 |
| Rhd160 | 426 | 13 | 11.3 | 17.1 | 17.5 | 18.1 | 17.2 |
| Rhd293 | 426 | 13 | | | | | |
| Rhd196 | 426 | 13 | | | | | |
| Rhd245 | 429 | 14 | 6.5 | 7.1 | 8.3 | 11.0 | 16.8 |
| Rhd321 | 432 | 15 | 6.8 | 9.4 | 8.3 | 7.5 | 4.9 |
| Rhd241 | 435 | 16 | 4.8 | 13.7 | 12.5 | 7.2 | 4.0 |
| Rhd189 | 438 | 17 | 9.4 | 12.3 | 14.8 | 16.8 | 18.7 |
| Rhd301 | 438 | 17 | | | | | |
| Rhd317 | 438 | 17 | | | | | |

It was possible to separate the restriction fragments to an extent that allowed information to be obtained for twelve individual clones of the twenty-five clones constituting the cell line. The remaining fractions could potentially be subjected to sequencing in order to obtain more information on the remaining clones.

Figure 7:
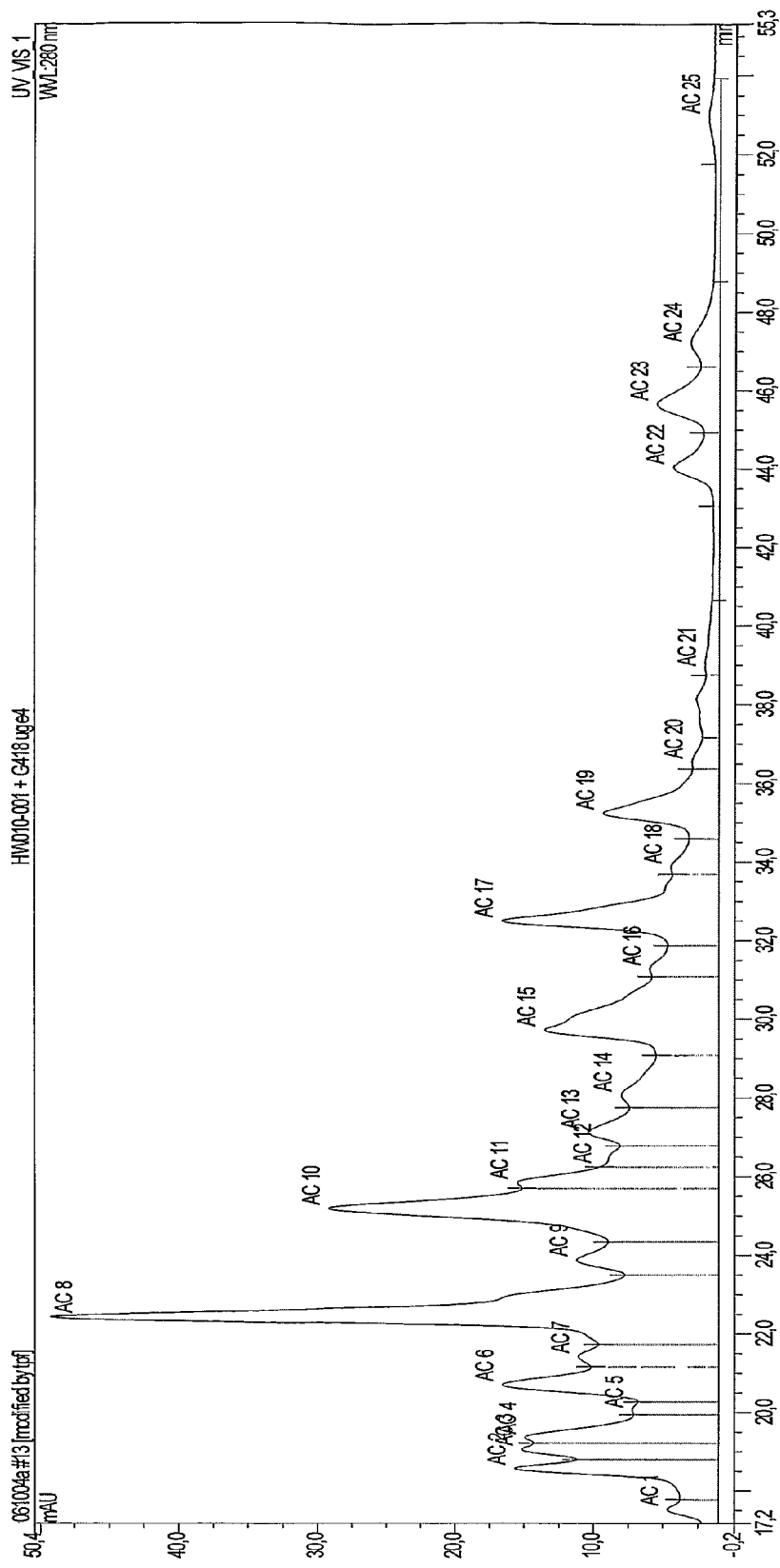
FIG. 7: Cation-exchange chromatogram of an anti-RhD rpAb with twenty-five individual members from a sample obtained after 4 weeks cultivation. Peaks AC1 to 25 comprise antibodies differing in net charge and individual antibodies appearing charge heterogeneous.

Cation-Exchange Chromatographic Analysis to Estimate Clonal Diversity in a Polyclonal Cell Culture Expressing Twenty-Five Different Anti-Rhesus D Antibodies The anti-RhD rpAb produced from the same polyclonal cell culture as used in the T-RFLP analysis described above, was analyzed using cation-exchange chromatography. The protein A purified recombinantly produced polyclonal antibody was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm and the chromatogram was subsequently integrated and the area of individual peaks was used to quantitate the different antibody components. FIG. 7 shows the chromatogram produced from the sample obtained at week 4, the antibody containing peaks being numbered from 1 to 25. It is pure concurrence that the chromatogram contains an identical number of peaks as the number of individual antibodies in the polyclonal antibody analyzed. Table 8 show the relative content in percent of the total antibody components (AC1 to 25), as well as the representation of the individual antibodies in each antibody component (peak). The assignment of individual antibodies to the integrated chromatographic peaks was based on the retention times and peak patterns obtained from monoclonal antibodies analyzed using cation-exchange chromatography under identical conditions.

TABLE 8

| Peak | RhD# Ab represented | Week 1 Rel. Area % | Week 2 Rel. Area % | Week 3 Rel. Area % | Week 4 Rel. Area % | Week 5 Rel. Area % |
|---|---|---|---|---|---|---|
| AC 1 | 293, 319 | 2.06 | 2.3 | 1.7 | 1.06 | 0.81 |
| AC 2 | 157, 293 | 3.63 | 3.83 | 3.97 | 3.89 | 3.06 |
| AC 3 | 157, 192 | 2.66 | 2.8 | 2.89 | 2.83 | 2.34 |
| AC 4 | 159, 189, 199 | 6.11 | 5.52 | 5.1 | 4.1 | 2.99 |
| AC 5 | 319 | 2.18 | 1.94 | 1.33 | 1.08 | 1.26 |
| AC 6 | 241, 191 | 6.01 | 6.4 | 6.32 | 5.42 | 4.1 |
| AC 7 | 189, 192, 199, 201 | 3.89 | 4.21 | 3.38 | 2.95 | 2.63 |
| AC 8 | 160 | 12.1 | 15.77 | 18.71 | 17.59 | 15.56 |
| AC 9 | 203, 191 | 2.65 | 3.89 | 3.69 | 3.99 | 4.14 |
| AC 10 | 162, 202 | 6.78 | 10.22 | 13.52 | 12.29 | 9.75 |
| AC 11 | 203, 306, 301 | 2.86 | 3.63 | 4.35 | 3.66 | 3.92 |
| AC 12 | 245 | 1.43 | 1.63 | 1.5 | 2.27 | 2.02 |
| AC 13 | 301, 321 | 2.5 | 3.35 | 3.92 | 4.16 | 3.64 |
| AC 14 | 305 | 2.44 | 2.61 | 3.12 | 4.23 | 6.07 |
| AC 15 | 196, 197, 240, 305, 321 | 8.33 | 7.22 | 7.36 | 8.49 | 4.01 |
| AC 16 | 197 | 3.82 | 2.71 | 2.15 | 1.86 | 7.86 |
| AC 17 | 196, 240, 324 | 7.57 | 5.12 | 4.86 | 6.89 | 7.79 |
| AC 18 | 197, 321 | 2.27 | 1.44 | 1.51 | 1.39 | 2.83 |
| AC 19 | 196, 240 | 3.8 | 2.63 | 2.87 | 3.98 | 6.35 |
| AC 20 | 317 | 4.58 | 1.39 | 0.77 | 0.71 | 0.86 |
| AC 21 | 317 | 2.86 | 0.59 | 0.36 | 0.83 | 0.42 |
| AC 22 | 207 | 2.07 | 2.61 | 1.58 | 1.65 | 1.93 |
| AC 23 | 207 | 3.33 | 3.87 | 2.56 | 2.41 | 2.87 |
| AC 24 | 207 | 2.46 | 3.48 | 1.73 | 1.52 | 1.92 |
| AC 25 | Unknown | 1.58 | 0.83 | 2 | 0.75 | 0.87 |

Cation-exchange chromatography separates individual antibody members from a polyclonal antibody based on differences in net charge between the individual members and in addition separates forms of individual antibodies that appear charge heterogeneous. Several antibodies were therefore represented in a single peak, e.g. AC 1 containing RhD293 and RhD319 (see Table 8) and some individual antibodies were further represented in several chromatographic peaks, e.g. RhD319 which is present both in AC1 and 5 (see Table 8).

Peaks which contain more than one individual antibody could be subjected to additional protein chemical characterization techniques, such as quantitative analysis with anti-idiotype peptides, proteolytic peptide mapping, N-terminal sequencing or a second dimension chromatography.

Summary

The present example illustrates the combined use of T-RFLP analyses and cation-exchange chromatography for assessing the distribution of the primary transcripts and of antibody components, respectively, over a period of cultivation. The T-RFLP analysis allows for unique identification of 12 individual clones of the 25 clones expressed in the polyclonal cell line and in the present example it is illustrated that these 12 clones could be detected during 4 weeks cultivation with the T-RFLP analysis. Potentially, more clones could be identified by sequence analysis of fragments representing more than one clone. The distribution of antibody components was analyzed using cation-exchange chromatography and in the present example it is seen that the distribution of the 25 analyzed components is relatively stable during cultivation Although unique identification of all individual antibodies is difficult due to the inherent charge heterogenous nature of the expressed antibodies it was demonstrated in the present example that antibody component 8 representing the RhD160 antibody showed the highest antibody level during the cultivation period in accordance with the high T-RFLP values obtained for group 13 representing the RhD160, 293, and 196 clones. Furthermore, the RhD 207 component, which could be uniquely identified by T-RFLP as well as by cation-exchange chromatography, showed T-RFLP levels of 10-11% and slightly lower levels of 5.5-10% obtained at antibody level. Overall, the two techniques together demonstrate a relatively stable production at the mRNA and antibody level during cultivation; however, potential discrepancies between the two techniques could also be seen, illustrated by the apparent loss of transcription of some clones at weeks 5 of cultivation contrasting the results obtained at the antibody level. Thus, the present example justifies the complementary use of both techniques to define cultivation intervals within which stable production of complex polyclonal protein can be obtained.

Example 4

The present example illustrates a compositional analysis of a polyclonal anti-RhD antibody with ten individual members derived from a polyclonal cell culture. The diversity of the polyclonal antibody sample was assessed using two-dimensional liquid chromatography which separated the antibodies based on differences in their net charge and hydrophobicity, using cation-exchange in the first dimension and reverse phase (RP)-HPLC in the second dimension, respectively.

A polyclonal anti-RhD antibody sample with ten individual members was derived from a polyclonal cell culture.

The anti-RhD rpAb was purified from the supernatant using a protein A column (HiTrap™ Protein A column, Amersham Biosciences GE Healthcare, England).

The first dimension was executed by applying the purified polyclonal antibody onto a ProPac WCE10 column (4×250 mm) in 25 mM sodium acetate, 150 mM sodium chloride, pH 5.0 at a flow rate of 60 ml h$^{-1}$ operated at room temperature on an Ettan LC system (Amersham Biosystems, GE Healthcare, England). The antibody components were subsequently eluted using a linear gradient from 150 to 350 mM NaCl in 25 mM sodium acetate, pH 5.0 at a flow rate of 60 ml h$^{-1}$. The antibody components were detected spectrophotometrically at 280 nm and fractions corresponding to particular peaks were collected and further concentrated prior to analysis by RP-HPLC.

Figure 8:
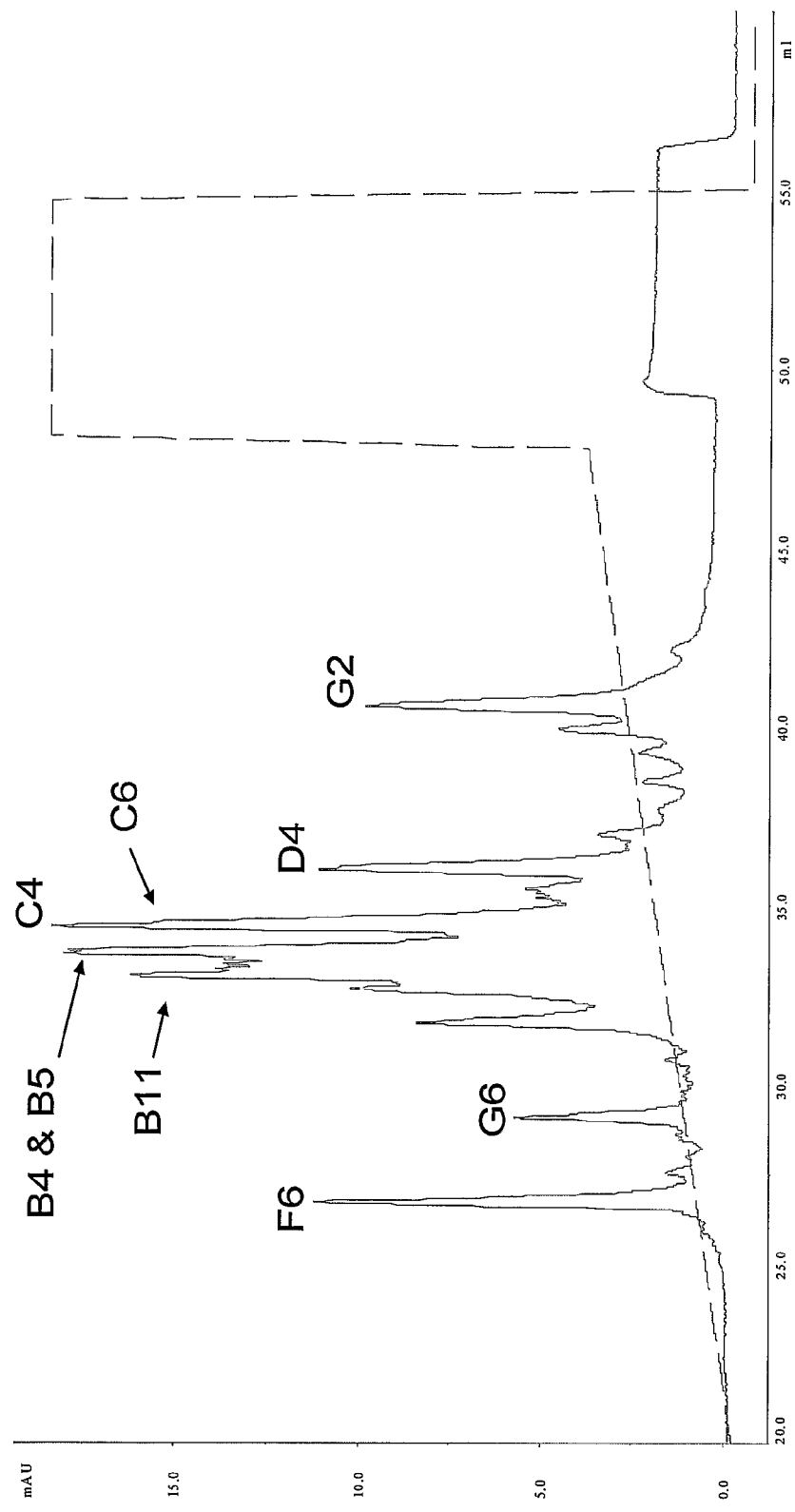
FIG. 8: Elution profile from a cation-exchange chromatography of a recombinant polyclonal anti-RhD antibody with ten individual members. The letters indicate peaks subjected to RP-HPLC, in the second dimension.
Figure 9:
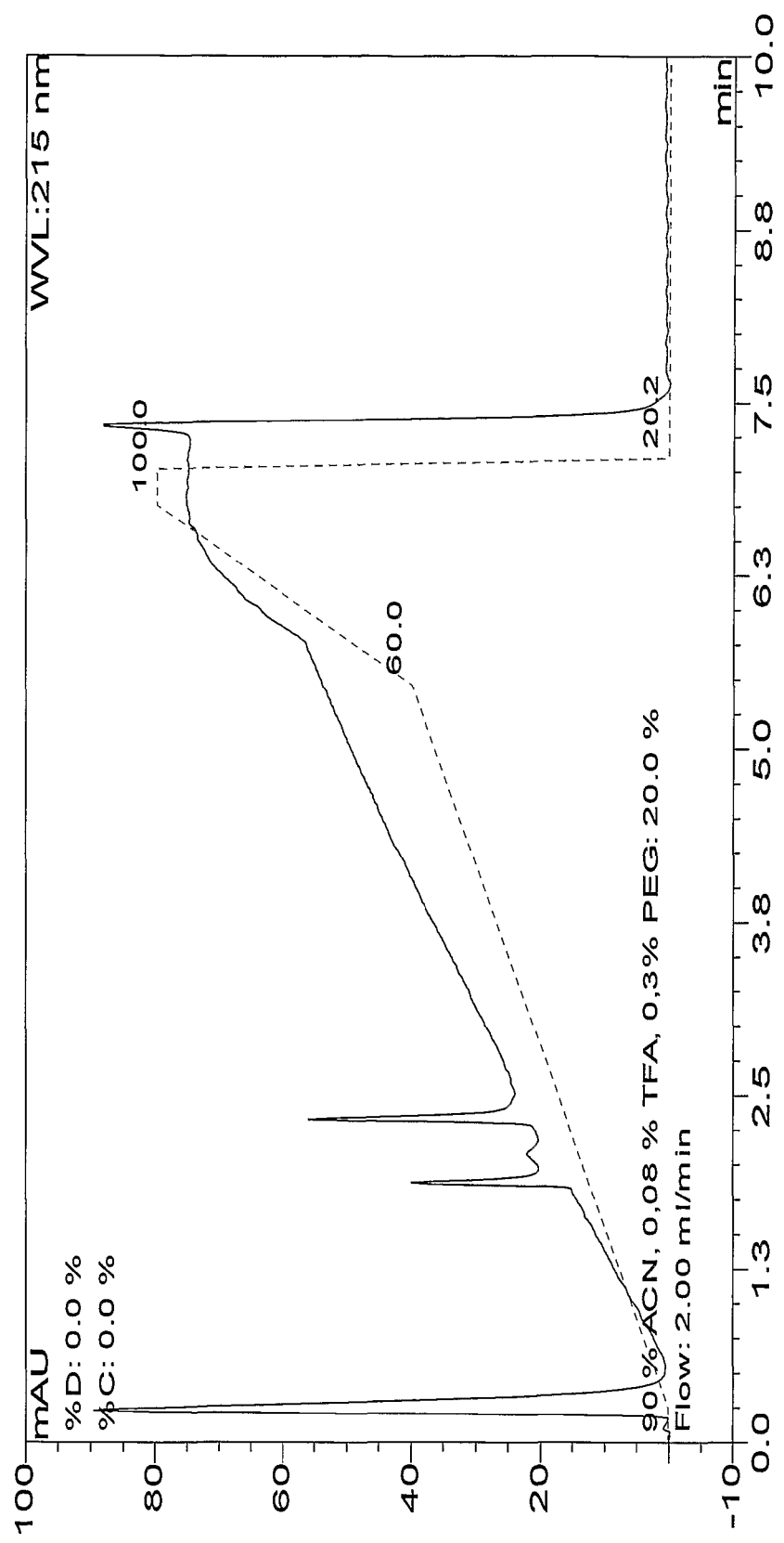
FIG. 9: Shows an elution profile from RP-HPLC of fraction B5 from FIG. 8.

The fractions indicated in FIG. 8 were further separated in a second dimension using RP-HPLC. The second dimension was performed on a Summit HPLC system (Dionex, CA) using a Zorbax Poroshell 300SB-C8 column (2.1×75 mm (5 μm), and the HPLC system was configured as recommended in the instructions for the Poroshell column (Agilent Technologies, CA). Antibody components collected from the cation-exchange chromatography were applied onto the column (5 μl) in 10% CH$_3$CN, 0.1% TFA, 0.3% PEG at a flow rate of 120 ml h$^{-1}$ and eluted by a linear gradient of 90% CH$_3$CN, 0.08% TFA, 0.3% PEG. The column was operated at 70° C. All of the antibody component samples resulted in chromatograms with one or two narrow peaks. The RP-HPLC profile of an antibody component B5 is shown in FIG. 9.

Summary

Since cation-exchange chromatography in the first dimension separates the individual antibodies differing in net charge as well as individual antibodies appearing charge heterogeneous, several antibodies can be represented in a single peak.

Figure 10:
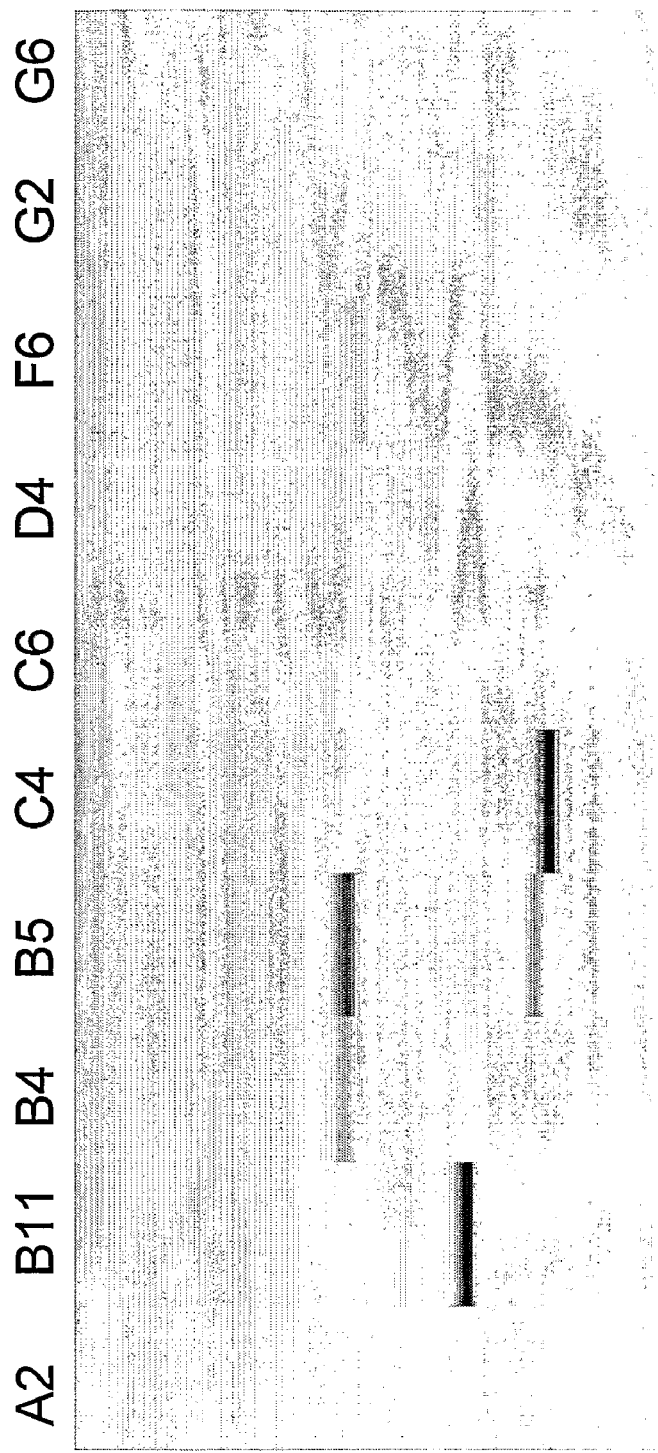
FIG. 10: Shows a 2D LC compositional analysis of a recombinant polyclonal anti-RhD antibody with ten individual members, visualized by a color-coded protein-map (represented in gray-scale).

Several antibody components were separated resulting in a rather complex profile as shown in FIG. 8. As illustrated in Example 2 and 3 it is possible to identify the individual components in each peak by a comparative analysis with monoclonal antibodies analyzed under identical conditions. This was, however, not performed in the present experiment since the purpose was to provide a fingerprint for comparison of samples among each other without having to assign each monoclonal antibody in the rpAb. Thus, the combination of cation-exchange followed by RP-HPLC generates data from two dimensions, and detailed color-coded protein maps (ProteoVue software, Eprogen, USA) as illustrated in FIG. 10 can be constructed for evaluation of batch-to-batch consistency, without the need to analyze monoclonal antibodies to characterize the individual members of the complex rpAb.

Example 5

The present example illustrates the characterization of a polyclonal anti-RhD antibody with eight individual members derived from a polyclonal cell culture. The diversity of the polyclonal antibody was assessed using "bulk" N-terminal sequence analysis.

The N-terminal sequences of the individual members present in the polyclonal anti-RhD antibody sample which were analyzed in the present example are shown below in Table 9. The Lambda light chain sequences are shown in italic.

TABLE 9

| RhD # | N-terminal sequences for HC | N-terminal sequences for LC |
|---|---|---|
| 191 | QVQLVESG (SEQ ID NO 5) | EIVLTQS (SEQ ID NO 7) |
| 306 | QVQLVESG (SEQ ID NO 5) | EIVLTQS (SEQ ID NO 7) |
| 201 | QVQLVESG (SEQ ID NO 5) | EIVLTQS (SEQ ID NO 7) |
| 196 | QVQLVESG (SEQ ID NO 5) | DIQMTQS (SEQ ID NO 8) |
| 244 | QVQLVESG (SEQ ID NO 5) | DIQMTQS (SEQ ID NO 8) |
| 324 | EVQLVESG (SEQ ID NO 6) | EIVLTQS (SEQ ID NO 7) |
| 319 | QVQLVESG (SEQ ID NO 5) | QTVVTQR (SEQ ID NO 9) |
| 203 | EVQLVESG (SEQ ID NO 6) | QSALTQP (SEQ ID NO 10) |

The protein A purified anti-RhD rpAb was analyzed by reducing SDS-PAGE (NuPAGE 4-12%). The polypeptides were electrotransferred onto a PVDF membrane and subsequently stained with Coomassie Blue according to the manufacturer's instructions.

One band of approx. 53 kDa corresponding to the heavy chain (HC) and two bands of approx. 25 and 30 kDa corresponding to Kappa and Lambda+Kappa light chains, respectively, were clearly visible on the Coomassie blue stained PVDF membrane. These bands were cut out and subjected to N-terminal sequence analysis, using an ABI Procise protein sequencer (Applied Biosystems, CA) and standard programs. The sequencing results are summarized in Table 10 below.

TABLE 10

| Cycle #. | HC | LC (~25 kDa) | LC (~30 kDa) |
|---|---|---|---|
| 1 | Q, E | E, D | E, D, Q |
| 2 | V | I | I, T |
| 3 | Q | V, Q | V, Q |
| 4 | L | L, M | L, M, V |
| 5 | V | T | T |
| 6 | E | Q | ND |
| 7 | S | S | ND |

ND = Not determined

The sequences for the HCs are identical except for the first residue, whereas the Kappa LCs are conserved for residue two, five, six and seven and the Lambda LCs are conserved for residue one, five and six (see Table 9).

The result obtained from the sequencing of the HC is in agreement with the expected sequences as presented in Table 10. The sequence data from the Kappa LC band of ~25 kDa indicated the presence of antibodies with the N-terminal sequence EIVLTQS (SEQ ID NO 7), corresponding to RhD191, 324, 201, and 306, and antibodies with the N-terminal sequence DIQMTQS (SEQ ID NO 8) corresponding to RhD244 and 196. With the present technique it was, however, not possible to assess whether all the individual members were present in the polyclonal antibody sample. Sequencing the LC band of ~30 kDa indicated the presence of RhD319 antibody judged by the presence of a Val in cycle three and four. No evidence for the presence of RhD203 antibody was obtained (no S and A in cycle two and three, respectively). However, ion-exchange chromatography and N-terminal sequence analysis of this recombinant monoclonal antibody strongly suggest that the LC of RhD203 has a partial blocked N-terminus. Thus, it can not be conclusively determined by the N-terminal sequence analysis whether this antibody is present or not in the analyzed mixture. In addition, it seems that the 30 kDa band also contains some Kappa LC, since there are E and D residues present in cycle one and an M residue present in cycle 4.

In summary, bulk N-terminal sequence analysis can be used to identify the presence of individual antibodies if they differ in their sequences either at the HC or the LC and are not blocked at the N-terminal. This method is quantitative as long as the N-termini of the individual polypeptides are not partially blocked.

Example 6

The present example illustrates the characterization of a polyclonal anti-RhD antibody with eight individual members derived from a polyclonal cell culture. The diversity of the antibody was analyzed by isolating unique marker peptides originating from the variable region using either RP-HPLC or ion-exchange chromatography (IEX) for peptide separation.

Peptide Generation by Digestion of Isolated Heavy Chains and Light Chains

A polyclonal anti-RhD antibody sample with eight individual members was purified from the supernatant of a polyclonal cell culture by affinity chromatography using HiTrap rProtein A columns. Lyophilized material was dissolved in 6 M guanidium hydrochloride, 0.5 M EDTA, 0.2 M Tris HCl, pH 8.4, reduced (DTT) and carboxymethylated (iodoacetic acid). Heavy chains and light chains were separated by gel filtration on a Superose 12 column (10/300 from Amersham Biosciences, GE Healthcare) in 6 M Guanidium HCl, 50 mM sodium phosphate, pH 8.4 on an Ettan LC system (Amersham Biosciences, GE Healthcare, England). The separated HC (~3.5 mg/ml) and LC (6.5 mg/ml) were digested with Endoproteinase Asp-N (Roche, 1 054 589) at an enzyme to substrate concentration of 1:500 in sodium phosphate, pH 8.

Isolation of Unique Peptides by RP-HPLC

Aliquots of individual Asp-N digests of isolated HC and LC obtained from the polyclonal antibody sample were applied to an Agilent 1100 LC/MSD SL system equipped with a Zorbax 300SB-C18 (2.1×150 mm) 5 μm column connected to a guard column (Zorbax 300SB-C8, 2.1×12.5 mm, 5 μm) equilibrated in 0.1% TFA using a flow rate of 0.2 ml/min. Peptides were eluted using a linear gradient of 0.080% TFA, 70% acetonitrile. Peptides were detected spectrophotometrically at 220 nm and analyzed by on-line MS (atmospheric pressure ionization (API) electrospray). A mixture of 75% propionic acid/25% isopropanol was added post-column to the mobile phase to increase the signal. The obtained mass spectra were analyzed using Chemstation software (Agilent Technologies, CA) and BioLynx software (Micromass, Waters Corporation, MA).

Results from the MS analysis of the Asp-N digests of HC and LC are summarized in Table 11 and 12, respectively. Both tables indicate theoretical and detected masses which are given as average masses.

TABLE 11

Results for the heavy chain

| RhD # | Peptides | Theoretical mass (Da) | Found mass (Da) | Theoretical HPLC index | Retention time (min) |
|---|---|---|---|---|---|
| 191 | D2 | 5891.6 | 5891.3 | 156.5 | 137.0 |
| | D8 | 4208.8 | 4208.4 | 133.8 | 110 |
| 196 | D1 | 5795.6[a]* | 5795.1 | 196.7 | 161.7 |
| | D1-2 | 6297.1* | 6296.7 | 179.1 | 158.0 |
| | D7 | 4196.7[b] | 4196.4 | 114.6 | 98.1 |

TABLE 11-continued

Results for the heavy chain

| RhD # | Peptides | Theoretical mass (Da) | Found mass (Da) | Theoretical HPLC index | Retention time (min) |
|---|---|---|---|---|---|
| 201 | D6 | 4196.7[b] | 4196.4 | 114.6 | 98.1 |
| | D1 | 5710.5* | 5709.5 | 184.8 | 159 |
| 203 | D1 | 5840.6 | 5840.4 | 188.0 | 156.3 |
| | D6 | 4196.8[b] | 4196.5 | 111.2 | 95.1 |
| 244 | D1 | 5795.6[a]* | 5795.1 | 194.9 | 161.7 |
| | D1-2 | 6644.5* | 6644.0 | 210.5 | 171.2 |
| | D7 | 4196.7[b] | 4196.4 | 114.6 | 98.1 |
| 306 | D1 | 5795.6[a]* | 5795.1 | 196.7 | 161.7 |
| | D1-2 | 6694.5* | 6693.9 | 198.2 | 162.5 |
| | D8 | 4168.6 | 4168.4 | 118.4 | 94.7 |
| 319 | D1 | 5809.6* | 5809.2 | 201.6 | 162.5 |
| | D1-2 | 6659.5* | 6659.1 | 191.5 | 159.6 |
| | D7 | 4196.7[b] | 4196.4 | 114.6 | 98.1 |
| 324 | D1 | 5919.8 | 5919.4 | 183.7 | 146.3 |
| | D1-2 | 6729.7 | 6729.3 | 181.7 | 166.5 |
| | D7 | 4224.8 | 4224.6 | 111.3 | 96.1 |

[a]Different peptides with the same mass.
[b]peptides (four identical and one different) with nearly the same mass.
*Indicate a N-terminal cyclized Gln (PyroGlu)

TABLE 12

Results for the light chain

| RhD # | Peptides | Theoretical mass (Da) | Found mass (Da) | Theoretical HPLC index | Retention time (min) |
|---|---|---|---|---|---|
| 191 | d1 | 6537.3 | 6537.2 | 167.5 | 74.2 |
| | d1-2 | 7530.3 | 7530.2 | 168.9 | 71.7 |
| | d1-4 | 10281.4 | 10281.1 | 259.0 | 91.0 |
| | d1-6 | 13719.3 | 13718.8 | 367.2 | 109.8 |
| | d5-6 | 3455.9 | 3455.5 | 114.8 | 95.1 |
| 196 | d2 | 7151.0 | 7150.7 | 186.6 | 93.9 |
| | d3 | 4649.2 | 4648.8 | 150.4 | 84.8 |
| 201 | d1 | 8504.5 | 8504.1 | 229.7 | 82.5 |
| 203 | d5 | 6356.1 | 6355.6 | 168.5 | 90.6 |
| 244 | d2-3 | 7165.1 | 7164.7 | 180.5 | 88.2 |
| | d4 | 4520.1 | 4520.0 | 122.2 | 75.2 |
| 306 | d1-d2 | 6565.6 | 6565.2 | 231.7 | 90.2 |
| | d1-d5 | 11727.2 | 11726.8 | 380.0 | 105.2 |
| | d2 | 3206.7 | 3206.5 | 152.9 | 80.3 |
| 319 | d1 | 8668.7* | 8668.2 | 255.1 | 85.2 |
| | part of d1 (7-83) | 8029.0 | 8028.6 | 246.8 | 84.3 |
| 324 | d1 | 8518.5 | ND | 232.8 | ND |
| | d2 | 4862.5 | ND | 164.2 | ND |

As seen in Table 11, thirteen peptides from the variable HC and sixteen peptides from the variable LC can be identified as unique marker peptides and some peptides from the variable region of HC, (e.g. D1 from RhD196, RhD244 and RhD306 indicated by [a]) have the same mass, and thus these masses cannot be assigned unambiguously. However, since other masses can be unambiguously assigned to unique peptides in all cases positive identification of all eight antibodies has been obtained. For the LC, unique peptides have been assigned for seven out of eight antibodies (Table 12). The antibody from which information is missing for the LC was RhD324. Thus, the combined MS data from the HC and LC demonstrate that all eight antibodies could be identified in the anti-RhD rpAb sample based on detection of unique peptides from each of the antibodies.

Isolation of Unique Peptides by Cation-Exchange Chromatography

The Asp-N digests of HC and LC were separated by strong cation-exchange chromatography as follows: Aliquots of individual Asp-N digests of isolated HC and LC obtained from the polyclonal antibody, as described above, were applied onto a PolySulfoethyl A column (2.1×100 mm) equilibrated in 10 mM potassium phosphate, 20% (v/v) acetonitrile, pH 3.0 using a flow rate of 0.2 ml/min at room temperature on an Ettan LC system (Amersham Biosciences, GE Healthcare, England). Peptides were subsequently eluted using a linear gradient from 0-500 mM potassium chloride in 10 mM potassium phosphate, 20% or 30% (v/v) acetonitrile, pH 3.0. The eluted peptides were detected spectrophotometrically at 215 nm and fractions were collected based on time fractionation. Aliquots (1 µl) of the fractions were mixed with 1 µl of a solution of α-cyano-4-hydroxycinnamic acid (20 mg/mL) in 70% acetonitrile/30%, 0.1% TFA and applied onto the MS target and washed with 0.1% TFA. The samples were analyzed by MALDI-TOF on an Autoflex TOF (Bruker Daltronics, Bremen, Germany), and external mass calibration was performed using calibration mixtures from Bruker Daltronics (Bremen, Germany). MALDI spectra were analyzed (mass search and internal calibration) using GPMAW 6.1 software (Lighthouse data, Odense, Denmark).

Figure 11:
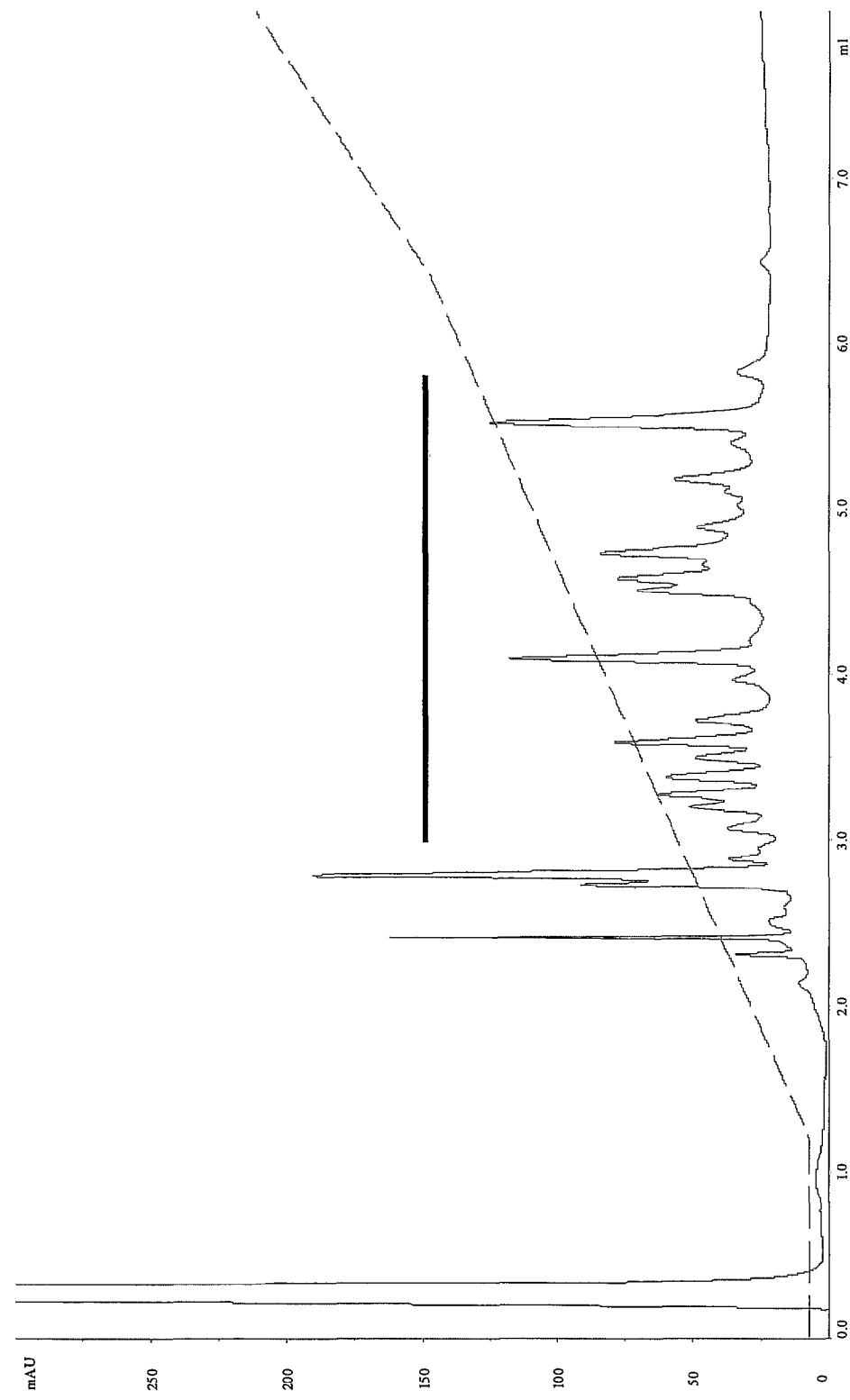
FIG. 11: Shows an elution profile from a strong cation-exchange chromatography of an Asp-N digest of purified LC from a recombinant polyclonal anti-RhD antibody with eight individual members. The bold horizontal line indicates fractions subjected to MALDI-TOF analysis for the identification of marker peptides.

A representative chromatogram containing several peaks from the Asp-N digest of LC is shown in FIG. 11. Results from the MALDI-TOF analysis of the fractions of the Asp-N digests of LC and HC are shown in Table 13 and 14, respectively. Theoretical and found masses are given as monoisotopic masses for masses <3500 Da and as average masses for masses >3500 Da.

TABLE 13

Results from the light chain.

| RhD #. | Peptides | Observed Mass (Da) | Theoretical mass (Da) | SCX fraction no | Theoretical pI |
|---|---|---|---|---|---|
| 191 | d4 | 1365.54 | 1365.53 | B10 | 4.15 |
|  | d3 | 1419.74[a] | 1419.72 | B10 | 3.87 |
|  | part d3-6 (part) | 3090.33 | 3090.31 | B3 | 3.42 |
|  | d6 (part) | 1256.60 | 1256.59 | B9 | 3.0 |
|  | d2 | 1010.45 | 1010.44 | B7 | 7.04 |
|  | d6 (part) | 1858.05[b] | 1858.04 | B7 | 10.10 |
|  | d1 | 6536.30 | 6537.33 | B1 & B2 | 10.28 |
|  | d1 + d2 (part) | 7530.25 | 7530.34 | B1 | 9.91 |
| 196 | d3 (part) | 1858.05[b] | 1858.04 | B7 | 10.10 |
| 201 | d3 | 1844.01[c] | 1844.02 | B7 & B8 | 10.15 |
| 203 | d4 | 2251.11 | 2251.11 | B6 | 7.03 |
|  | d3 | 1068.57 | 1067.57 | B4 | 10.15 |
|  | d2 | 2756.42 | 2756.41 | B2 | 9.44 |
|  | d4 + d5 (part) | 2566.23 | 2566.21 | B7 | 4.11 |
| 244 | d4 (part) | 1858.05[b] | 1858.04 | B7 | 10.10 |
|  | d4 | 4519.42 | 4520.10 | B1 | 9.47 |
| 306 | d5 | 2771.21 | 2771.18 | B9 | 5.27 |
|  | d3-4 | 2423.21 | 2423.20 | B8 | 4.11 |
|  | d1 | 3374.77 | 3374.75 | B7 | 6.55 |
|  | d4 | 1419.74[a] | 1419.72 | B10 | 3.87 |
|  | d6 | 1844.01[c] | 1844.02 | B7 & B8 | 10.15 |
|  | d2 (part) | 1794.91 | 1794..90 | B2 | 8.91 |
| 319 |  |  |  |  |  |
| 324 | d2 (part) | 1858.05[b] | 1858.04 | B7 | 10.10 |

[a]Same peptides.
[b]Same peptides.
[c]Same peptides

TABLE 14

Results from the heavy chain.

| RhD # | Peptides | Theoretical Mass (Da) | Observed mass (Da) | SCX fraction no | Theoretical pI |
|---|---|---|---|---|---|
| 191 | D4 | 1953.0 | 1953.01 | B3 | 6.98 |
|  | part of D2-4 (46-89) | 5134.76 | 5136.35 | C1&C4 | 10.08 |

TABLE 14-continued

Results from the heavy chain.

| RhD # | Peptides | Theoretical Mass (Da) | Observed mass (Da) | SCX fraction no | Theoretical pI |
|---|---|---|---|---|---|
| 196 | part of D6 (99.113)[b] | 1888.89 | 1888.93 | B1 | 9.51 |
|  | part of D1-4 (6-72) | 7343.21 | 7344.01 | C4 | 9.41 |
|  | D5 | 1981.95 | 1981.95 | B6 | 7.01 |
| 201 | D4 | 1995.97[a] | 1995.98 | B6&B7 | 7.01 |
| 203 | D4 | 1995.97[a] | 1995.98 | B6&B7 | 7.01 |
| 244 | D4 | 1982.95 | 1982.94 | B1 | 7.04 |
|  | D6 | 2002.97 | 2002.94 | B1&B3 | 10.12 |
| 306 | D4 | 1809.90 | 1809.91 | B6 | 10.23 |
| 319 | D6 | 2401.03 | 2401.01 | B5 | 9.27 |
|  | D4 | 1995.97[a] | 1995.98 | B6&B7 | 7.01 |
| 324 |  |  |  |  |  |

[a]Same peptide.
[b]Verified by identification of the same peptide with an oxidized Met.

As seen in Tables 13 and 14, fifteen peptides from the variable LC and nine peptides from the variable HC can be identified as unique marker peptides and some peptides from the variable region of HC as well as from the LC have the same mass, and cannot be assigned unambiguously. Thus, it has not been possible to assign unique peptides for HC RhD201, 203 and 324 and for the LC RhD201 and 319 using strong cation-exchange chromatography.

Summary

The results obtained from the two different marker peptide analyses are sufficient to substantiate that the combined data obtained from the MS analyses of the HC and LC enables identification of unique peptides from the variable region from all eight antibodies constituting the anti-RhD rpAb using RP-HPLC. By using strong cation-exchange chromatography six out of eight individual members in the anti-RhD rpAb composition could be identified. The results from the MS analyses have so far not been analyzed to complete detail, but only to the extent shown in Tables 11 to 14.

Example 6A

The present example illustrates the characterization of a recombinant polyclonal anti-RhD antibody with 25 individual members derived from a polyclonal cell culture (bioreactor run). The diversity of the antibody was analyzed by isolation of unique marker peptides originating from the variable regions from the LC or HC using RP-HPLC combined with mass spectrometry for the identification of the peptides.

Peptide Generation by Digestion of Isolated Heavy Chains and Light Chains

A polyclonal anti-RhD antibody sample with 25 individual members was purified from the supernatant of a polyclonal cell culture from a bioreactor run. The purification was performed by affinity chromatography using a MabSelect (Amersham Biosciences, GE Healthcare) column and desalted on a G25 column (Amersham Biosciences, GE Healthcare). Lyophilized material was dissolved in 6 M guanidium hydrochloride, 0.2 M Tris HCl, pH 8.4, reduced (DTT) and carboxymethylated (iodoacetic acid). Heavy chains and light chains were separated by gel filtration on a Superose 12 column (10/300 GL from Amersham Biosciences, GE Healthcare) in 6 M Guanidium HCl, 50 mM sodium phosphate, pH 8.4. The separated HC and LC were digested with Endoproteinase Asp-N (Roche, 1 054 589) at an enzyme to substrate concentration of 1:200 in 1 M urea, 50 mM sodium phosphate, pH 8 over night at 37° C.

Isolation of Unique Peptides by LC-MS

Aliquots of individual Asp-N digests of isolated HC and LC obtained from the polyclonal antibody sample were applied to an Agilent 1100 LC/MSD SL system equipped with a Zorbax 300SB-C18 (2.1×150 mm) 5 µm column connected to a guard column (Zorbax 300SB-C8, 2.1×12.5 mm, 5 µm) equilibrated in 0.1% TFA, 14% ACN using a flow rate of 0.2 ml/min. Peptides were eluted using a linear gradient of 0.08% TFA, 70% acetonitrile. Peptides were detected spectrophotometrically at 220 nm and analyzed by on-line MS (atmospheric pressure ionization (API) electrospray). A mixture of 75% propionic acid/25% isopropanol was added post-column to the mobile phase to increase the signal. The obtained mass spectra were analyzed using Chemstation software (Agilent Technologies, CA) and GPMAW 6.2 software (Lighthouse data, Odense, Denmark).

Results from the MS analysis of the Asp-N digests of HC and LC are summarized in Table 14A, where theoretical and detected masses are given as average masses.

TABLE 14A

Identification of unique hydrophobic peptides from 25 antibodies in an anti-RhD rpAb employing Asp-N cleavage and LC-MS analysis.

| RhD # | Peptides[a] | Theoretical mass (Da) | Found mass (Da) | Retention time (min) |
|---|---|---|---|---|
| 157 | d1 | 7358.2 | 7357.2 | 211 |
| 159 | d4 | 4483.0 | 4482.2 | 213 |
| 160 | d2 | 5585.3 | 5584.5 | 216 |
| 162 | d2 | 4322.0 | 4321.1 | 245 |
| 189 | d1 | 8536.5 | 8535.3 | 203 |
| 191 | d1 | 6537.3 | 6536.4 | 179 |
| 192 | d2 | 5667.4 | 5666.5 | 217 |
| 196 | D1-D2*[b] | 6297.1 | 6295.8 | 303 |
| 197 | d1* | 8696.8 | 8695.5 | 206 |
| 199 | d2 | 5709.4 | 5708.6 | 212 |
| 201 | d1 | 8504.5 | 8503.3 | 202 |
| 202 | d1 | 6448.2 | 6447.3 | 188 |
| 203 | d5 | 6356.1 | 6355.4 | 184 |
| 207 | d1* | 8626.6 | 8625.5 | 198 |
| 240 | d2 | 7056.0 | 7054.9 | 235 |
| 241 | d1 | 6464.4 | 6463.4 | 215 |
| 245 | d2 | 5749.4 | 5748.6 | 226 |
| 293 | D1 | 5854.7 | 5854.1 | 277 |
| 301 | d4 | 4559.3 | 4558.5 | 221 |
| 305 | d4 | 4510.1 | 4509.3 | 187 |
| 306 | d2 | 3206.7 | 3206.1 | 189 |
| 317 | d1 | 6364.2 | 6363.2 | 225 |
| 319 | d1* | 8668.7 | 8667.4 | 210 |
| 321 | d7 | 4945.6 | 4944.9 | 222 |
| 324 | D1 | 5919.8 | 5919.3 | 280 |

[a]D and d denote peptides from HC and LC generated by Asp-N, respectively, and the peptides are numbered from the N-terminus to the C-terminus of the predicted sequences. Hence, d4 denotes a peptide produced by cleavage at the 3rd and 4th Asp-N site in the LC polypeptide.
[b]This peptide contains a missed cleavage site.
*Indicate an N-terminal cyclized Gln (pyroGlu).

As seen in Table 14A, 22 peptides from the variable part of a LC and 3 peptides from the variable part of a HC can be identified as unique marker peptides. Thus, the MS data from the HC and LC unambiguously demonstrate that all 25 antibodies could be identified in the anti-RhD rpAb sample based on detection of unique peptides from each of the antibodies.

Example 7

The present example illustrates the generation of anti-idiotype peptides with specificity towards individual members of a recombinant polyclonal anti-RhD antibody, as well as the assessment of the concentration of one individual member in a recombinant polyclonal antibody.

Generation of Anti-RhD Antibody-Specific Peptide Ligands.

A phage library displaying seven amino acids in random sequence order at the N-terminal end of pIII (New England Biolab) was used for affinity selection of peptide binders to individual anti-RhD antibodies. Both a linear and a constrained version of the peptide library were used for the selection. Microtiter plates (Maxisorb, NUNC) were coated at 4° C. for 12-16 h with purified monoclonal anti-RhD antibody at 10 µg/ml using 100 µl per well. All the twenty-five individual antibodies contained in the recombinant polyclonal anti-RhD antibody were used to screen for anti-idiotype peptides. However, in situations where the recombinant polyclonal antibody contain a large number of individual members (e.g. above 50), sentinel antibodies may be selected for the screening. Preferably, a number of sentinel antibodies corresponding to at least 4% of the total number of antibodies constituting the recombinant polyclonal protein are selected, even more preferred the sentinel antibodies constitute at least 8%, 12%, 16%, 20%, 30% or 50% of the total number of antibodies constituting the recombinant polyclonal protein are selected. The coated plates were subsequently washed in PBS, 0.05% Tween-20 and then blocked with 2% skimmed milk/PBS. Bacteriophages at ~$10^{11}$ pfu/100 µl were used for each panning round. The constrained and linear libraries were mixed and panned together as a mixture in 2% skimmed milk/PBS. After 1 h incubation at room temperature bound phages were eluted with glycine/HCl, pH=2.2 for 10 min followed by neutralization with Tris-HCl, pH=9.0. After three to four rounds of panning, single clones were isolated, DNA extracted and sequenced in the region corresponding to the random peptide region. Table 15 below shows alignments of deduced amino acid sequences from single clones.

TABLE 15

| Target Antibody | Clone # | Peptide sequence |
|---|---|---|
| Anti-RhD162 | 162-B11 | ACMGYGPRMCGGG |
|  |  | (SEQ ID NO 11) |
|  | 162-B12 | ACMGYGPRMCGGG |
|  |  | (SEQ ID NO 11) |
|  | 162-C01 | ACMGYGPRMCGGG |
|  |  | (SEQ ID NO 11) |
|  | 162-C02 | ACMGYGPRMCGGG |
|  |  | (SEQ ID NO 11) |
|  | 162-C04 | ACMGYGPRMCGGG |
|  |  | (SEQ ID NO 11) |
|  | 162-C05 | ACMGYGPRMCGGG |
|  |  | (SEQ ID NO 11) |
|  | 162-C06 | ACMGYGPRMCGGG |
|  |  | (SEQ ID NO 11) |
|  | 162-C07 | ACMGYGPRMCGGG |
|  |  | (SEQ ID NO 11) |
|  | 162-C08 | ACMGYGPRMCGGG |
|  |  | (SEQ ID NO 11) |
|  | 162-C09 | ACMGYGPRMCGGG |
|  |  | (SEQ ID NO 11) |
|  | 162-C10 | ACPGDGPRMCGGG |
|  |  | (SEQ ID NO 12) |
|  | 162-C12 | ACMGYGPRMCGGG |
|  |  | (SEQ ID NO 11) |
|  | 162-D01 | ACMGYGPRMCGGG |
|  |  | (SEQ ID NO 11) |
|  | 162-D03 | ACMGYGPRMCGGG |
|  |  | (SEQ ID NO 11) |
|  | 162-D04 | ACMGYGPRMCGGG |
|  |  | (SEQ ID NO 11) |
|  | Consensus - PEP162 | CMGYGPRMC |
|  |  | (SEQ ID NO 13) |
| Anti-RhD202 | 202-01 | ACMPRNPLECGGG |
|  |  | (SEQ ID NO 14) |
|  | 202-05 | ACAPRNPYECGGG |
|  |  | (SEQ ID NO 15 |

TABLE 15-continued

| Target Antibody | Clone # | Peptide sequence |
|---|---|---|
| | 202-07 | ACPRNPFEMCGGG (SEQ ID NO 16) |
| | 202-06 | ACYPRHPLDCGGG (SEQ ID NO 17) |
| | Consensus - PEP202 | CAPRNPYEC (SEQ ID NO 18) |
| Anti-RhD305 | 305-01 | ACTTLLHFLCGGG (SEQ ID NO 19) |
| | 305-06 | ACTTLLHFLCGGG (SEQ ID NO 19) |
| | 305-07 | ACTTLLSFLCGGG (SEQ ID NO 20) |
| | 305-10 | AGTSLLAFLCGGG (SEQ ID NO 21) |
| | 305-05 | ACNLLLQFLCGGG (SEQ ID NO 22) |
| | Consensus - PEP305 | CTTLLHFLC (SEQ ID NO 23) |

Three synthetic peptides with specific affinity towards either anti-RhD162, 202 or 305, respectively, were synthesized according to the deduced consensus amino acid sequence of groups of related sequences. Each synthetic peptide was coupled to Biotin at the C-terminus.

The specificity of each peptide was tested by ELISA. Briefly, ELISA plates were coated with Streptavidin at 4° C. for 12-16 h with Streptavidin at 5 µg/ml using 100 µl per well. Then, peptide diluted to ~10 µg/ml in PBS was added, followed by incubation for 1 h and removal of excess peptide by washing. The plates were subsequently blocked in 2% skimmed milk/PBS and washed tree times in PBS. Each of the individual anti-RhD antibodies was added separately at various dilutions starting at 10 µg/ml. Bound antibody was detected using an anti-human IgG-conjugate (Caltag cat #H10307). The plates were washed five times and detection was carried out by adding 25 µl of chromogene (TMB, Kem-En-Tech). Reactions were terminated 15-25 min later by adding 25 µl of 1 M $H_2SO_4$. Absorbance values were measured at 450 nm. Testing each peptide against the panel of monoclonal anti-RhD antibodies showed that reactivity is specific for the appropriate individual member-protein. Hence, PEP162 only bound anti-RhD162 antibody, PEP202 only bound anti-RhD202 and PRP305 only bound anti-RhD305 with a signal-to-noise ratio above 10.

Determination of the Amount of Anti-RhD305 Antibody in a Recombinant Polyclonal Anti-RhD Antibody Using proper dilutions of purified anti-RhD305 monoclonal antibody as a reference standard it was possible to determine the amount of anti-RhD305 antibody relative to the total amount of antibodies in a mixture of recombinant polyclonal anti-RhD antibody. Briefly, ELISA plates were coated with Streptavidin and incubated with PEP305 diluted to ~10 µg/ml in PBS for 1 h. After incubation, excess peptide was removed by washing. The plates were subsequently blocked in 2% skimmed milk/PBS and washed tree times. A recombinant polyclonal anti-RhD antibody composed of 25 individual anti-RhD antibodies (the sample) was added at dilutions ranging from 1 to 16384 fold. The sample was analyzed in quadruple. In separate wells on the same plate, serial dilutions (in triplicate) of monoclonal anti-RhD305 antibody starting at 10 ug/ml were added as reference samples in order to generate a standard curve. Bound antibody was detected using an anti-human IgG-conjugate (Caltag cat #H10307). The plates were washed five times and detection was carried out by adding 25 µl of chromogene (TMB, Kem-En-Tech). Reactions were terminated 15-25 min later by adding 25 µl of 1 M $H_2SO_4$. Absorbance values were measured at 450 nm.

The standard curve was linearly proportional to concentration within the following range:

| Monoclonal anti-RhD305 Ab µg/ml | 0.156 | 0.078 | 0.039 | 0.0195 |
|---|---|---|---|---|
| OD450 | 1.509 | 0.990 | 0.567 | 0.338 |

These data resulted in a standard curve with the equation y=0.1161x−0.0256 and $R^2$=0.9812.

The equation determined for the standard curve as well as the dilution factor of the sample was used to calculate the concentration of anti-RhD305 antibody in the recombinant polyclonal anti-RhD antibody sample.

At a 32-fold dilution, the average OD450 measured for the sample was 1.24±0.14, corresponding to an anti-RhD305 antibody concentration of 3.8±0.5 µg/ml in the polyclonal anti-RhD antibody. The total antibody concentration in the recombinant polyclonal anti-RhD antibody sample was 100 µg/ml. Thus, the anti-RhD305 antibody represents 3.8% of the polyclonal antibody sample.

Example 8

The present example illustrates the use of anti-idiotype peptides to identify sentinel antibodies in specific fractions/peaks following separation in one dimension by liquid ion-exchange chromatographic analysis of a recombinant polyclonal anti-RhD antibody.

Figure 12:
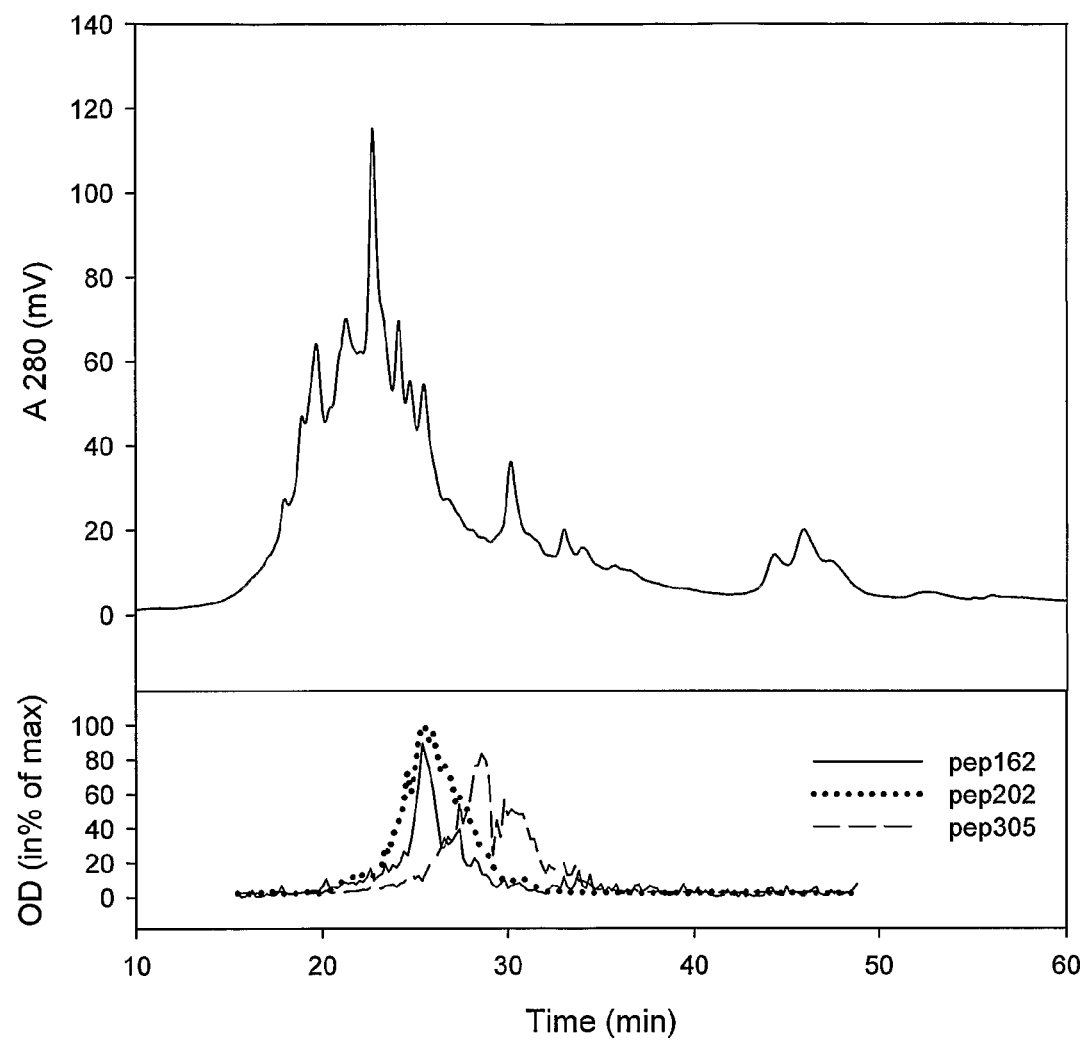
FIG. 12: Shows an overlay of the $OD_{280}$ IEX chromatogram obtained on an anti-RhD rpAb with twenty-five individual members, with ELISA data obtained from three individual ELISA analyses using the anti-idiotype peptides PEP162, PEP202 and PEP305. The ELISA analyses were performed on each fraction obtained by the ion-exchange chromatography. The ELISA data are normalized to % of total OD in order to make the three ELISA assays with PEP162, PEP202 and PEP305, respectively, comparable to each other.

A recombinant polyclonal anti-RhD antibody composed of 25 individual anti-RhD antibodies was separated by cation-exchange chromatography and the fractions were collected. Each fraction was examined by ELISA using the three anti-idiotype peptides (as described in Example 7) in order to detect the presence of a particular anti-RhD antibody in each fraction. An overlay of the chromatogram with the ELISA data performed on each fraction showed that this method can be used to identify individual antibodies in a particular fraction (FIG. 12). Thus, by comparing the absorbance in a particular peak with ELISA data it is possible to make a semi-quantitative assessment of the composition of complex mixtures of homologous proteins.

Example 9

Ensuring compositional stability is a key issue when manufacturing polyclonal proteins for medical use. Specific peptide-ligands capable of identifying individual protein members within a complex mixture of homologous proteins can be used to monitor the compositional stability of a polyclonal protein during manufacturing by extracting media samples during fermentation at different generation time points and applying quantitative detection method such as the ELISA methods described in Example 7.

Figure 13:
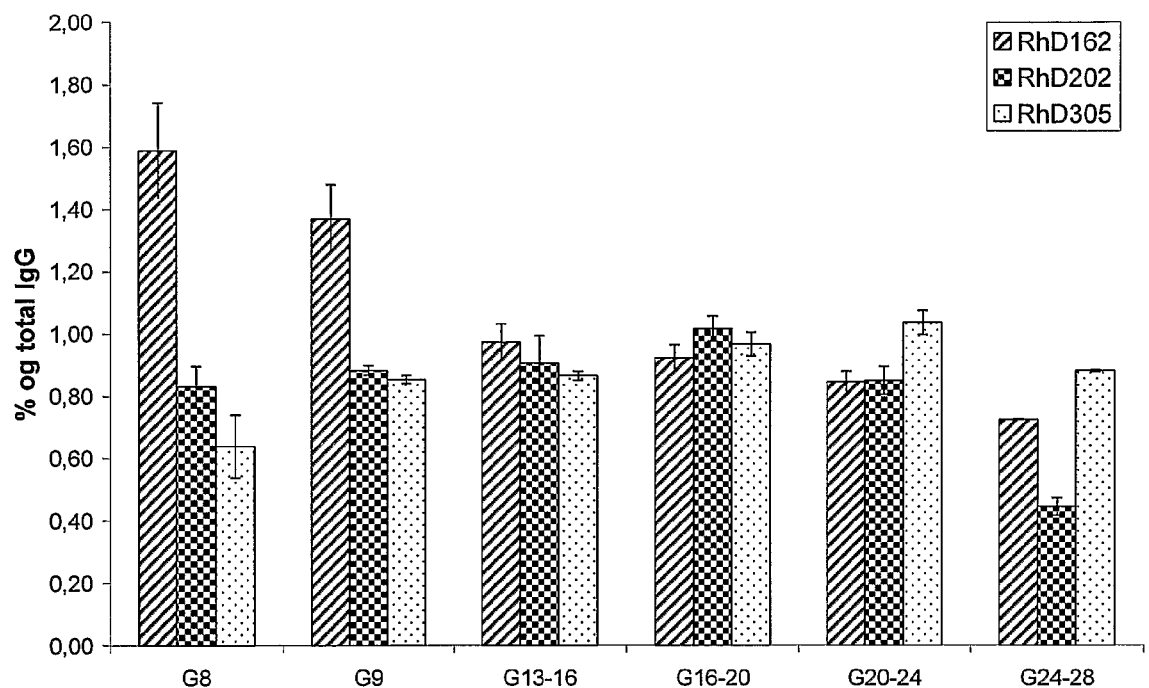
FIG. 13: Shows the distribution of the three sentinel antibodies anti-RhD162, 202 and 305, at different cultivation time points during fermentation. G8 corresponds to day 8 after inoculation of the bioreactor.

In the present example, the actual amount of the three sentinel proteins, the anti-RhD162, 202 and 305 antibodies, were estimated in a perfusion fermentation process of a pWCB producing a recombinant polyclonal anti-RhD antibody composed of 25 unique anti-RhD antibodies. FIG. 13 illustrates the distribution of the three sentinel antibodies (anti-RhD162, 202 and 305) at different cultivation time points during fermentation, with G8 corresponding to day 8 after inoculation of the bioreactor.

Example 10

The present example illustrates a method for the identification of cells producing a particular anti-RhD antibody in a cell culture mixture. In the example, a mixture consisting of two different antibody producing cell lines was analysed using an anti-idiotype peptide and flow cytometry for detection.

Two individual anti-RhD antibody producing cell lines, RhD162 and RhD202, were mixed at defined ratios. The percentages of clone RhD202 are indicated in Table 16.

Figure 14:
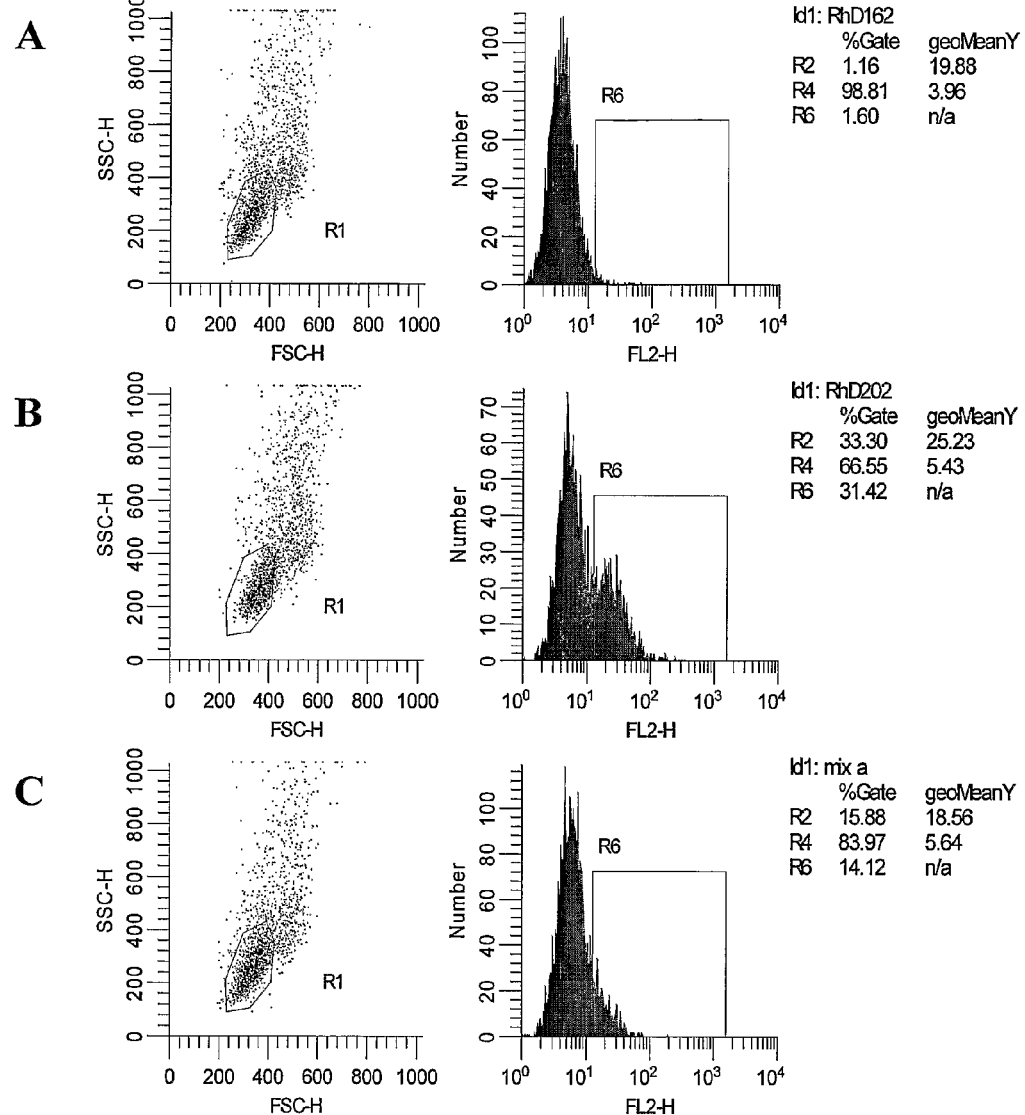
FIG. 14: FACS data of three cell lines stained with PEP202 tetramers. (A) shows the PEP202 negative cell line RhD162. (B) shows cell line RhD202, and (C) shows a 50% mixture of cell lines RhD162 and Rhd202 (corresponding to mix a in the experiment). The first panel in A, B and C show the FSC-SSC dot plots, where R1 is the gating for living and healthy cells based on size (FSC) and granularity (SSC). The histogram in the middle panel depicts the fluorescence intensity of cells. The R6 gate surrounds the tetramer stained cells. The final panel shows the percentages of cells in R6 used in the calculations.

Biotinylated peptide 202 (PEP202 prepared in Example 7) was incubated with phycoerythrin conjugated streptavidin (SA-PE) to form peptide tetramers. The tetramers were incubated with the cell line mixtures for 20 min at RT and the cells were run through a FACS CAlibur flow cytometer (Becton Dickinson). Cells positive for the tetramers were gated as depicted by R1 in FIG. 14. The individual unmixed cell lines were measured as well (FIGS. 14 A and B).

A feature seen for the anti-RhD antibody producing cell lines is the presence of both antibody expressing and non antibody expressing cells within the cell line. To assess the share of PEP202 positive cells in a mixture, the total number of expressing cells needed to be determined. In this example, we assumed that the share of expressing cells in the mixture of RhD162 and RhD202 was the same as in RhD202 alone. This could have been assessed by doublestaining of the cells with Pep202 and anti-IgG antibody (not performed). However, the results indicated the correctness of the assumption. The percentage of RhD202 cells bound by PEP202 tetramer in the mixes was calculated from the percentage of cells in gate 6 (R6), as shown in FIG. 14.

The percentage of the RhD202 cell line in mix a) was calculated according to the following equation, exemplified with the measurements for mix a.

$$\% \ RhD202cells = \frac{\%\text{Gate } R6 \ \text{mix}(x)}{\%\text{Gate } R6 \ RhD202} = \frac{14.12}{31.42} \times 100 = 45\%$$

TABLE 16

| Mix | Actual % RhD202 | Measured % RhD202 |
|---|---|---|
| a | 50 | 45 |
| b | 83 | 79 |
| c | 96 | 87 |
| d | 17 | 15 |

Example 11

The present example illustrates the use of real-time PCR to assess the distribution of the individual clones or a sentinel selection of such clones within a polyclonal cell culture.

The technique is based on the sequence differences among the individual antibody encoding nucleic acid sequences. Due to the variety of the individual antibody encoding sequences a unique TaqMan probe can be designed for the heavy chain and/or light chain for each member represented in the polyclonal cell line. Preferably, one of the CDR regions, CDR1, CDR2 or CDR3, is selected for designing the TaqMan probe. Most preferably, the CDR3 region is selected for designing the TaqMan probe.

Oligonucleotide Design

The primers are preferably designed such that amplicons of 70-150 nucleotides are obtained. Some possible primer designs are: A consensus forward primer annealing in the FR3 region of the heavy or light chain variable region, and the reverse primer annealing in the constant region. A TaqMan probe specific for a part of the CDR region which differs between the individual members of the sample, preferably the CDR3 region, is designed for each clone of interest.

A potential set of primers and probes for the analysis of the polyclonal cell line expressing the following eight anti-RhD antibodies may be designed as indicated below.

Forward and reverse primer for all clones:

```
Fw primer:
CAC GGC TGA GTA TTA CTG TGC     (SEQ ID NO 24)

Rw primer:
TTG GTG GAG CCA CTC GA          (SEQ ID NO 25)
```

TaqMan probes for all the individual clones are shown in Table 17.

TABLE 17

| RhD # | TaqMan probes | |
|---|---|---|
| 191 | AGA AAT TTG TTC GGT GAC TAC GAT CTT AAG TCC | (SEQ ID NO 26) |
| 196 | AGA GAA TTG AGC ACG CAA CGT GGA TAC A | (SEQ ID NO 27) |
| 201 | AGA GAG AGT ACT CTA TAT AGC AGC AGC TGG TAC A | (SEQ ID NO 28) |
| 203 | GAT GGT CTC CTA TAG CAG CAG CTG GTA CC | (SEQ ID NO 29) |
| 244 | GAG AGA CTC TGT TCG GGG AGT CAG TAG AT | (SEQ ID NO 30) |
| 306 | GGG TAC TCT GTA TAG CAG CAG CTG GTA CA | (SEQ ID NO 31) |
| 319 | AGA GAC CTA CAA GGG TAT AGA AGC AGC TGG TAC | (SEQ ID NO 32) |
| 324 | CCG ACG ATT TTT GGA GTG GGC C | (SEQ ID NO 33) |

An alternative primer design for the heavy chain encoding sequences constitute a forward primer annealing in the $V_H$-$D_H$ junction and a reverse primer in the constant region, and the TaqMan probe in the $J_H$-C junction as described in Rasmussen, T. et al. 2000. Exp. Hematol. 28, 1039-1045.

Real-Time Quantitative PCR mRNA or genomic DNA is extracted from pelleted cells. If mRNA is used as template it is reverse transcribed to generate cDNA prior to the real-time PCR. A number of real-time PCR reactions corresponding to the number of clones to be analysed is set up.

The real-time assays are optimised with regards to primer concentrations and TaqMan probe concentrations. Reactions are performed in triplicates in 96 well plates sealed with optical adhesive covers. PCR reactions are done in commercial PCR mastermix and performed in ABI prism 7000 (Applied Biosystems) with subsequent analysis using the ABI prism 7000 SDS software.

Analysis of the Diversity

The $C_T$ values of the different clones are compared to each other, and the distribution of each clone in the polyclonal cell line is calculated. The method may be applied to assess batch-to-batch variation as well as clonal stability over time during an individual production run.

Example 12

The present example illustrates a method for evaluating and demonstrating the polyclonal nature of a polyclonal cell line (e.g. a pWCB) capable of producing a recombinant polyclonal antibody by means of DNA sequencing of the variable region of the heavy and/or light chain antibody genes from single-cell clones derived from the polyclonal cell line.

Single-Cell Cloning

An ampoule of the pWCB is thawed and cultured for a few days in complete medium to reconstitute good cell viability. Subsequently, single-cell clones are obtained by limiting dilution, where the cells are plated in 96-well cell culture plates at a density of 1 cell/well, in complete culture medium. The cells are incubated at 37° C., 5% $CO_2$ for 10-20 days, and the plates are then scored visually for wells with single colonies under a microscope.

Alternatively, single-cell clones from the pWCB are obtained using a FACS cell sorter. Viable pWCB cells are gated and sorted into 96-well plates pre-filled with 100 μl conditioned complete medium at 1 cell/well. The cells are incubated and scored for single colonies as described above.

Nucleic Acid Sequencing

When the single cell colonies in the wells have grown to confluence, aliquots (10-20 μl) from each of a desired number of wells (for example 100) are transferred to new 96-well plates to be used as template in DNA sequencing reactions. The sequencing is either performed at the mRNA level or the genomic level using between 1 and 100 or 1 and 1000 cells, respectively. In the first case, a PCR fragment covering enough of the variable region to distinguish the different antibody heavy and light chain genes present in the pWCB (typically at least the CDR3 region) is generated by standard RT-PCR technology e.g. using the commercially available Qiagen one-step RT-PCR kit, following the instructions from the manufacturer. The cells are lysed prior to the PCR reaction. The resulting PCR fragment is gel-purified using e.g. Qiagen Qiaquick Gel Extraction kit and used as template in a standard DNA sequencing reaction followed by analysis on an automated DNA sequencing machine such as ABI Prism™ 3100 Genetic Analyzer (Applied Biosystems). Alternatively, DNA sequencing is performed on genomic DNA as described above, except that the reverse transcription step is skipped.

For characterization of the anti-RhD recombinant polyclonal antibody, the following primers are used:

PCR Primers for VH Amplification:

```
RhD #001: 5'TCTCTTCCGCATCGCTGTCT      (SEQ ID NO 34)

RhD #007: 5'AGGAAAGGACAGTGGGAGTGGCAC  (SEQ ID NO 35)

PCR primers for VL amplification:
RhD #005: 5'CGTTCTTTTTCGCAACGGGTTTG   (SEQ ID NO 36)

RhD #008: 5'AAGACCGATGGGCCCTTGGTGGA   (SEQ ID NO 37)

Sequencing primers are:
VH:       5'AACGGGTTTGCCGCCAGAACA     (SEQ ID NO 38)

VL:       5'CCGAGGGACCTGAGCGAGT       (SEQ ID NO 39)
```

ELISA on Single Cells Using Anti-Idiotype Peptides

As a supplement to the nucleic acid sequencing, the clonal composition of a mixture of antibody producing cells such as a polyclonal working cell bank can be assessed using an anti-idiotype peptide ELISA.

The sorted single cells are cultivated for approximately 14 days, thereby generating isogenic cell cultures from the single clones. The supernatant from these cultures can be analyzed for the presence of specific anti-RhD antibodies using anti-idiotype peptides in an ELISA assay as described in Example 7. This will provide information with respect to the number of clones producing a particular individual member. If the amount of an individual member is compared to the total amount of antibody producing cells (e.g. by measuring IgG on all isogenic cell cultures), a quantitative measure for the fraction of cells producing individual anti-RhD antibodies in the polyclonal cell culture can be obtained.

Example 13

The present example demonstrates the use of cation-exchange chromatographic analysis to estimate clonal diversity during down-stream processing (DSP) of a recombinant polyclonal antibody.

Down-Stream Processing

Figure 15:
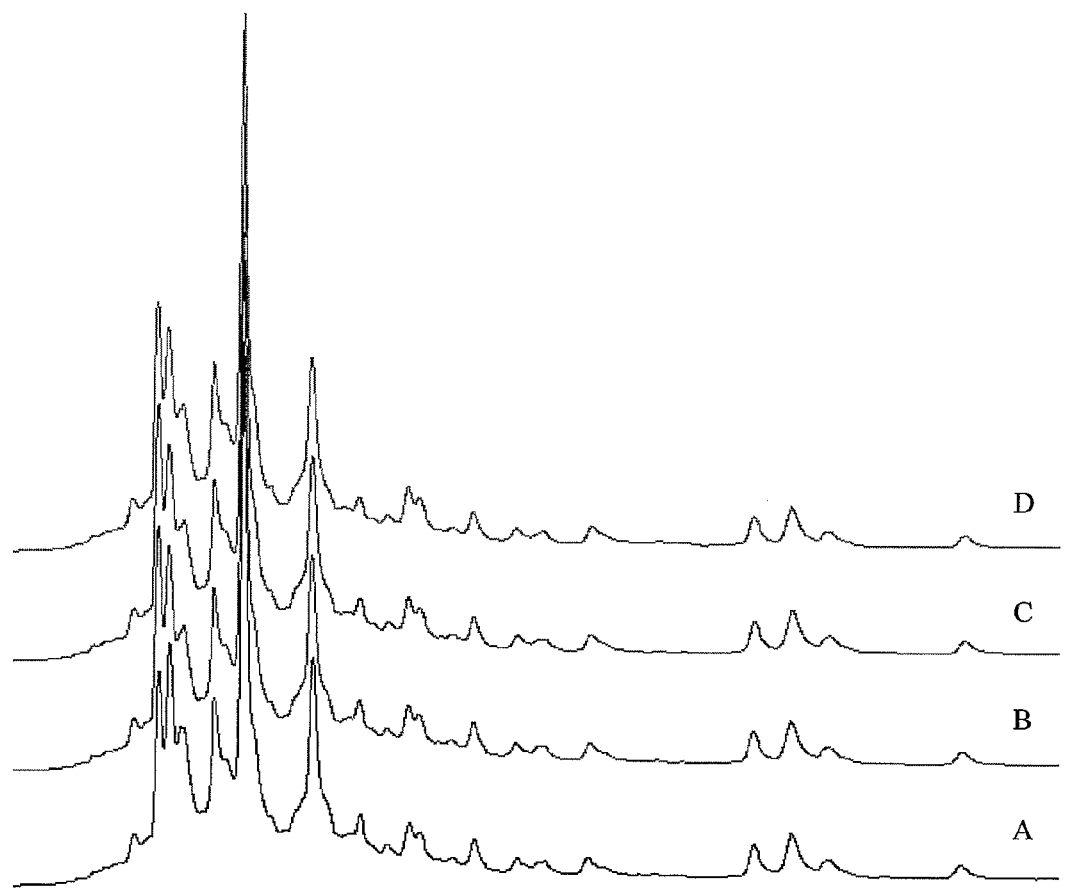
FIG. 15: Cation-exchange chromatography profiles showing samples taken at different stages during down-stream processing of an anti-RhD rpAb sample containing 25 individual members represented by material collected following capture elution (A), Sephadex G-25 (B), DEAE-Sepharose (C), and MEP Hypercel (D).

An anti-RhD rpAb sample, containing 25 individual members, from a developmental bioreactor run was purified using the following DSP steps:
1. capture of the antibodies using a MAbSelect column
2. virus inactivation at pH 3
3. buffer exchange using a sephadex G-25 column
4. anion-exchange chromatography using a DEAE-sepharose column
5. virus filtration using a Planova 15N filter, and
6. hydrophobic charge induction chromatography using a MEP hypercel column
7. ultra filtration/diafiltration using a milipore biomax filter Analysis of Clonal Diversity after Individual DSP Steps Cation-exchange chromatography was used to analyse the clonal diversity during DSP of a recombinant polyclonal antibody composition. Samples taken after step 1, 3, 4 and 6 during DSP of a anti-RhD rpAb was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-500 mM sodium chloride in 25 mM sodium acetate, pH 5.0 at a flow rate of 60 ml h−1. The antibody components were detected spectrophotometrically at 280 nm and the chromatograms were compared (FIG. 15) to detect the potential loss of clonal diversity during DSP. In the present example it was demonstrated, using cation-exchange chromatography that the clonal diversity is essentially unchanged during DSP of a recombinant polyclonal antibody.

Example 14

IEX analysis of more than 40 antibodies against RhD has revealed that a substantial number of the individual antibodies display a "3 peak pattern" as shown in FIG. 16B. Carboyxpeptidase B treatment, as well as carbohydrate analysis have indicated that this charge heterogeneity is not caused by C-terminal lysine clipping or presence of sialic acid (data not shown).

The present example demonstrates that the charge heterogeneity is due to PyroGlu formation, and how site-directed mutagenesis can be used to obtain homogeneous IEX patterns.

Expression and Purification of Antibodies

Stable cell lines (obtained as described in Danish patent application PA 2004 01133 filed Jul. 20, 2004) each expressing a distinct recombinant anti-Rhesus D monoclonal antibody from a specific site on their genome were adapted to suspension culture in serum-free Excell 302 medium (JRH Biosciences, Andover, UK) supplemented with 4 mM L-glutamine (Invitrogen) and anti-clumping agent (Invitrogen) diluted 1:250, expanded and banked at −150° C. using conventional freezing procedures.

The supernatants were harvested from the cell cultures prior to banking, and the supernatant were filtered prior to purification of the anti-RhD monoclonal antibodies using affinity chromatography (Protein A) essential as described in Example 1.

Strong Cation-Exchange Chromatography

The monoclonal antibodies purified in the previous step were subjected to strong IEX chromatography essentially as described in Example 1. The IEX column of Table 18 summarizes the number of peaks present in the IEX profiles of selected antibodies, such IEX profiles are also presented in FIG. 16.

N-Terminal Sequence Analysis

N-terminal sequence analysis of the separated peaks from the IEX analysis of 2 selected antibodies (RhD198 and RhD307) was performed in solution, by Edman sequencing using a Procise 494 Sequencer (Applied Biosystems, CA) operated as described by the manufacturer. The sequence analysis demonstrated that the charge heterogeneity was due to partial cyclization of the N-terminal Gln of the HC (see Table 18). Thus, the first peak contained antibodies with totally blocked N-terminus of the HC (the N-termini of the HC have 0 charge); second peak corresponded to antibodies where one of the N-termini of the HC were blocked (the N-termini of the HC have +1 charge), and the third peak most likely represented antibodies where the N-terminal Gln of the HC were unmodified (the N-termini of the HC have 2+ charge). Cyclization of the N-terminal glutamine residue to PyroGlu renders it refractory to Edman sequencing.

A number of other anti-RhD antibodies likewise displaying such a "3 peak pattern" or a "1 peak pattern" were analyzed by N-terminal sequence analysis by subjecting the antibody to SDS page which was electro-blotted onto PVDF membranes. The HC and LC band on these blots were subjected to Edman sequencing.

A few antibodies harbouring an N-terminal Gln in the HC(RhD162, RhD240) was shown to be to totally blocked in accordance with their IEX profiles ("1 peak pattern"), while antibodies (RhD196, RhD305 and RhD306) with the "3 peak pattern" were found to be partially blocked as expected (see Table 18). The interpretations are based on sequence yields as well as the relative percentage of the different charge variants (0, +1 and 2+) in the IEX profile.

TABLE 18

| RhD # | Seq analysis HC[a] | Seq analysis LC[a] | IEX pattern | Comments |
|---|---|---|---|---|
| 162[b] | QVQLV; no seq.[d] SEQ ID NO 40 | DIQLT; DIQ SEQ ID NO 42 | 1 peak | Total blocked N-termini of HC |
| 196[b] | QVQLV; QVQLV SEQ ID NO 40 | n.d. | 3 peaks | Partially blocked N-termimi of HC |
| 306[b] | QVQLV; QVQLV SEQ ID NO 40 | EIVLTQS; EIVLTQS SEQ ID NO 7 | 3 peaks | Partially blocked N-termimi of HC |
| 240[b] | QLQLQ; no seq.[d] SEQ ID NO 41 | DIQMT; DIQMT SEQ ID NO 43 | 1 peak | Total blocked N-termimi of HC |
| 305[b] | QVQLV; QVQLV SEQ ID NO 40 | n.d | 3 peaks | Partially blocked N-termimi of HC |
| 198[c] | P1: QVQLV; no seq.[d] P2: QVQLV; QVQLV SEQ ID NO 40 | P1: DIQMT; DIQMT P1: DIQMT; DIQMT SEQ ID NO 43 | 3 peaks | Total blocked & partial blocked N-termini of HC are seen in p1 & p2, respectively. |
| 307[c] | P1: QVQLV; no seq.[d] P2: QVQLV; QVQLV SEQ ID NO 40 | P1: DIQLT; DIQLT P1: DIQLT; DIQLT SEQ ID NO 42 | 3 peaks | Total blocked & partial blocked N-termini of HC are seen in p1 & p2, respectively. |

[a]Expected and obtained N-terminal sequences are indicated in regular and bold font style, respectively.
[b]Data obtained from blot.
[c]Data obtained from isolated fractions (peak 1 & 2) from IEX analysis (analyzed in solution). [d]Cyclization of the N-terminal glutamine residue to PyroGlu renders it refractory to Edman sequencing. n.d.; not determined Site-Directed Mutagenesis Site-directed mutagenesis was used to remove the charge heterogeneity from a selected antibody by changing the N-terminal Gln to a Glu. The expression plasmid RhD189 encoding a full-length antibody with an N-terminal Gln in the heavy chain and an N-terminal Glu residue in the LC chain, was used. The VH region in this plasmid is flanked by an AscI site in the 3' end of the signal peptide coding region and a silent XhoI site in the J-region.

Mutagenesis was performed with the following primers:

RhD189 forward:
TGGGCGCGCCGAGGTGCAGCTGGTGGAGTCTGG    (SEQ ID NO 44)

RhD189 reverse:
GGAGGCG<u>CTCGAG</u>ACGGTGACCGTGGTCCC    (SEQ ID NO 45)

AscI site in the forward primer and XhoI site in the reverse primer are underlined, while the Glu codon (GAG) in the N-terminus of the VH region is shown in bold. The RhD189 plasmid was used as template in PCR reactions with the above mentioned primers. PCR reactions were performed with the Phusion DNA polymerase (Finnzymes, Finland) for 25 cycles according to the manufacturer's instructions. VH band of approximately 400 bp was purified on a 1% agarose gel, incubated with BioTaq DNA polymerase, repurified on an agarose gel and cloned into the pCR2.1TOPO vector (Invitrogen, CA) according to the manufacturer's instructions. Clones containing the VH insert were verified by sequencing. The original VH fragment was excised from the plasmid RhD189 with AscI and XhoI and the mutated fragment from the pCR2.1TOPO plasmid was inserted instead. Endotoxin free plasmid midiprep (Macherey-Nagel, Germany) was prepared from a positive colony from the cloning and sequenced to verify the presence of the correct fragment.

The antibody was subjected to SDS-PAGE analysis, electroblotted followed by N-terminal sequencing of the HC band to verify the replacement of Gln to Glu (data not shown).

Figure 17:
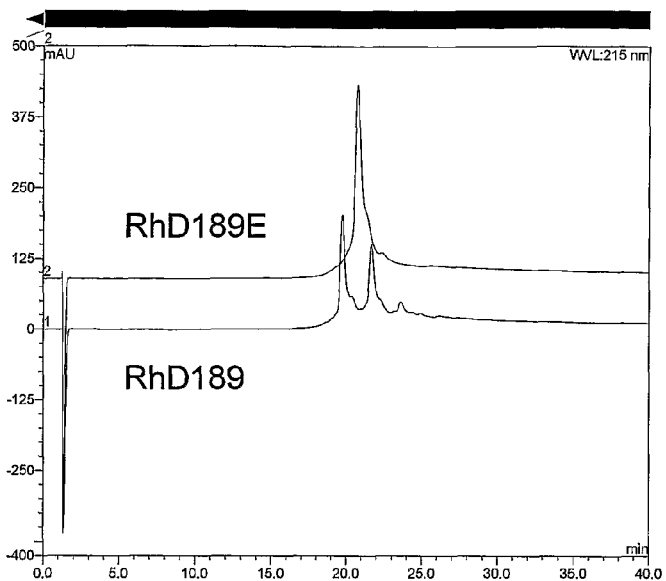
FIG. 17: IEX analysis of RhD189 and the mutated Glu variant RhD189E.

Exchanging the N-terminal Gln to Glu of the HC of antibody RhD189, displaying a "3 peak" IEX profile, resulted in a significant different profile with only one peak (FIG. 17). Thus the charge heterogeneity had been eliminated successfully by changing the N-terminal Gln residue to a Glu residue.

Binding Assay

To assess whether the N-terminal mutation affected the functionality of the antibody, the native antibody, RhD189, as well as its mutated Glu counterpart, RhD189E, was assayed for binding to RhD-positive erythrocytes.

Erythrocytes were prepared from whole blood obtained from healthy donors after informed consent at the Blood Bank, Aalborg Hospital, DK, by washing the blood three times in PBS (Gibco, Invitrogen, United Kingdom) containing 1% bovine serum albumin (BSA, Sigma-Aldrich, Germany). The erythrocytes were resuspended and stored at 4° C. as a 10% solution in ID-Cellstab (DiaMed, Switzerland).

The binding capacity of the antibodies was measured using RhD-positive erythrocytes at $5 \times 10^4$ cells/µl in PBS, 1% BSA. Dilutions of the antibodies were made in PBS, 1% BSA in triplicate in 96 well plates (Becton Dickinson Labware, NJ, USA). Fifty µl of the antibody solution were mixed with 50 µl of erythrocytes and incubated at 37° C. for 40 min. The cells were washed twice (300 g, 2 min) in PBS, 1% BSA. Eighty µl of phycoerythrin-conjugated goat anti-human IgG, (Beckman Coulter, CA, USA) diluted 1:20 in PBS, 1% BSA was added to each sample and left at 4° C. for 30 min. The samples were washed in PBS, 1% BSA and in FacsFlow (Becton Dickinson, Belgium) (300 g, 2 min), and resuspended in 200 µl FACSFlow. The samples were run on a FACSCalibur (Becton Dickinson, CA, USA) and data analysis performed using CellQuest Pro and Excel.

Figure 18:
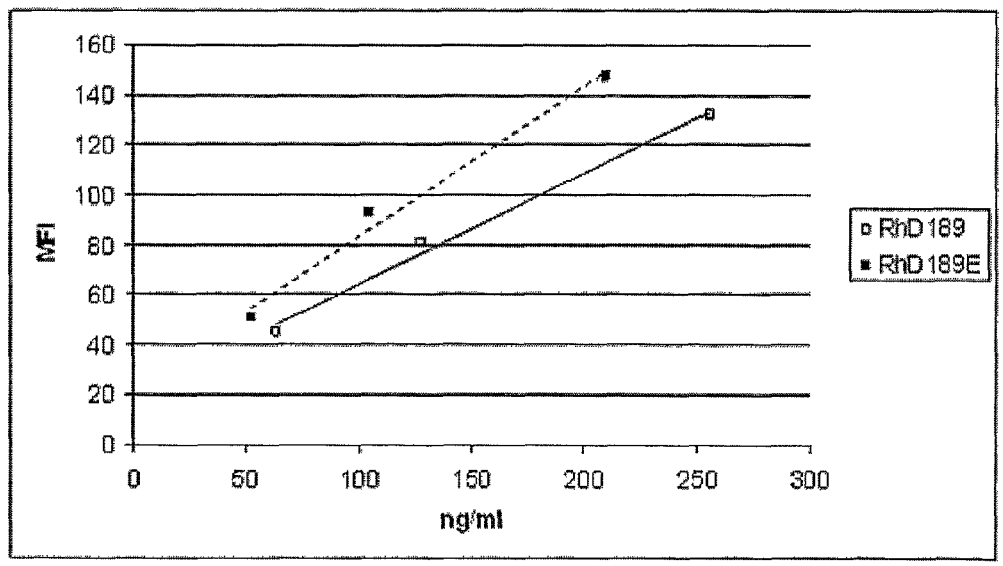
FIG. 18: Binding activity of Glu variant RhD189E, and its native counterpart RhD189. Binding of the antibodies to RhD-positive erythrocytes was measured by FACS and the mean fluorescence intensity (MFI) is shown as a function of the antibody concentration.

As shown in FIG. 18, no significant difference in binding capacity to RhD-positive erythrocytes was observed between the Glu variant and its native counterpart.

Summary

The heterogeneity observed in IEX profiles of many anti-RhD antibodies was due to partial cyclization of the N-terminal Gln residue in these antibodies. Exchanging the N-terminal Gln for Glu residues of the HC in anti-RhD antibodies eliminates the inherent N-terminal charge heterogeneity, presumably without affecting the binding potency to RhD-positive erythrocytes.

---

The invention claimed is:

1. A method for characterizing a polyclonal cell sample wherein said sample is a cell culture fraction comprising cells producing a recombinant polyclonal antibody that comprises individual antibodies having different variable regions, said method comprising:
 obtaining aliquots of said sample without prior isolation of single cells or individual clones, and
 analyzing the aliquots of said sample by one or more genetic analyses of the protein-encoding sequences, such that information related to relative proportion or presence of sequences encoding individual antibody members of said sample is obtained.

2. The method according to claim 1, wherein said genetic analyses are selected from RFLP, T-RFLP, microarray analysis, quantitative PCR and nucleic acid sequencing.

3. The method according to claim 1, further comprising analyzing aliquots of said sample or of a cell culture supernatant of said sample by at least one protein characterization technique selected from the group consisting of i) chromatographic analyses which separate proteins according to physicochemical properties, ii) analysis of proteolytic digestions of the antibodies, iii) "bulk" N-terminal sequencing and iv) analysis using specific detector molecules for the antibodies.

4. The method according to claim 3, comprising at least one chromatographic analysis based on a physico-chemical property other than size.

5. The method according to claim 3, wherein an individual chromatographic analysis is based on physico-chemical properties selected from the group consisting of i) net charge, ii) hydrophobicity, iii) isoelectric points, and iv) affinity.

6. The method according to claim 3 or 5, wherein said chromatographic analyses are performed as a multidimensional chromatography.

7. The method according to claim 3, wherein the analysis of proteolytic digestions of the antibodies is performed in order to isolate N-terminal marker peptides or peptides with characteristic amino acid side chain functionality.

8. The method according to claim 3, wherein said at least one protein characterization technique is performed on aliquots of a cell culture supernatant.

9. The method according to claim 1, wherein said characterization is based on analysis of one or more sentinel nucleic acid sequences present in said sample.

10. The method according to claim 1, wherein at least two analytic techniques are applied to analyze said samples, said at least two analytic techniques comprising at least one genetic analysis and at least one protein characterization technique.

11. The method according to claim 10, wherein
 (i) one analytic technique is a protein characterization technique selected from the group consisting of chromatographic analyses which separate proteins according to physicochemical properties and analysis of proteolytic digestions of the antibodies, and
 (ii) one analytic technique is a genetic analysis, selected from the group consisting of RFLP, T-RFLP, microarray analysis, quantitative PCR, and nucleic acid sequencing.

12. The method according to claim 1, wherein said samples are obtained from a single polyclonal cell culture at different time points during the cultivation and the relative proportions of sequences encoding individual antibodies are compared.

13. The method according to claim 1, wherein said samples are obtained from different polyclonal cell cultures at a particular time point and the relative proportions of sequences encoding individual antibodies are compared.

14. The method according to claim 1, further comprising applying a chromatographic analysis based on net-charge, wherein proteins exhibiting N-terminal charge heterogeneity caused by cyclization of N-terminal glutamine residues are subjected to a method for eliminating N-terminal charge heterogeneity comprising changing said N-terminal glutamine residue to another amino acid.

15. The method according to claim 14, wherein said changing is performed by site-directed mutagenesis of the nucleic acid sequence encoding said protein.

16. The method according to claim 14, wherein said changing is performed on one or more individual antibody members of a recombinant polyclonal antibody.

17. The method according to claim 1, wherein the individual antibodies bind different specific antigenic determinants on a desired target antigen.

18. The method according to claim 1, wherein the individual antibodies bind different specific antigenic determinants on different antigens.

19. The method according to claim 3, comprising an analysis of proteolytic digestions of the individual antibodies using isolation of unique marker peptides by cation-exchange chromatography.

20. The method according to claim 4, comprising at least one chromatographic analysis based on hydrophobicity selected from the group consisting of reverse-phase chromatography (RP-HPLC) and hydrophobic interaction chromatography based on salt concentration (HIC).

21. The method according to claim 4, comprising at least one chromatographic analysis based on cation exchange chromatography.

22. The method according to claim 12, further comprising comparing the relative proportions of individual antibodies at different time points during cultivation of the polyclonal cell culture.

23. The method according to claim 13, further comprising comparing the relative proportions of individual antibodies in different polyclonal cell cultures at a particular time point.

24. The method of claim 1, wherein information is obtained with respect to the relative proportion of sequences encoding individual antibody members of said sample.

25. The method of claim 1, wherein information is obtained on levels of mRNA encoding individual antibody members of said sample.

26. The method according to claim 1, comprising at least one genetic analysis selected from the group consisting of RFLP performed at the mRNA level and T-RFLP performed at the mRNA level.

27. The method according to claim 1, further comprising i) using the information obtained to monitor stability of expression of said recombinant polyclonal antibody in a production run, ii) using the information obtained to monitor batch-to-batch variation of said recombinant polyclonal antibody between production runs, or iii) both i) and ii).

28. A method of determining the clonal diversity of a polyclonal cell line during a production run, wherein the polyclonal cell line comprises cells producing a recombinant polyclonal antibody that comprises individual antibodies having different variable regions, said method comprising:
obtaining a first aliquot of a cell culture fraction from said production run, without prior isolation of single cells or individual clones, at a first time point,
obtaining a second aliquot of a cell culture fraction from said production run, without prior isolation of single cells or individual clones, at a second time point, and
analyzing the first and second aliquots of said cell culture fraction by one or more genetic analyses of the protein-encoding sequences, such that information related to relative proportion or presence of sequences encoding individual antibody members of said sample is determined.

29. A method of monitoring the stability of expression of a recombinant polyclonal antibody from a polyclonal cell line that comprises cells producing a recombinant polyclonal antibody that comprises individual antibodies having different variable regions, said method comprising:
obtaining one or more aliquots of a cell culture fraction comprising said polyclonal cell line, without prior isolation of single cells or individual clones, and
analyzing the aliquots of said cell culture fraction by one or more genetic analyses of the protein-encoding sequences, such that information related to relative proportion or presence of sequences encoding individual antibody members of said sample is determined.

* * * * *

UNITED STATES PATENT AND TRADEMARK OFFICE
CERTIFICATE OF CORRECTION

PATENT NO. : 8,288,109 B2
APPLICATION NO. : 11/658021
DATED : October 16, 2012
INVENTOR(S) : Rasmussen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this
Twenty-third Day of September, 2014

Michelle K. Lee
*Deputy Director of the United States Patent and Trademark Office*